United States Patent
Scheiner et al.

(10) Patent No.: US 6,212,434 B1
(45) Date of Patent: Apr. 3, 2001

(54) SINGLE PASS LEAD SYSTEM

(75) Inventors: Avram Scheiner, Vadnais Heights; William Hsu, Circle Pines; David M. Flynn, Lino Lakes; Qingsheng Zhu, Little Canada; John E. Heil, White Bear Lake; Ronald W. Heil, Jr.; Curtis C. Lindstrom, both of Roseville; Robert S. Booker, III; Yayun Lin, both of St. Paul; Peter T. Kelley, Buffalo; Jay A. Warren, North Oaks; Gerrard M. Carlson, Champlin; Carol Werlein, Ham Lake; Aaron W. Janke; Mary Lee Cole, both of St. Paul; Jeffrey T. Bartig, Maplewood; Gary W. Goebel, Vadnais Heights; Douglas A. Heitkamp, White Bear Lake; Randall M. Peterfeso, St. Paul, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/120,824

(22) Filed: Jul. 22, 1998

(51) Int. Cl.[7] ........................................................ A61N 1/05
(52) U.S. Cl. .............................................................. 607/123
(58) Field of Search ................................... 607/122, 123, 607/127, 125

(56) References Cited

U.S. PATENT DOCUMENTS 3,614,955   10/1971   Mirowski ........................ 128/419 D (List continued on next page.)

FOREIGN PATENT DOCUMENTS 2827595   5/1978   (DE) .

(List continued on next page.)

OTHER PUBLICATIONS

Fain, et al., "A New Internal Defibrillation Lead System: Intrapericardial Placement Without Thoracotomy", *Abstracts Circulation*76, Suppl. IV, 1839 (Oct. 1987).

(List continued on next page.)

*Primary Examiner*—Scott M. Getzow
(74) *Attorney, Agent, or Firm*—Schwegman, Lundberg, Woessner & Kluth, P.A.

(57) ABSTRACT

A single-pass endocardial lead electrode adapted for implantation in, on or about the heart and for connection to a system for monitoring or stimulating cardiac activity includes a lead body which is adapted for implantation within a single chamber of the heart, or multiple chambers of the heart. The lead includes a first distal end electrode which has a first electrical conducting surface. The lead body also has a second electrode which has a second electrical conducting surface. The first and second electrodes are either passively or actively attached to the wall of the heart. The lead body also includes a curved portion which facilitates the positioning of the second electrode. The main lead body alternatively includes a recess into which an atrial lead body and an active fixation element attached to one end can travel from a recessed position to a position for fixation to the wall of the heart. The active fixation element can also be moved by turning the terminal pin. The lead body can also include multiple legs, each leg carrying an electrode. The lead is attached to a pulse generator for producing pulses to the multiple sites within the heart. A movement assembly for advancing a helix is also included within the legs and comprises an externally threaded collar which engages with an internally threaded housing or housing insert. The lead further includes a helical tip which has high impedance. The electrode has at least one features of the group: the helix having a coating of an insulating material on its surface, the helix having its surface beyond the distal end of the electrode and the distal end of the electrode having a porous conductive surface at a base of the helix, a porous conductive element at a base of the helix, and a porous conductive element at the end of the electrode having an insulating coating cover from 5–95% of the surface of the porous conductive element. The porous element may further provide a guiding mechanism for the helix as it travels out of the electrode for securing the electrode to the heart.

21 Claims, 34 Drawing Sheets

U.S. PATENT DOCUMENTS

| | | | |
|---|---|---|---|
| 3,804,098 | 4/1974 | Friedman | 128/404 |
| 3,866,615 | 2/1975 | Hewson | 128/419 D |
| 3,942,536 | 3/1976 | Mirowski et al. | 128/419 D |
| 3,949,757 | 4/1976 | Sabel | 128/404 |
| 4,030,508 | 6/1977 | Thalen | 128/418 |
| 4,030,509 | 6/1977 | Heilman | 124/419 D |
| 4,057,067 | 11/1977 | Lajos | 128/418 |
| 4,106,512 | 8/1978 | Bisping | 128/418 |
| 4,136,703 | 1/1979 | Wittkampf | 128/419 P |
| 4,154,247 | 5/1979 | O'Neill | 128/419 P |
| 4,217,913 | 8/1980 | Dutcher | 128/785 |
| 4,270,549 | 6/1981 | Heilman | 128/784 |
| 4,289,144 | 9/1981 | Gilman | 128/785 |
| 4,291,707 | 9/1981 | Heilman et al. | 128/784 |
| 4,311,133 | 1/1982 | Robinson | 128/1 |
| 4,311,153 | 1/1982 | Smits | 128/785 |
| 4,332,259 * | 6/1982 | McCorkle | 607/123 |
| 4,393,883 | 7/1983 | Smyth et al. | 128/785 |
| 4,458,677 | 7/1984 | McCorkle, Jr. | 128/786 |
| 4,463,765 | 8/1984 | Gold | 128/785 |
| 4,497,326 | 2/1985 | Curry | 128/785 |
| 4,548,203 | 10/1985 | Tacker, Jr. et al. | 128/419 |
| 4,559,951 | 12/1985 | Dahl et al. | 128/642 |
| 4,567,900 | 2/1986 | Moore | 128/784 |
| 4,567,901 | 2/1986 | Harris | 128/786 |
| 4,570,642 | 2/1986 | Kane et al. | 128/785 |
| 4,602,645 | 7/1986 | Barrington et al. | 128/786 |
| 4,603,705 | 8/1986 | Speicher et al. | 128/786 |
| 4,624,265 | 11/1986 | Grassi | 128/784 |
| 4,624,266 | 11/1986 | Kane | 128/785 |
| 4,627,439 | 12/1986 | Harris | 128/419 |
| 4,633,880 | 1/1987 | Osypka et al. | 128/642 |
| 4,643,201 | 2/1987 | Stokes | 128/786 |
| 4,646,755 | 3/1987 | Kane | 128/785 |
| 4,649,937 | 3/1987 | DeHaan et al. | 128/784 |
| 4,649,938 | 3/1987 | McArthur | 128/785 |
| 4,662,377 | 5/1987 | Heilman et al. | 128/419 |
| 4,662,382 | 5/1987 | Sluetz et al. | 128/785 |
| 4,664,113 | 5/1987 | Frisbie et al. | 128/344 |
| 4,667,686 | 5/1987 | Peers-Travarton | 128/785 |
| 4,721,115 | 1/1988 | Owens | 128/713 |
| 4,727,877 | 3/1988 | Kallok | 128/419 |
| 4,784,161 | 11/1988 | Skalsky et al. | 128/785 |
| 4,799,486 | 1/1989 | DuFault | 128/419 |
| 4,799,493 | 1/1989 | DuFault | 128/705 |
| 4,817,608 | 4/1989 | Shapland et al. | 128/419 |
| 4,817,634 | 4/1989 | Holleman et al. | 128/784 |
| 4,819,661 | 4/1989 | Heil, Jr. et al. | 128/786 |
| 4,819,662 | 4/1989 | Heil, Jr. et al. | 128/786 |
| 4,827,932 | 5/1989 | Ideker et al. | 128/419 D |
| 4,860,769 | 8/1989 | Fogarty et al. | 128/786 |
| 4,865,037 | 9/1989 | Chin et al. | 128/419 D |
| 4,876,109 | 10/1989 | Mayer et al. | 427/2 |
| 4,886,074 | 12/1989 | Bisping | 128/785 |
| 4,905,691 | 3/1990 | Rydell | 606/47 |
| 4,922,927 | 5/1990 | Fine et al. | 128/786 |
| 4,924,881 | 5/1990 | Brewer | 128/785 |
| 4,938,231 | 7/1990 | Milijasevic et al. | 128/784 |
| 4,944,300 | 7/1990 | Saksena | 128/419 |
| 4,953,551 | 9/1990 | Mehra et al. | 128/419 |
| 4,953,564 | 9/1990 | Berthelsen | 128/784 |
| 4,967,766 | 11/1990 | Bradshaw | 128/785 |
| 4,971,070 | 11/1990 | Holleman et al. | 128/784 |
| 4,972,848 | 11/1990 | DiDomenico et al. | 128/785 |
| 4,998,975 | 3/1991 | Cohen et al. | 128/419 D |
| 5,002,067 | 3/1991 | Berthelsen et al. | 128/786 |
| 5,016,645 | 5/1991 | Williams et al. | 128/784 |
| 5,016,646 | 5/1991 | Gotthardt et al. | 128/784 |
| 5,016,808 | 5/1991 | Heil, Jr. et al. | 228/176 |
| 5,020,544 | 6/1991 | Dahl et al. | 128/784 |
| 5,044,375 | 9/1991 | Bach, Jr. et al. | 128/786 |
| 5,050,601 | 9/1991 | Kupersmith et al. | 128/419 |
| 5,056,516 | 10/1991 | Spehr | 128/419 |
| 5,063,932 | 11/1991 | Dahl et al. | 128/639 |
| 5,076,285 | 12/1991 | Hess et al. | 128/186 |
| 5,083,562 | 1/1992 | de Coriolis et al. | 128/419 |
| 5,105,826 | 4/1992 | Smits et al. | 128/784 |
| 5,107,834 | 4/1992 | Ideker et al. | 128/419 |
| 5,111,811 | 5/1992 | Smits | 128/419 |
| 5,111,812 | 5/1992 | Swanson et al. | 128/419 D |
| 5,129,404 | 7/1992 | Spehr et al. | 128/785 |
| 5,133,353 | 7/1992 | Hauser | 128/419 |
| 5,133,365 | 7/1992 | Heil, Jr. et al. | 128/786 |
| 5,144,960 | 9/1992 | Mehra et al. | 128/786 |
| 5,152,299 | 10/1992 | Soukup | 128/785 |
| 5,165,403 | 11/1992 | Mehra | 128/419 D |
| 5,174,289 | 12/1992 | Cohen | 128/419 PG |
| 5,174,303 | 12/1992 | Schroeppel | 128/786 |
| 5,203,348 | 4/1993 | Dahl et al. | 128/784 |
| 5,209,229 | 5/1993 | Gilli | 128/419 |
| 5,230,337 | 7/1993 | Dahl et al. | 607/5 |
| 5,255,693 | 10/1993 | Dutcher et al. | 607/120 |
| 5,259,394 | 11/1993 | Bens | 607/127 |
| 5,259,395 | 11/1993 | Li | 607/131 |
| 5,261,400 | 11/1993 | Bardy | 607/5 |
| 5,269,319 | 12/1993 | Schulte et al. | 128/786 |
| 5,271,417 | 12/1993 | Swanson et al. | 607/122 |
| 5,282,845 | 2/1994 | Bush et al. | 607/128 |
| 5,300,108 | 4/1994 | Rebell et al. | 607/127 |
| 5,300,110 | 4/1994 | Latterell et al. | 607/130 |
| 5,314,459 | 5/1994 | Swanson et al. | 607/122 |
| 5,324,327 | 6/1994 | Cohen | 607/122 |
| 5,342,414 | 8/1994 | Mehra | 607/127 |
| 5,344,439 | 9/1994 | Otten | 607/126 |
| 5,358,516 | 10/1994 | Myers et al. | 607/116 |
| 5,366,496 | 11/1994 | Dahl et al. | 607/132 |
| 5,374,286 | 12/1994 | Morris | 607/119 |
| 5,383,908 | 1/1995 | Sweeney et al. | 607/5 |
| 5,397,342 | 3/1995 | Heil, Jr. et al. | 607/129 |
| 5,405,373 | 4/1995 | Petersson et al. | 607/121 |
| 5,411,527 | 5/1995 | Alt | 607/5 |
| 5,411,544 | 5/1995 | Mar et al. | 607/122 |
| 5,425,755 | 6/1995 | Doan | 607/119 |
| 5,425,756 | 6/1995 | Heil et al. | 607/128 |
| 5,447,533 | 9/1995 | Vachon et al. | 607/120 |
| 5,447,534 | 9/1995 | Jammet | 607/127 |
| 5,456,706 | 10/1995 | Pless et al. | 607/122 |
| 5,456,708 | 10/1995 | Doan et al. | 607/127 |
| 5,476,499 | 12/1995 | Hirschberg | 607/123 |
| 5,476,501 | 12/1995 | Stewart et al. | 607/127 |
| 5,476,502 | 12/1995 | Rubin | 607/127 |
| 5,492,119 | 2/1996 | Abrams | 128/642 |
| 5,500,008 | 3/1996 | Fain | 607/5 |
| 5,522,874 | 6/1996 | Gates | 607/127 |
| 5,531,780 | 7/1996 | Vachon | 607/120 |
| 5,534,022 | 7/1996 | Hoffmann et al. | 607/122 |
| 5,545,201 | 8/1996 | Helland et al. | 607/127 |
| 5,545,205 | 8/1996 | Schulte et al. | 607/123 |
| 5,554,178 | 9/1996 | Dahl et al. | 607/122 |
| 5,571,163 | 11/1996 | Helland | 607/123 |
| 5,578,068 | 11/1996 | Laske et al. | 607/126 |
| 5,628,778 | 5/1997 | Kruse et al. | 607/123 |
| 5,628,779 | 5/1997 | Bornzin et al. | 607/123 |
| 5,674,272 | 10/1997 | Bush et al. | 607/122 |
| 5,683,447 | 11/1997 | Bush et al. | 607/126 |
| 5,769,881 | 6/1998 | Schroeppel et al. | 607/123 |
| 5,772,693 | 6/1998 | Brownlee | 607/123 |
| 5,851,227 | 12/1998 | Spehr | 607/126 |
| 5,964,795 * | 10/1999 | McVenes et al. | 607/123 |

FOREIGN PATENT DOCUMENTS

| | | | |
|---|---|---|---|
| 0057877 | 8/1982 | (EP) | 607/121 |
| 0211166 | 2/1987 | (EP) | A61N/1/05 |
| 0282047 | 9/1988 | (EP) | 607/127 |
| 452278A2 | 4/1990 | (EP) | A61N/1/05 |
| 0452278 | 10/1991 | (EP) | A61N/1/05 |
| 0460324 | 12/1991 | (EP) | A61N/1/05 |
| 0573275 | 12/1993 | (EP) . | |
| 0612538 | 8/1994 | (EP) | A61N/1/05 |
| 0620024 | 10/1994 | (EP) . | |
| 0672431 | 9/1995 | (EP) | A61N/1/05 |
| 2588758 | 4/1987 | (FR) | A61N/1/05 |
| 2757773 | 12/1996 | (FR) | A61N/1/05 |
| 2032278 | 6/1980 | (GB) | A61M/25/00 |
| 2240721 | 8/1991 | (GB) . | |
| 3-168161 | 7/1991 | (JP) . | |
| 4-40966 | 2/1992 | (JP) . | |
| 89/06148 | 7/1989 | (WO) | A61N/1/05 |
| 92/07616 | 5/1992 | (WO) . | |
| 94/22525 | 4/1993 | (WO) | A61N/1/05 |
| 96/15665 | 11/1994 | (WO) | A01N/1/05 |
| 97/40883 | 4/1996 | (WO) | A61N/1/05 |

OTHER PUBLICATIONS

Jones, D.L., et al., "Internal Cardiac Defibrillation in Man: Pronounced Improvement with Sequential Pulse Delivery to Two Different Lead Orientations", *Circulation, vol. 73, No. 3*, p. 484–491 (Mar. 1986).

* cited by examiner

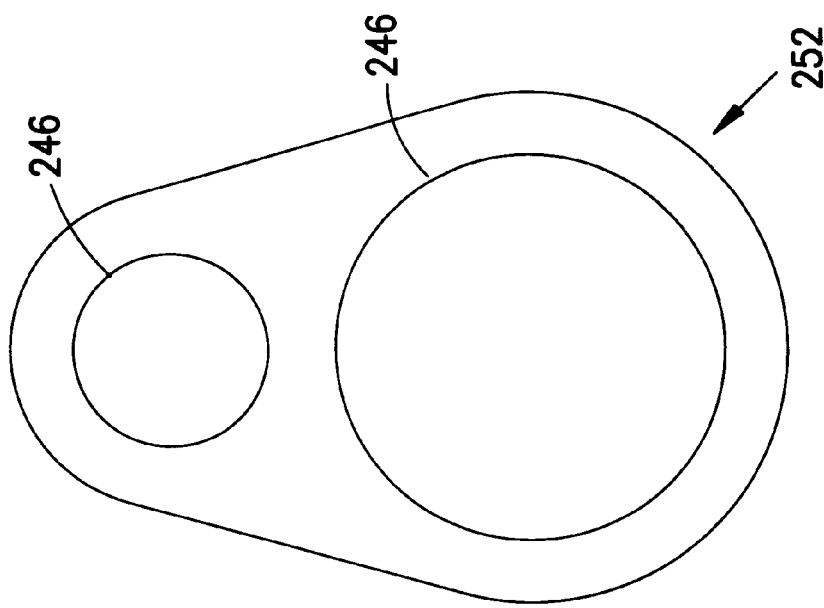
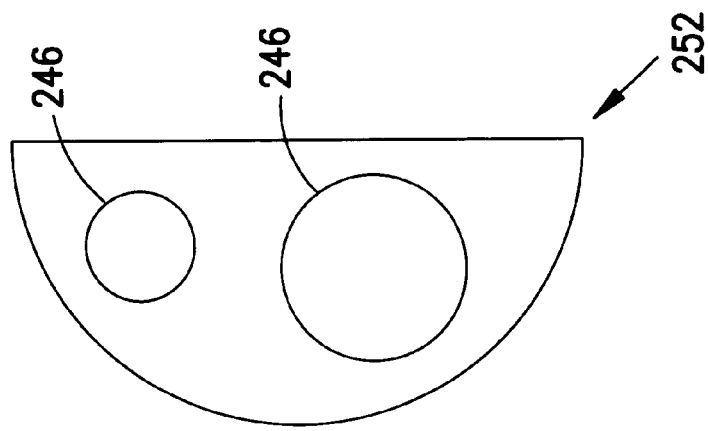

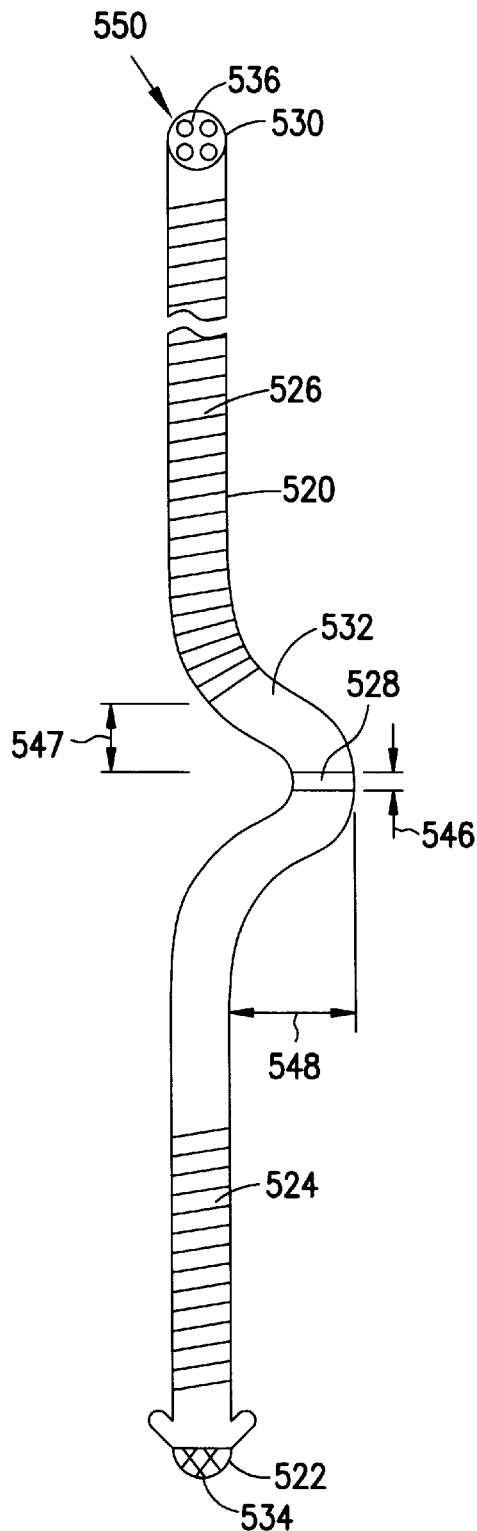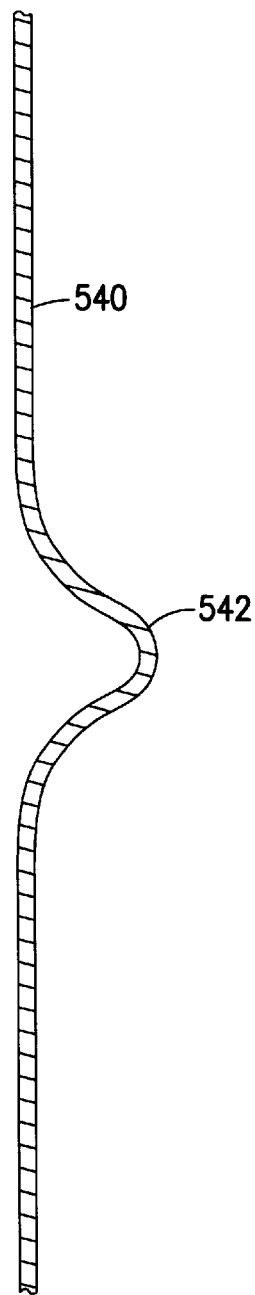
FIG. 17A
FIG. 17B

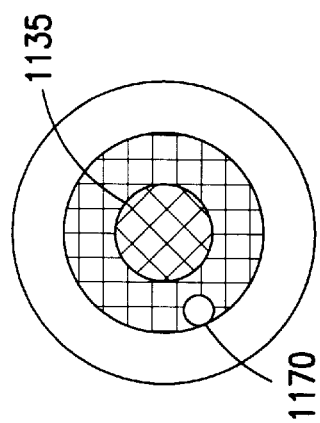
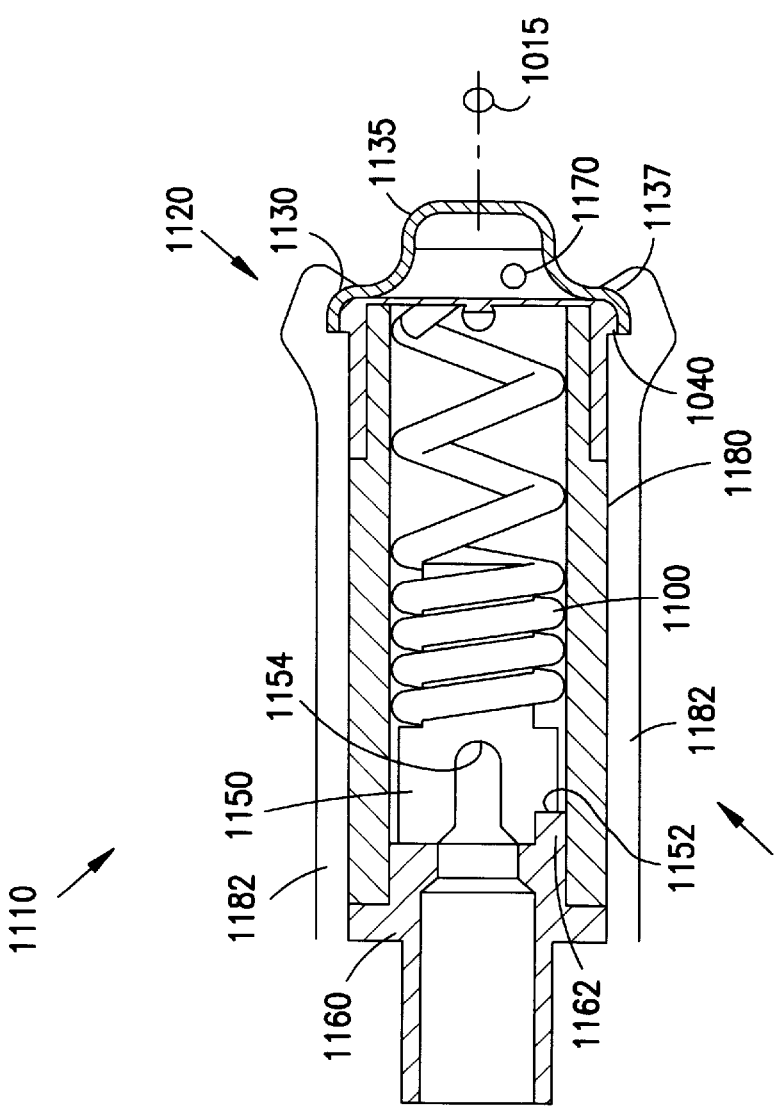

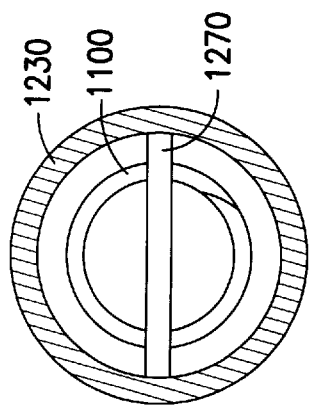
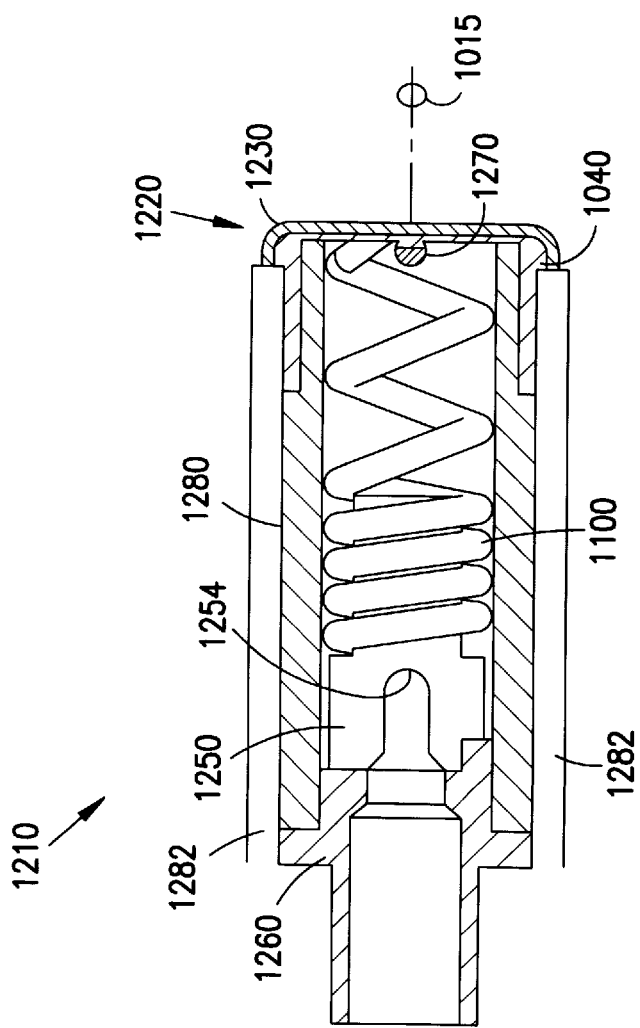

SINGLE PASS LEAD SYSTEM

RELATED APPLICATIONS

This application is related to the following: U.S. Patent Application No. 09/121,020, filed on Jul. 22, 1998, entitled SINGLE PASS DEFIBRILLATION/PACING LEAD WITH PASSIVELY ATTACHED ELECTRODE FOR PACING AND SENSING; U.S. Patent Application 09/121,288, filed on Jul. 22, 1998, entitled HIGH IMPEDANCE ELECTRODE TIP; U.S. Patent Application No. 09/121,005, filed on Jul. 22, 1998, entitled SINGLE PASS LEAD AND SYSTEM WITH ACTIVE AND PASSIVE FIXATION ELEMENTS; U.S. Patent Application No. 09/121,006, filed on Jul. 22, 1998, entitled SINGLE PASS LEAD HAVING RETRACTABLE, ACTIVELY ATTACHED ELECTRODE FOR PACING AND SENSING; U.S. Patent Application No. 09/121,018, filed on Jul. 22, 1998, entitled SINGLE PASS DEFIBRILLATION/PACING LEAD WITH PASSIVELY ATTACHED ELECTRODE FOR PACING AND SENSING; U.S. Patent Application No. 09/129,348, filed Aug. 5, 1998, entitled ATRIAL AND VENTRICULAR CARDIAC LEAD HAVING A MECHANICAL BIAS; U.S. Patent Application No. 09/121,019, filed on Jul. 22, 1998, now U.S. Pat. No. 6,085,119; U.S. Patent Application No. 08/579,872, filed on Dec. 28, 1995, now U.S. Pat. No. 5,776,072; and U.S. Patent Application No. 08/996,355, filed on Dec. 22, 1997, now U.S. Pat. No. 5,885,221; all of which are assigned to a common assignee. The related applications are incorporated herein by reference in their entirety.

FIELD OF THE INVENTION

The present invention relates to the field of leads for correcting arrhythmias of the heart. More particularly, this invention relates to a single lead which can simultaneously pace, sense, and/or defibrillate one or more chambers of the heart.

BACKGROUND OF THE INVENTION

Electrodes implanted in the body for electrical cardioversion or pacing of the heart are well known. More specifically, electrodes implanted in or about the heart have been used to reverse (i.e., defibrillate or cardiovert) certain life threatening arrhythmias, or to stimulate contraction (pacing) of the heart, where electrical energy is applied to the heart via the electrodes to return the heart to normal rhythm. Electrodes have also been used to sense near the sinus node in the atrium of the heart and to deliver pacing pulses to the atrium. An electrode positioned in any chamber of the heart senses the electrical signals that trigger the heartbeat. Electrodes detect abnormally slow (bradycardia) or abnormally fast (tachycardia) heartbeats. In response to the sensed bradycardia or tachycardia condition, a pulse generator produces pacing or defibrillation pulses to correct the condition. The same electrode used to sense the condition is also used in the process of delivering a corrective pulse or signal from the pulse generator of the pacemaker.

There are four main types of pulses or signals which are delivered by a pulse generator. Two of the signals or pulses are for pacing the heart. First of all, there is a pulse for pacing the heart when it is beating too slowly. The pulses trigger the heart beat. These pulses are delivered at a rate to increase the abnormally low heart rate to a normal or desired level. The second type of pacing is used on a heart that is beating too fast. This type of pacing is called antitachycardia pacing. In this type of pacing, the pacing pulses are delivered initially at a rate much faster or slower than the abnormally beating heart until the heart rate can be returned to a normal or desired level. The third and fourth types of pulses are delivered through large surface area electrodes used when the heart is beating too fast or is fibrillating, respectively. The third type is called cardioversion. This is delivery of a relatively low energy shock, typically in the range of 0.5 to 5 joules, to the heart. The fourth type of pulse or signal is a defibrillation signal which is the delivery of a high energy shock, typically greater than 25 joules, to the heart.

Sick sinus syndrome and symptomatic AV block constitute the major reasons for insertion of cardiac pacemakers today. Cardiac pacing may be performed by the transvenous method or by electrodes implanted directly onto the epicardium. Most commonly, permanent transvenous pacing is performed using one or more leads with electrodes positioned within one or more chambers of the heart. The distal end of a lead, sometimes referred to as a catheter, may be positioned in the right ventricle or in the right atrium through a subclavian vein. The lead terminal pins are attached to a pulse generator which is implanted subcutaneously.

Some patients require a pacing system to detect and correct an abnormal heartbeat in both the atrium and ventricle which may have independent rhythms, as well as a defibrillation system to detect and correct an abnormally fast heart rate (tachycardia condition). In the past, a common practice for a patient having to pace both of these chambers would be to provide two different leads attached to the heart. One would be implanted for delivering pacing/sensing/defibrillating to the ventricle and one to the atrium to both pace and sense.

Having two separate leads implanted within the heart is undesirable for many reasons. Among the many reasons are that the implantation procedure for implanting two leads is more complex and also takes a longer time when compared to the complexity and time needed to implant a single lead. In addition, two leads may mechanically interact with one another after implantation which can result in dislodgment of one or both of the leads. In vivo mechanical interaction of the leads may also cause abrasion of the insulative layer along the lead which can result in an electrical failure of one or both of the leads. Another problem is that as more leads are implanted in the heart, the ability to add other leads is reduced. If the patient's condition changes over time the ability to add leads is restricted. Two separate leads also increase the risk of infection and may result in additional health care costs associated with re-implantation and follow-up.

Because of these problems, catheters having electrodes for both pacing and sensing in both chambers of the heart on a single lead body have been used. These leads, known as single pass lead designs, have drawbacks since the single pass lead designs utilize "floating" electrodes or electrodes which are not attached to the endocardial wall of the heart. The catheter having the electrodes which forms the lead body is essentially straight. The electrode or electrodes may float or move slightly at a distance from the endocardial wall within the heart.

The portion of the lead positioned within the atrium of current single-pass endocardial leads has one or more electrodes which are incorporated into the lead body as an electrically conductive cylindrical or semicylindrical ring structure. In other words, the lead body is basically cylindrical and the one or more electrodes positioned within the atrium of the heart are cylindrical metal structures incorporated into the cylindrical lead body. The ring electrode structures do not allow for tissue ingrowth into the electrode to enhance electrode stabilization within the atrium. Since the location of the electrodes is not fixed against the atrial wall, the performance of these leads is more variable. In other words, variations with respect to electrical contact with the wall of the atrium results in suboptimal electrical sensing capability and pacing delivery capability. Typically, the pacing characteristics of a floating electrode are less desirable than the pacing characteristics associated with an electrode fixed to the endocardial wall of the heart. The performance of a lead using a floating electrode is poorer than a lead having electrodes which contact or are nearer the walls of the heart.

Another problem associated with the current straight single pass leads, is that these electrodes may be unable or less able to sense an arrhythmic condition. In addition, the applied voltage or current needed for pacing may be ineffective. Additional energy may have to be used to pace the heart thereby depleting energy from the battery of the pulse generator of the pacing system.

There is a real need for a single-pass transvenous pacing or defibrillation lead. A single-pass lead equipped with such an electrode arrangement would allow for better sensing capability and better pacing therapy to the heart. In addition, there is a need for a single-pass lead having an electrode for positioning within the atrium that allows for tissue ingrowth. Such an electrode would further enhance lead stabilization within the heart. There is also a need for a single-pass endocardial lead which has an electrode for placing within the right atrium of the heart that accommodates eluting anti-inflammatory drugs. There is still a further need for a single pass endocardial lead that is easier for a surgeon to implant.

SUMMARY OF THE INVENTION

A single-pass endocardial lead electrode adapted for implantation and for connection to a system for monitoring or stimulating cardiac activity includes a lead body. The lead, in one embodiment, includes a first distal end electrode or electrode pair which has a first electrical conducting surface. The lead body also has a second electrode or electrode pairs which has a second electrical conducting surface. The second electrode or electrode pair is adapted for positioning and fixation to the wall of the atrium of the heart. A passive fixation element is used as part of the second electrode or electrode pair. The lead body also includes a curved portion which facilitates the positioning and fixing of the second electrode or electrode pair. The curved portion has a radius near the natural radius of the atrium. The first and second electrode may be a single electrode or a bipolar pair. The curve in the lead body, which is positioned in the right atrium of the heart after implantation, positions the electrode closer to the wall of the atrium to enhance the sensing and pacing performance of the lead.

The electrical conducting surface of the second electrode has a relatively small diameter when compared to previous electrodes. The small diameter electrode results in superior electrical performance when compared to previous single-pass endocardial leads. The benefits include increased pacing impedance, increased P-wave signal amplitudes and decreased atrial pacing capture thresholds. The increased impedance lets the battery energy source last longer. The single-pass lead equipped with an atrial electrode capable of being fixed to the endocardial wall allows for better sensing capability and better current delivery to the heart. The second electrode may be placed on the outside of the curved portion of the lead body. The fixed atrial electrode enhances lead stabilization within the heart and the result is no need for two leads in the heart. The costs and complexity associated with implanting and follow-up care for the single pass lead is less than two separate leads.

In another embodiment, the lead includes a first distal end electrode or pair of electrodes for positioning in the ventricle and a second proximal electrode or pair of electrodes for positioning in the atrium. The second electrode or pair of electrodes are adapted for positioning and fixation to the wall of the atrium of the heart. An active fixation element is used as part of the second electrode or electrode pair. The lead body also may include a curved portion which facilitates the positioning and fixing of the second electrode or second pair of electrodes. The lead body also includes at least one recess for positioning an active fixation element within the recess.

In yet another embodiment, the recess is able to house the active fixation electrode as well as a portion of a lead body associated with the atrium (atrial lead body). By moving the terminal pin with respect to a yoke, the lead body is moved out of the recess. The atrial lead body can be a straight lead or a J-shaped lead. The type of atrial lead body used will depend on the placement of the lead within the atrium of the heart and the preference of the surgeon doing the placement. The advantage is that the active fixation electrode is placed into the recess during placement of the lead to prevent it from attaching inadvertently to the subclavian vein or other tissue while it is being inserted.

In another embodiment, an active fixation electrode is included with the lead that can be controllably moved from a recessed position to an attachment position by rotating the terminal pin attached to the conductor coil which is attached to the body of the active fixation electrode.

In yet another embodiment, the lead includes a distal end having a first pacing electrode or electrode pair. The distal end of the lead body also has a second electrode or electrode pair. The second electrode or electrode pair is positioned away from the first electrode or electrode pair. The first and second electrodes fit within a single chamber of the heart for multi-site pacing or pulse delivery to the single chamber. In a first embodiment, the distal end of the lead body includes a curved portion which facilitates the positioning of the first and second electrode or electrode pair within the single chamber. The first electrode may be a single electrode associated with a unipolar arrangement or may be one of a pair of electrodes associated with a bipolar electrode. The second electrode may be either unipolar or bipolar as well.

In another embodiment, the lead includes a first leg for the first electrode and a second leg for the second electrode. One of the first or second legs is movable between a withdrawn position and an extended position. When inserting the lead, the withdrawn leg is within the lead body which eases the task of insertion. In yet another embodiment, the two legs may be withdrawn to a position within the lead for easy insertion. In each of the embodiments, the first electrode and second electrode can be passively or actively fixed.

In another embodiment, the lead extends from two terminal legs at a proximal end of the lead to two electrode legs at a distal end of the lead. Each electrode leg includes a first electrode and a second electrode. The second electrode is adapted for positioning and fixation to the wall of the atrium of the heart.

In one embodiment, a bifurcated lead includes a main lead body which is adapted to carry signals to and from the heart. The main body extends to a first electrode assembly which has a first electrode and a second electrode, and is adapted to be implanted within a first chamber of the heart. The body also extends to a second electrode assembly which has a third electrode and a fourth electrode, and is adapted to be implanted within a second chamber of the heart. In another embodiment, the lead body has an intermediate portion which comprises a quad lumen body. In yet another embodiment, the first electrode leg and the second electrode leg each have a semi-circular profile. A yoke, in another configuration, couples the first electrode leg and the second electrode leg with the intermediate portion. The first electrode assembly and the second electrode assembly can be either actively or passively fixated within the heart. A mesh screen can also be provided to allow for better tissue in-growth.

In another embodiment, a bifurcated lead includes a main lead body which is adapted to carry signals to and from the heart. The main body extends to a first electrode assembly which has a first electrode and a second electrode, and is adapted to be implanted within a first chamber of the heart. The body also extends to a second electrode assembly which has a third electrode and a fourth electrode, and is adapted to be implanted within a second chamber of the heart. The first electrode assembly and the second electrode assembly include an active fixation portion, to which a movement assembly is coupled. In one embodiment, the movement assembly includes an externally threaded portion which is engaged with an internally threaded housing. In another embodiment, the internally threaded portion comprises an insert disposed within the lead.

In another embodiment, a bifurcated lead includes a main lead body which is adapted to carry signals to and from the heart. The main body extends to a first electrode assembly which has a first electrode and a second electrode, and is adapted to be implanted within a first chamber of the heart. The body also extends to a second electrode assembly which has a third electrode and a fourth electrode, and is adapted to be implanted within a second chamber of the heart. The lead is coupled with a signal generator which is adapted for producing pulses to apply to the heart.

According to one embodiment of the present invention, there is provided a body-implantable lead assembly comprising a lead, one end of the lead being adapted to be connected to electrical supply for providing or receiving electrical pulses. The other end of the lead comprises a distal tip which is adapted to be connected to tissue of a living body. The lead is characterized by having either a) a porous electrode at the base of the helix and/or b) an insulating coating over a portion of the helix so that the impedance is increased for the helix as compared to a helix of the same size and materials without an insulating coating. The lead also has an increased impedance or a high impedance which can act to extend the life of the battery. The high or at least the increased impedance may be effected in any of an number of ways, including, but not limited to one or more of the following structures: 1) a fully insulated tissue-engaging tip with an electrode at the base of the insulated tip, 2) a partially insulated (only a portion of the surface area of the engaging tip being insulated), 3) a mesh or screen of material at the distal end of the lead, at the base of an extended engaging tip (whether a fixed or retractable tip), 4) the selection of materials in the composition of the mesh and/or tip which provide higher impedance, 5) the partial insulative coating of a mesh or screen to increase its impedance, and 6) combinations of any of these features. There may be various constructions to effect the high impedance, including the use of helical tips with smaller surface areas (e.g., somewhat shorter or thinner tips). There may also be a sheath of material inert to body materials and fluids and at least one conductor extending through the lead body. The use of these various constructions in the tip also allows for providing the discharge from the tip in a more highly resolved location or area in the tip.

According to another embodiment of the present invention, there is provided a body-implantable lead assembly comprising a lead, one end being adapted to be connected to electrical supply for providing or receiving electrical pulses. The lead further comprises a distal tip which is adapted to be connected to tissue of a living body. The lead also has a high impedance to extend the life of the battery. There may be various constructions to effect the high impedance. There may also be a sheath of material at the distal end of the lead assembly, with the sheath being inert to body materials and fluids and at least one conductor extending through the lead body.

The distal tip electrode is adapted, for example, for implantation proximate to the heart while connected with a system for monitoring or stimulating cardiac activity. The distal tip electrode includes an electrode tip (preferably with only a percentage of its entire surface area being electrically conductively exposed [only a portion of the surface is insulated] to increase its impedance), preferably a mesh screen disposed at a distal end of the electrode tip, a fixation helix disposed within the electrode tip, and a helix guiding mechanism. The mesh screen preferably is electrically active (conductive as well as active), and the area of the mesh screen and the percentage of electrically exposed surface area of the electrode tip can be changed to control electrical properties. Further, the mesh screen can entirely cover an end surface of the electrode tip, or a portion of the end surface in the form of an annular ring. In one embodiment, the helix guiding mechanism includes a hole punctured within the mesh screen. Alternatively, the helix guiding mechanism can include a guiding bar disposed transverse to a radial axis of the electrode. The helix is retractable, and is in contact with a movement mechanism. The movement mechanism provides for retracting the helix, such as during travel of the electrode tip through veins. The helix is aligned with the radial axis of the electrode and travels through the guiding mechanism. The mesh may be tightly woven or constructed so that there are effectively no openings, or the mesh can be controlled to provide controlled porosity, or controlled flow through the mesh.

In another embodiment, the electrode tip includes a mesh screen forming a protuberance on the end surface of the electrode tip. The protuberance is axially aligned with the radial axis of the electrode. The helix travels around the protuberance as it passes through the mesh while traveling to attach to tissue within the heart. The helix also travels around the protuberance as it is retracted away from the tissue within the heart. If the mesh screen is insulated around the protuberance, then a high impedance tip is created. Advantageously, the protuberance allows for better attachment to the cardiac tissue without having the electrode tip penetrating therethrough.

Additionally, a distal tip electrode is provided including an electrode tip, a mesh screen disposed at a distal end of the electrode tip, a fixation helix disposed within the electrode tip, and a helix guiding mechanism. The electrode tip further may include a piston for moving the helix. The piston further may include a slot for receiving a bladed or fixation stylet. When engaged and rotated, the piston provides movement to the helix. The base provides a mechanical stop for the helix and piston when retracted back in to the electrode tip.

In another embodiment, the distal tip assembly is adapted for implantation proximate to the heart while connected with a system for monitoring or stimulating cardiac activity. A fixation helix/piston assembly is housed by an electrode collar, housing, and base assembly. Attached to the proximal end of the helix is a piston which includes a proximal slot for receiving a bladed or fixation stylet. When a stylet is engaged in the slot and rotated, the piston provides movement to the helix. Depending on the embodiment, the fixation helix/piston assembly may be electrically active or inactive. The electrode collar, housing, and base all house the fixation helix/piston assembly. The proximal end of the electrode collar is attached to the distal end of the housing. Furthermore, the proximal end of the housing is attached to the distal end of the base, and the proximal end of the base is directly attached to the conductor coils of the lead.

A mesh screen may be attached to the distal tip of the electrode collar. The mesh screen, in another embodiment, is electrically active and serves as the electrode on the distal tip assembly. The tip may then be fully insulated to increase the impedance of the tip or may be partially insulated (with preselected areas of the helix tip being insulated and other areas being non-insulated) to adjust the impedance of the tip to the specific or optimal levels desired. The area of the mesh screen can be modified to cover differing portions of the end surface of the distal tip assembly to control electrical properties of the lead. The fixation helix travels through a guiding mechanism, where the guiding mechanism allows the fixation helix to be extended and retracted. In one embodiment, the helix guiding mechanism includes a hole formed within the mesh screen. Alternatively, the helix guiding mechanism can include a guiding bar disposed transverse to a radial axis of the electrode collar. The mesh screen and/or guiding bar also serve as a full extension stop when the helix is fully extended. The base serves as a stop when the fixation helix/piston assembly is fully retracted.

In yet another embodiment, the electrode uses a partially insulated fixation helix to provide a relatively high pacing impedance electrode. The fixation helix is insulated using insulating coatings over a portion of the fixation helix.

The above lead embodiments are also incorporated into a system, wherein the lead is operatively coupled with a pulse generator. Signals or pacing pulses produced by the pulse generator which are sent and/or received from the electrodes. The pulse generator can be programmed and the electronics system includes a delay portion so that the timing between a pulse at a first electrode and a pulse at a second electrode.

The provided electrode tip supplies a retractable helix and a mesh screen which advantageously allows for sufficient tissue in-growth. The guide mechanism provides a convenient way to direct the rotation of the helix. A further advantage of the electrode tip is the provided mechanical stop. The mechanical stop aids in preventing over-retraction of the helix during the installation or removal of the electrode tip.

The electrodes are attached to the endocardium so that the electrical signals received from the heart are better than with floating, unattached electrodes. In addition, the active fixation electrodes can be placed into a recess so that mechanisms, such as a helical hook, used to attach the electrode to the wall of the heart will not catch undesired tissue. A further advantage is that only one lead needs to be placed into the patient to do both sensing and pacing of all types. The lead can also be shaped to facilitate placement of the lead.

A further advantage is that the bi-polar single pass lead allows for two chambers of the heart to be paced and/or sensed, while only one lead is implanted within the patient. This assists in preventing added stress and expense for the patient. In addition, the active fixation element will not hook nor snag tissue when it is retracted within the lead. The active fixation element does not require the use of a stylet, since the terminal pins are used to extend and retract the active fixation element. An additional benefit is that only one lead is placed into the patient for both sensing and pacing, thereby eliminating the need for placement of the second lead.

Yet another advantage is that the extendable portion of the lead is mechanically isolated from the main lead body so that the helical screw or hook can turn independently of the lead body. In other words, the body of the lead does not need to be turned to affix the helical screw to the heart.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 7 is a cross-section view illustrating a portion of a single-pass lead constructed in accordance with yet another embodiment of the present invention.

FIG. 8 is a cross-section view illustrating a portion of a single-pass lead constructed in accordance with one embodiment of the present invention.

FIG. 17A is a side view of a single-pass endocardial lead for sensing and electrically stimulating the heart constructed in accordance with one embodiment of the present invention.

FIG. 17B is a side view of stylet for use with the endocardial lead.

FIG. 43A is a cross-sectional view of an electrode tip of a lead for monitoring and stimulating the heart constructed in accordance with one embodiment of the present invention.

FIG. 43B is an end view of the electrode tip of the lead shown in FIG. 43A.

FIG. 45A is a cross-sectional view of an electrode tip of a lead for monitoring and stimulating the heart constructed in accordance with one embodiment of the present invention FIG. 45B is an end view of the electrode tip of the lead shown in FIG. 45A.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
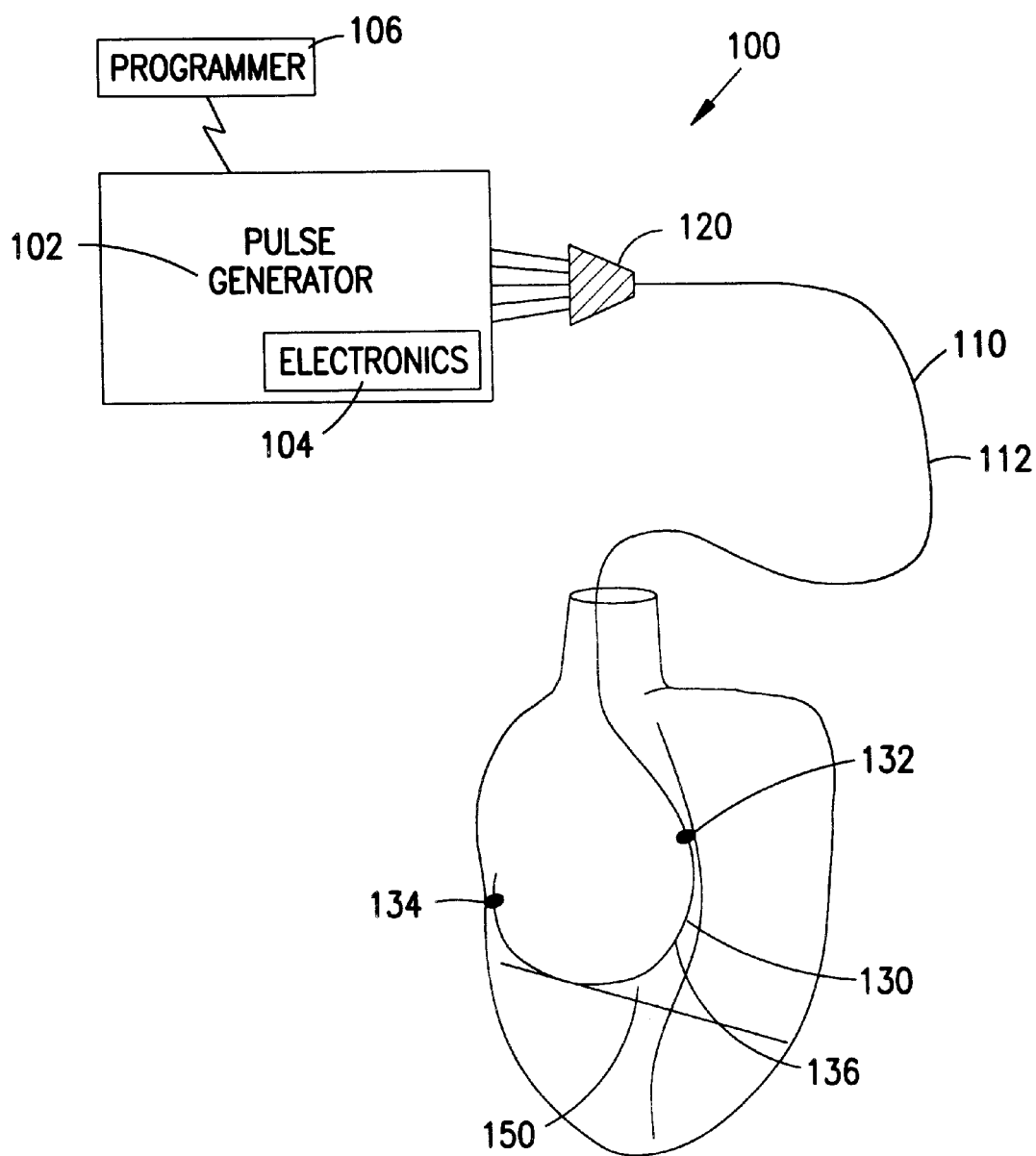
FIG. 1 is a schematic view of a single-pass lead with electrodes for pacing at multiple sites within a single chamber of the heart.

FIG. 1 illustrates a schematic view of a system 100 for delivering electrical pulses or signals to stimulate and/or pace the heart. The system for delivering pulses 100 includes a pulse generator 102 and a lead 110, where the lead 110 includes a connector end or connector terminal 120 and extends to a distal end 130. The distal end 130 of the lead 110 includes at least two electrodes 132 and 134, which comprise either unipolar or bipolar type electrodes. For bipolar type electrodes, the electrode 132 would be part of a bipolar set including two electrodes. Similarly, the electrode 134, if bipolar, would be part of a set.

The lead 110 includes a lead body 112 which, in one embodiment, is comprised of a tubing material formed of a biocompatible polymer suitable for implementation within the human body. Preferably, the tubing is made from a silicon rubber type polymer. The lead body 110 includes at least one lumen (not shown) which carries each electrical conductor from the connector terminal 120 to the electrodes 132 and 134. The electrical conductors carry current and pulses between the pulse generator 102 and the electrodes 132 and 134 located in the distal end 130 of the lead 110.

The pulse generator 102 includes a source of power as well as an electronic circuitry portion 104. The pulse generator is a battery-powered device which generates a series of timed electrical discharges or pulses used to initiate depolarization of excitable cardiac tissue. The pulses are delivered to the cardiac tissue and operate as an artificial pulse formation source when used to pace the heart. The pulse generator is generally implanted into a subcutaneous pocket made in the wall of the chest. Alternatively, the pulse generator 102 can be placed in a subcutaneous pocket made in the abdomen, or other locations.

The lead 110 is connected to the pulse generator 102 by the connector terminal 120. The lead 110 travels from the pulse generator 102 into a major vein, and the distal end 130 of the lead is placed inside the heart. The lead 110 is placed underneath the skin and travels to the shoulder and neck where it enters a major vein such as the subclavian vein. The distal end 130 of the lead 110 is placed directly within the endocardium. In one embodiment, the lead 110 will be actively or passively affixed to the endocardial wall of a chamber of the heart, as will be further described below.

As can be seen in FIG. 1, the distal end 130 of the lead 110 is curved, where the electrodes 132, 134 are disposed along the curve 136. The curve 136 is sized and positioned to allow the electrodes 132 and 134 to be positioned within one chamber of the heart. In FIG. 1, the chamber selected for implantation is the right atrium 150. The lead 110 will include a lumen into which a stylet may be placed. The stylet is basically a wire that straightens out the lead while it is being placed within the heart. By removing the stylet, the lead will take on its natural or manufactured shape, which in this case, is a curved distal end 130. The curve within the distal end 130 of the lead 110 has a small enough radius such that it fits within the right atrium 150 of the heart.

The electronics 104 associated with the pulse generator 102 include a delay circuit which allows the pulse delivered to one of the electrodes 132 or 134 to be delayed with respect to the pulse delivered to the other of the electrodes. This delay can be either a delay of zero or it can be a delay that can be programmed to be any desired length of time. The delay portion of the electronics 104 typically will include a clock source. The clock source will produce a clocking pulse that can be used to produce the delay. In other words, if a delay of so many clocking signals equals the appropriate or selected delay, the pulse generator 102 and the electronics 104 will initially deliver a pulse to a first electrode, then the electronics will count the selected number of pulses from a clock signal and then deliver a pulse to the other of the electrodes 132 and 134.

Also shown in FIG. 1 is a programmer 106. The programmer is typically an external-type programmer that can be used to program many of the parameters of the electronics 104 and other parameters of the pulse generator 102. One of the parameters that can be programmed includes the length of delay between the pulse to the electrode 132 and the pulse to the electrode 134. It should be noted that the length of delay can also be set so that it's nonexistent. In other words, if a delay of zero is used, the pulse generator 102 and the electronics associated with the pulse generator 104 will send pacing pulses to the electrode 132 and the electrode 134 at substantially the same time. The programmer can also be an external handheld-type programmer which a patient might be able to use. The other type of programmer might be one that a physician would have in his or her office which can be used to program various parameters associated with the pulses produced by the pulse generator. The programmer 106 will typically have a feature which will allow readout of the status of the pulse generator.

Figure 2:
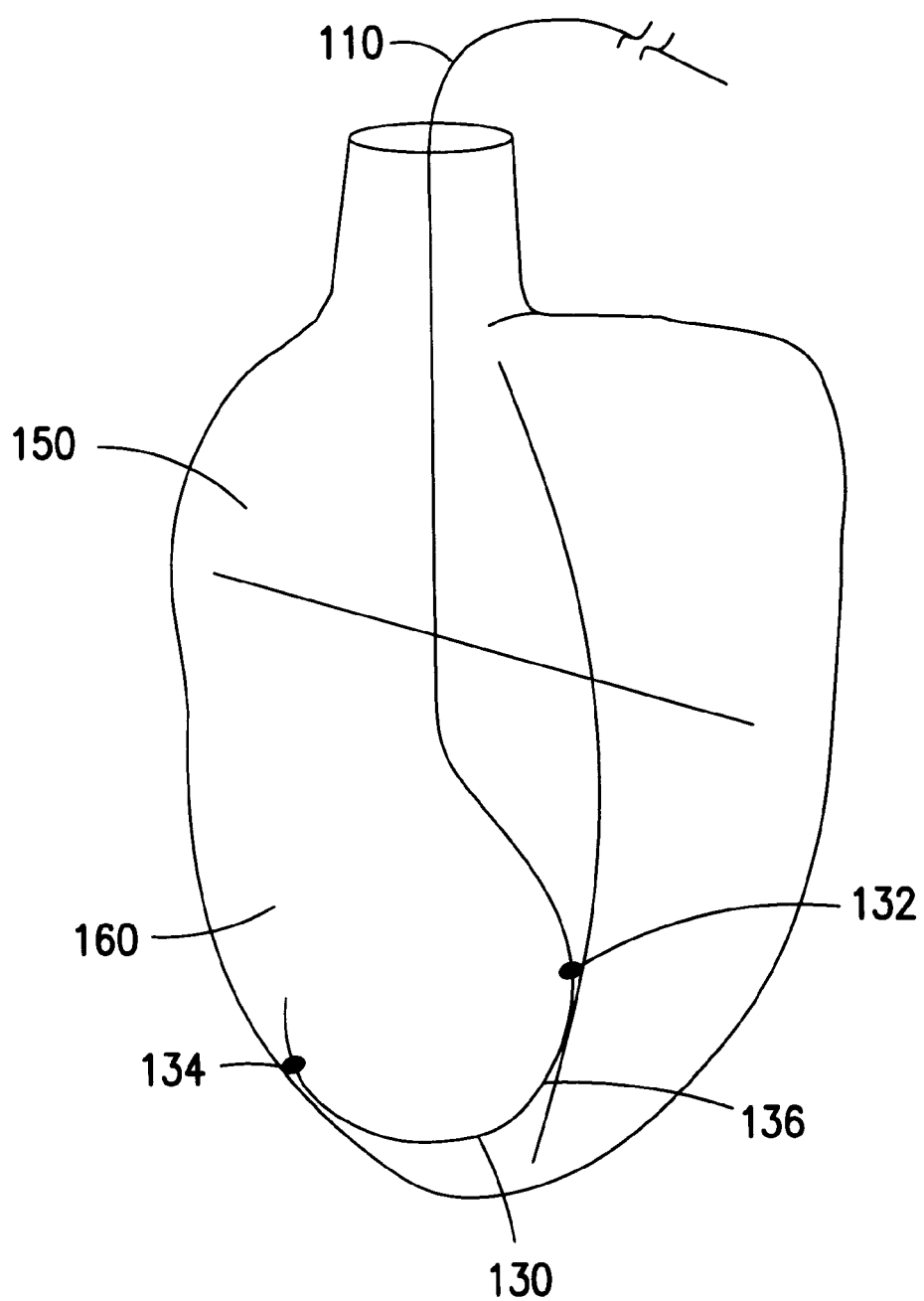
FIG. 2 is a schematic view of a single-pass lead with electrodes for pacing at multiple sites within a single chamber of the heart, positioned within the right ventricle of the heart.

FIG. 2 is a schematic of a single-pass endocardial lead for electrically stimulating multiple sites within a single chamber of the heart which is positioned within the right ventricle of the heart, where the lead 110 is shown as having a distal end 130. The distal end 130 features includes a first electrode 132 and a second electrode 134. In FIG. 2, the distal end 130 of the lead body 110 passes through the right atrium and is positioned within the right ventricle 160 of the heart. Again, as before, the electrodes 132 and 134 may be unipolar or may be bipolar. In the instance when each of the electrodes 132 and 134 are bipolar, there is an additional electrode associated with each of the electrodes 132 and 134. Alternatively, in another embodiment, one of the electrodes 132 is unipolar and one of the electrodes 134 is bipolar.

The electrodes 134 and 132 are positioned along the curve 136 in the distal end 130 so that electrical stimulation or pulse generation can be delivered to two sites within a single chamber of the heart, namely, the right ventricle 160. The curve 136 is sized and positioned to be received within the ventricle, where the electrodes 132 and 134 are in contact with the wall of the heart, as shown. The electrodes 132 and 134 are attached to the endocardial wall of the heart with either passive fixation or active fixation, as will be further described below. The shape of the curve 136 associated with the distal end may be varied to achieve a selected placement of the electrodes 134 and 132 within the right ventricle of the heart. In addition, the distance between the first electrode 132 and second electrode 134 can also be changed for various applications for multi-site pacing within the right ventricle. The pulse generator and electronics as well as the connector end or terminal end 120 of the lead 110 and the programmer 106, are all the same in FIG. 1 as in FIG. 2 and, therefore, were not shown here.

Figure 3:
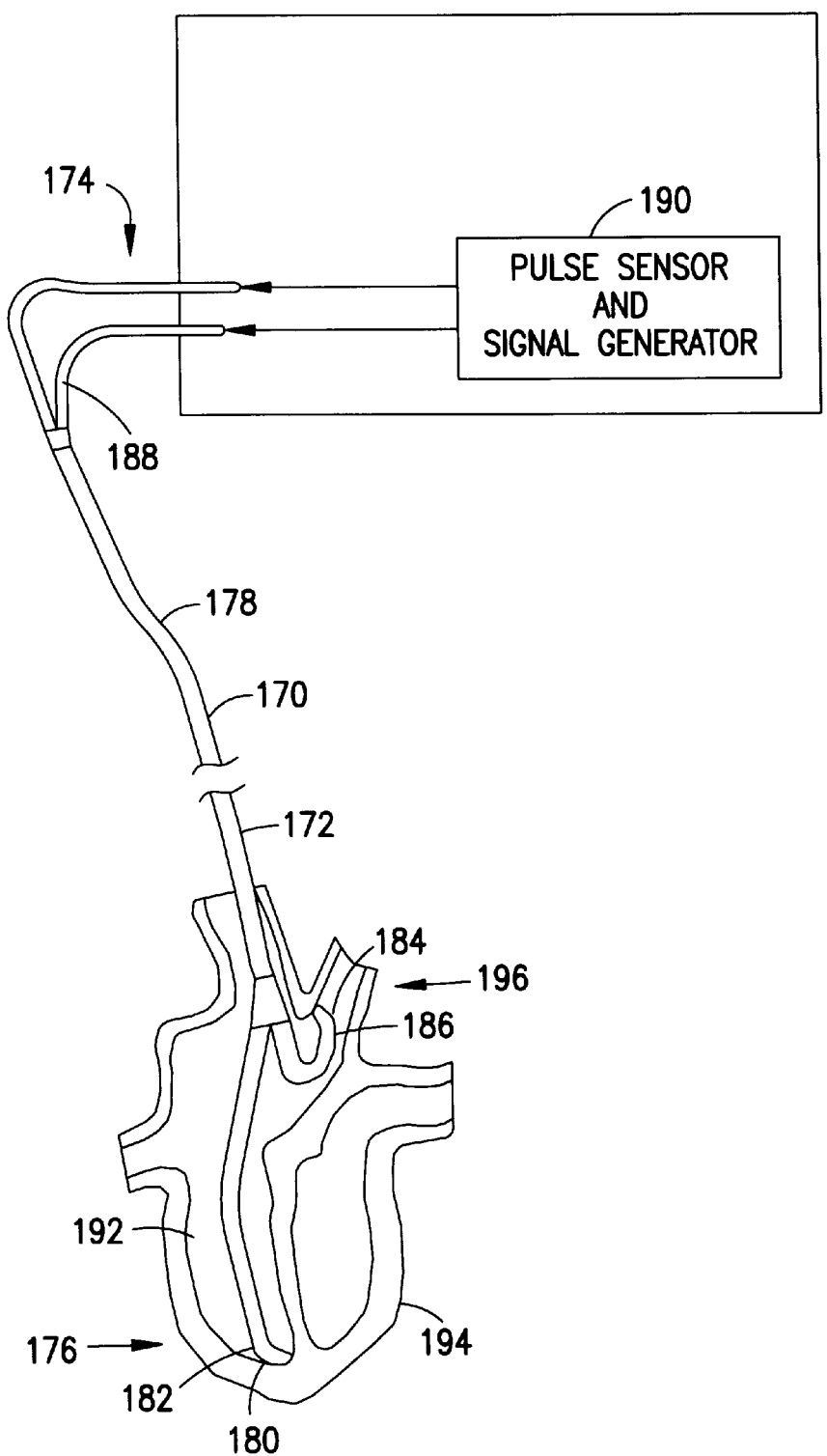
FIG. 3 is a block diagram illustrating a system for delivering signals to the heart constructed in accordance with one embodiment of the present invention.

FIG. 3 illustrates another embodiment of the present invention, showing a lead 170 adapted for delivering electrical pulses to stimulate the heart. The lead 170 has a lead body 172 extending from a proximal end 174, which is adapted to connect with equipment which supplies electrical pulses, to a distal end 176 which is adapted to be inserted into the heart. The lead body 172 includes an intermediate portion 178 which includes quad-lumen tubing as will be further discussed below. Proximate to the distal end 176 is a first electrode tip 180 including a first electrode assembly 182. A second electrode tip 184 is also provided, as discussed below, which includes a second electrode assembly 186.

Proximate to the proximal end 174 of the lead 170 are connector terminals 188. The connector terminals 188 electrically connect the various electrodes and conductors within the lead 170 to a pulse generator and signal sensor 190. The pulse sensor and generator 190 contains electronics to sense various electrical signals of the heart and also produce current pulses for delivery to the heart, depending on the type of lead 170 used. The pulse sensor and generator 190 also contains electronics and software necessary to detect certain types of arrhythmias and to correct for them. The lead terminal connector 188 provides for the electrical connection between the lead 170 and the pulse generator 190.

Figure 4:
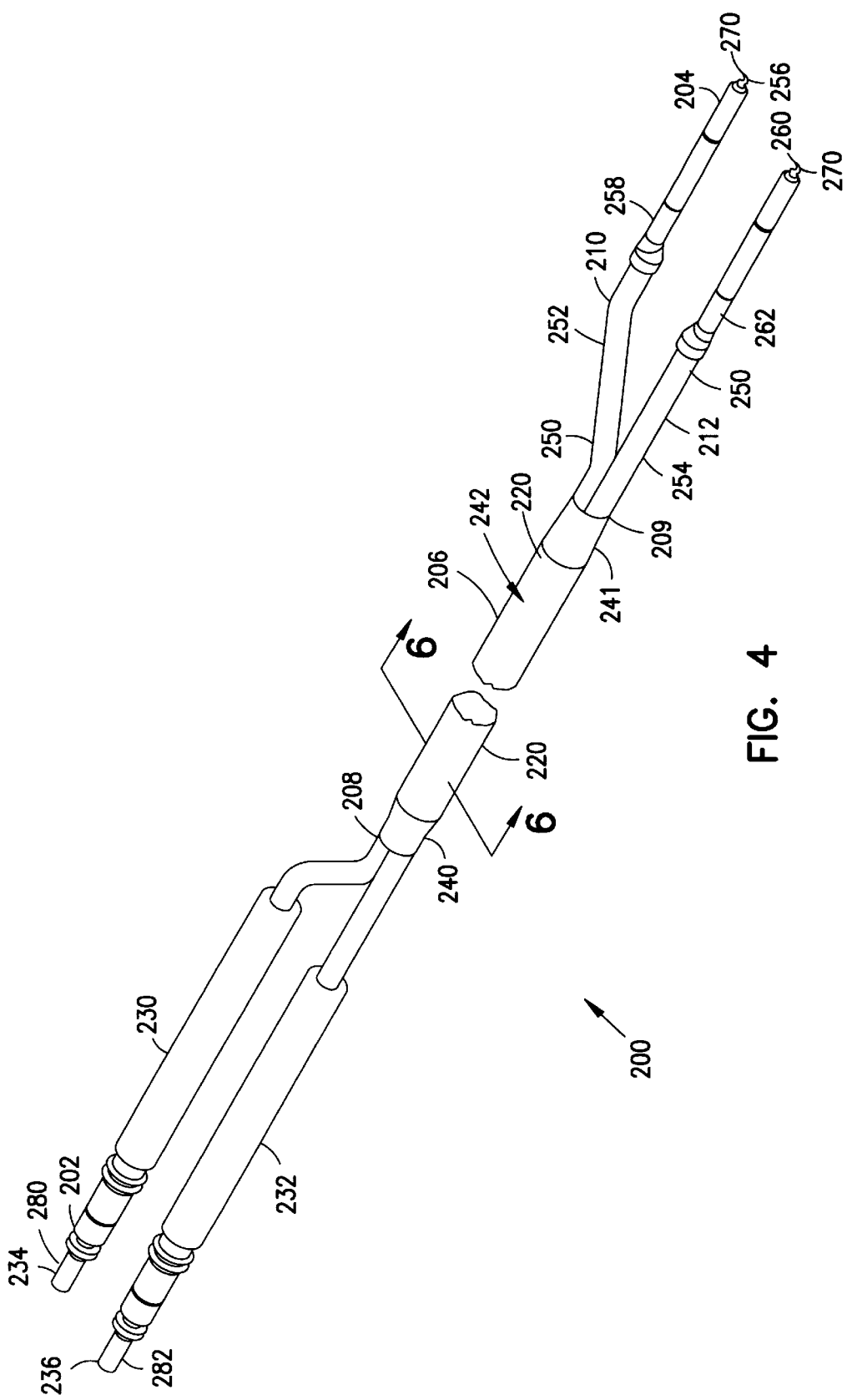
FIG. 4 is a first perspective view illustrating a single-pass lead constructed in accordance with one embodiment of the present invention.

To implant the lead 170 within a patient, a single sheath can be used for the single electrode 170 to implant the lead 170 within the heart, which prevents unnecessary trauma to the patient. The first electrode assembly 182 is advanced into the ventricular portion 192 of the heart 194. The first electrode assembly 182 is secured to the wall of the heart 194 using either passive or active fixation. In one embodiment, the active fixation elements are advanced using the terminal pins (FIG. 4). In another embodiment, the active fixation elements are advanced using a stylet, as discussed further below.

The second electrode assembly 186 is advanced, in one embodiment, into the atrium portion 196 of the heart 194 using a straight stylet (not shown). To secure the second electrode assembly 186 into the atrium, the straight stylet is removed and a J-shaped stylet (not shown) is insert into the second electrode assembly 186 and the second electrode assembly 186 takes on the J-shape. Alternatively, the second electrode assembly 186 is placed within the atrium portion 196 using a J-shaped lead, as shown and discussed below in FIGS. 11 and 12. Similar to the first electrode assembly, the second electrode assembly 186 is secured to the heart 194 using either passive or active fixation.

FIG. 4 illustrates the lead of FIG. 3 in greater detail. The lead 200 extends from a proximal end 202 to a distal end 204 and includes a first and second connector terminal 280, 282 near the proximal end 202. The lead 200 also includes a lead body 220, a first electrode assembly 210, and a second electrode assembly 212, as will be further described below. The connector terminals 280, 282 electrically connect the various electrodes and conductors with the lead body to a pulse sensor and generator 190 (FIG. 3). The pulse sensor and generator 190 (FIG. 3) contain electronics to sense various pulses of the heart and also produce pulsing signals for delivery to the heart. The pulse sensor and generator 190 also contain electronics and software necessary to detect certain types of arrhythmias and to correct for them. Physicians are able to program the pulse sensor and generator to correct a particular arrhythmia that the patient may have. Numerous types of connector terminals which connect to a pulse sensing and generating unit can be used. In one embodiment, the connector terminals 280, 282 are designed to conform with International Standards.

The lead body 220, in one embodiment, is formed from a polymer biocompatible material, and can include tubing made from a silicone rubber polymer. The lead body 220 extends from the proximal end 202 of the lead 200 to the distal end 204 of the lead 200, and has an intermediate portion 206 therebetween. Near the proximal end 202 of the lead body 220, the lead body 220 has at least two IS1 terminal legs, including a first terminal leg 230 and a second terminal leg 232.

At the proximal end 202 of the first terminal leg 230 and the second terminal leg 232 are terminal pins 234, 236 which can be operatively coupled with a pulse sensor and signal generator 190, as discussed above. In one embodiment, the terminal pins 234, 236 are used to rotate the active fixation device, discussed further below. In another embodiment, a stylet driven mechanism is used to rotate the active fixation device. The first terminal leg 230 and the second terminal leg 232 extend from the terminal pins 234, 236 of the proximal end 202 of the lead 200 to the intermediate portion 206 of the lead 200, where the first terminal leg 230 and the second terminal leg 232 are coupled with the intermediate portion 206 at a proximal bifurcation point 208. In one embodiment, the first terminal leg 230 and the second terminal leg 232 are coupled with the intermediate portion 206 with a yoke 240 which operates as a strain relief. The yoke 240, in one embodiment, comprises a sheath for covering at least portions of the first and second terminal legs 230, 232 and the intermediate portion 206, where the sheath can be attached using medical adhesive or other attachment methods. In another embodiment, the yoke 240 is over-molded encompassing the intermediate portion 206 and the first and second terminal legs 230, 232.

Figure 5:
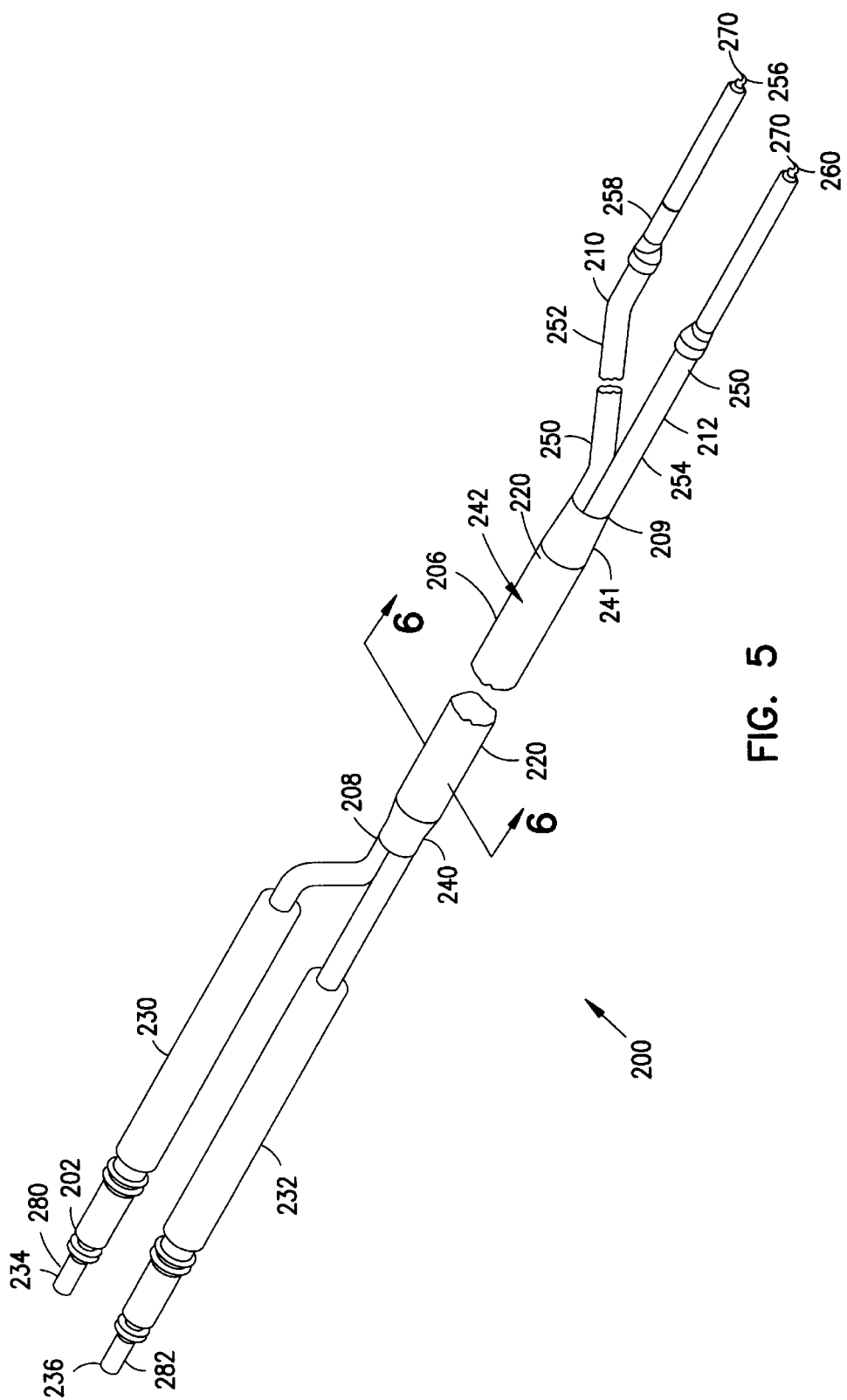
FIG. 5 is a second perspective view illustrating a single-pass lead constructed in accordance with one embodiment of the present invention.
Figure 6:
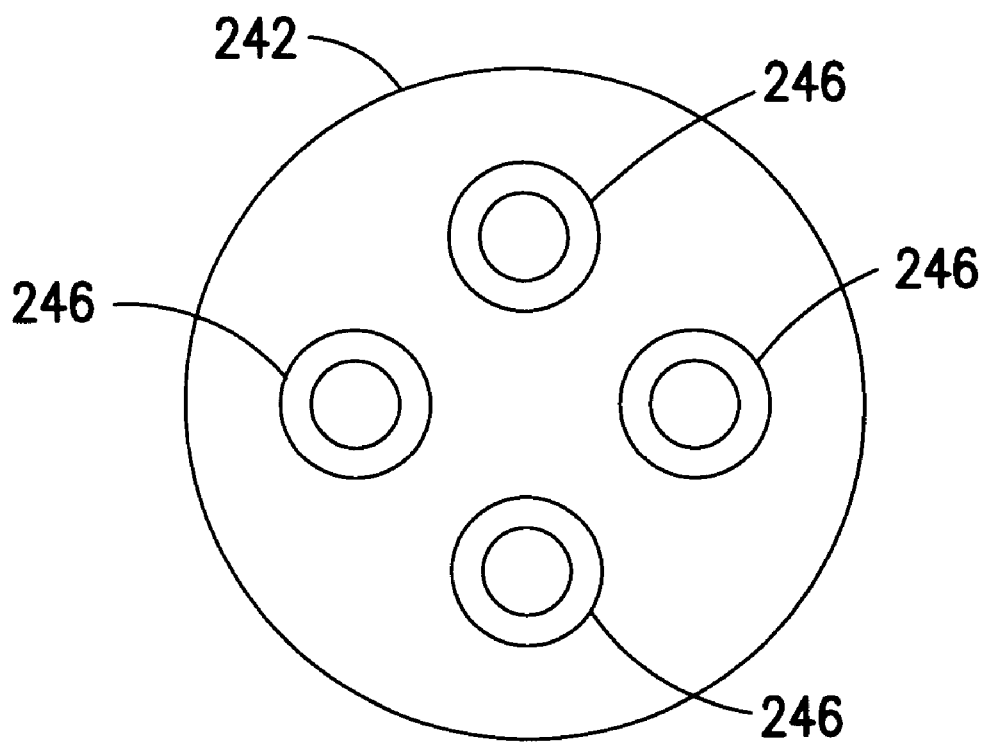
FIG. 6 is a cross-section view taken along 6—6 of FIG. 4 illustrating a single-pass lead constructed in accordance with another embodiment of the present invention.

The intermediate portion 206 of the lead body 220, as shown in FIG. 6, is comprised of quad-lumen tubing 242, which in one embodiment comprises PTFE insulation. Disposed within each lumen of the quad-lumen tubing 242 is a conductor 246, consisting of either a cable or a coil. Referring again to FIGS. 4 and 5, the intermediate portion 206 extends from the proximal bifurcation point 208 to a distal bifurcation point 209. At the distal bifurcation point 209, in one embodiment, the intermediate portion 206 transitions into two bi-lumen tubes 250, including a first electrode leg 252 and a second electrode leg 254. The first electrode leg 252, in one embodiment, is shorter in length than the second electrode leg 254, where the first electrode leg 252 is for implantation into an atrium (not shown) and the second electrode leg 254 is for implantation within the ventricle (not shown). In another embodiment, the first electrode leg 252 and the second electrode leg 254 are coupled with the intermediate portion 206 with a yoke 241, similar to the yoke 240 discussed above. The first electrode leg 252 and the second electrode leg 254 each extend to the first electrode assembly 210 and the second electrode assembly 212, respectively.

In one embodiment, as shown in FIG. 4, the first electrode assembly 210 and the second electrode assembly 212 are both bipolar. In another embodiment, as shown in FIG. 5, the first electrode assembly 210 is bipolar and the second electrode assembly 212 is unipolar. In yet another embodiment, similar to FIG. 5, the first electrode assembly 210 is unipolar and the second electrode assembly 212 is bipolar. To form a unipolar electrode assembly, only a single conductor, discussed further below, is provided within the electrode assembly, and a single electrode is provided. The electrode, for either the bipolar or unipolar embodiments of the first and second electrode assemblies 210, 212, comprises a singular electrode or a combination of electrodes of the following: a tip electrode, a ring electrode, a defibrillator coil, or their equivalents. The various electrodes can be used for pacing, sensing, defibrillating, or a combination of the same.

In another embodiment, a first conductor set is disposed within the first electrode leg 252 and comprises a coil and a cable which terminate in a first pacing tip 256 and a first pacing ring 258, respectively. Similarly, as shown in FIG. 4, a second conductor set is disposed within the second electrode leg 254 and comprises a coil and a cable which terminate in a second pacing tip 260 and a second pacing ring 262, respectively. For the embodiment shown in FIG. 5, the second conductor set comprises only a second pacing tip 260, thereby forming a unipolar leg.

Figure 9:
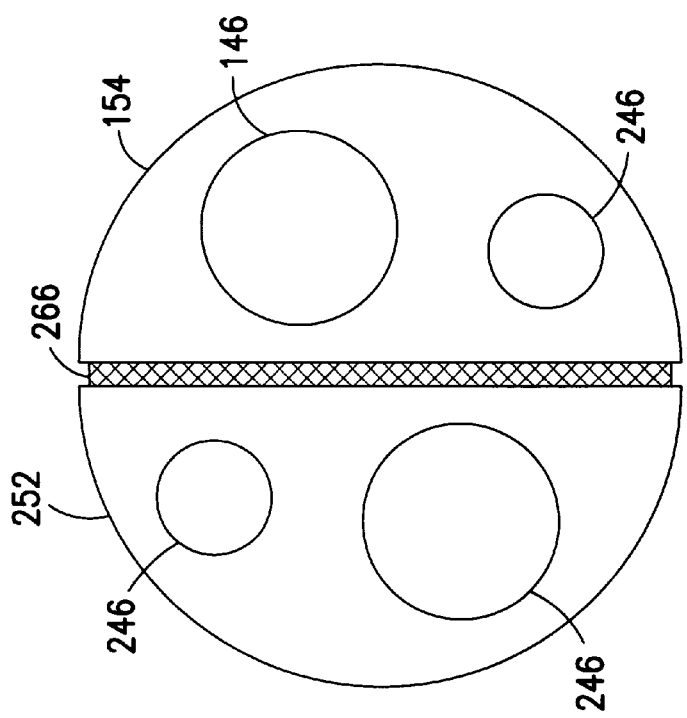
FIG. 9 is a cross-section view illustrating a portion of a single-pass lead constructed in accordance with one embodiment of the present invention.

The first electrode leg 252, in one embodiment, has a semi-circular cross-section, as shown in FIG. 7. Similarly, the second electrode leg 254, in another configuration, also has a semi-circular cross-section. When placed adjacent to one another, the first electrode leg 252 and the second electrode leg 254 form a circular cross-section, as shown in FIG. 9. In one configuration, medical adhesive or other equivalents 266, including dissolvable substances such as mannitol, are disposed between the first electrode leg 252 and the second electrode leg 254 to aid in the installation of the lead 200 within a patient.

Figure 10:
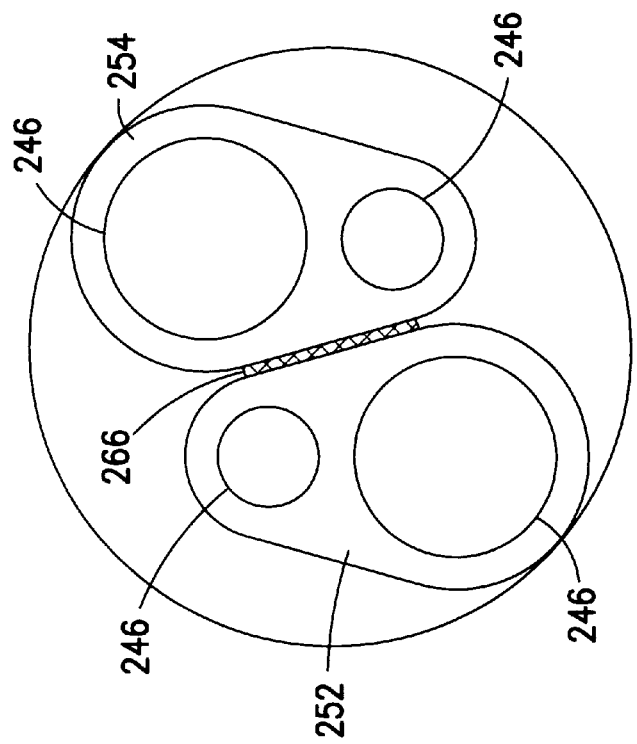
FIG. 10 is a cross-section view illustrating a portion of a single-pass lead constructed in accordance with one embodiment of the present invention.

Alternatively, the first electrode leg 252 has an elliptical cross-section, as shown in FIG. 8. Similarly, the second electrode leg 254 has an elliptical cross-section. When placed adjacent to one another, the first electrode leg 252 and the second electrode leg 254 easily fit together, as shown in FIG. 10. In another embodiment, medical adhesive or other equivalents 266, including dissolvable substances such as mannitol, are disposed between the first electrode leg 252 and the second electrode leg 254, as shown in FIG. 10, to assist in the installation of the lead 200 within a patient. The cross-section of the first and second electrode legs 252, 254 are not limited to the above and can have other cross-sections.

Figure 11:
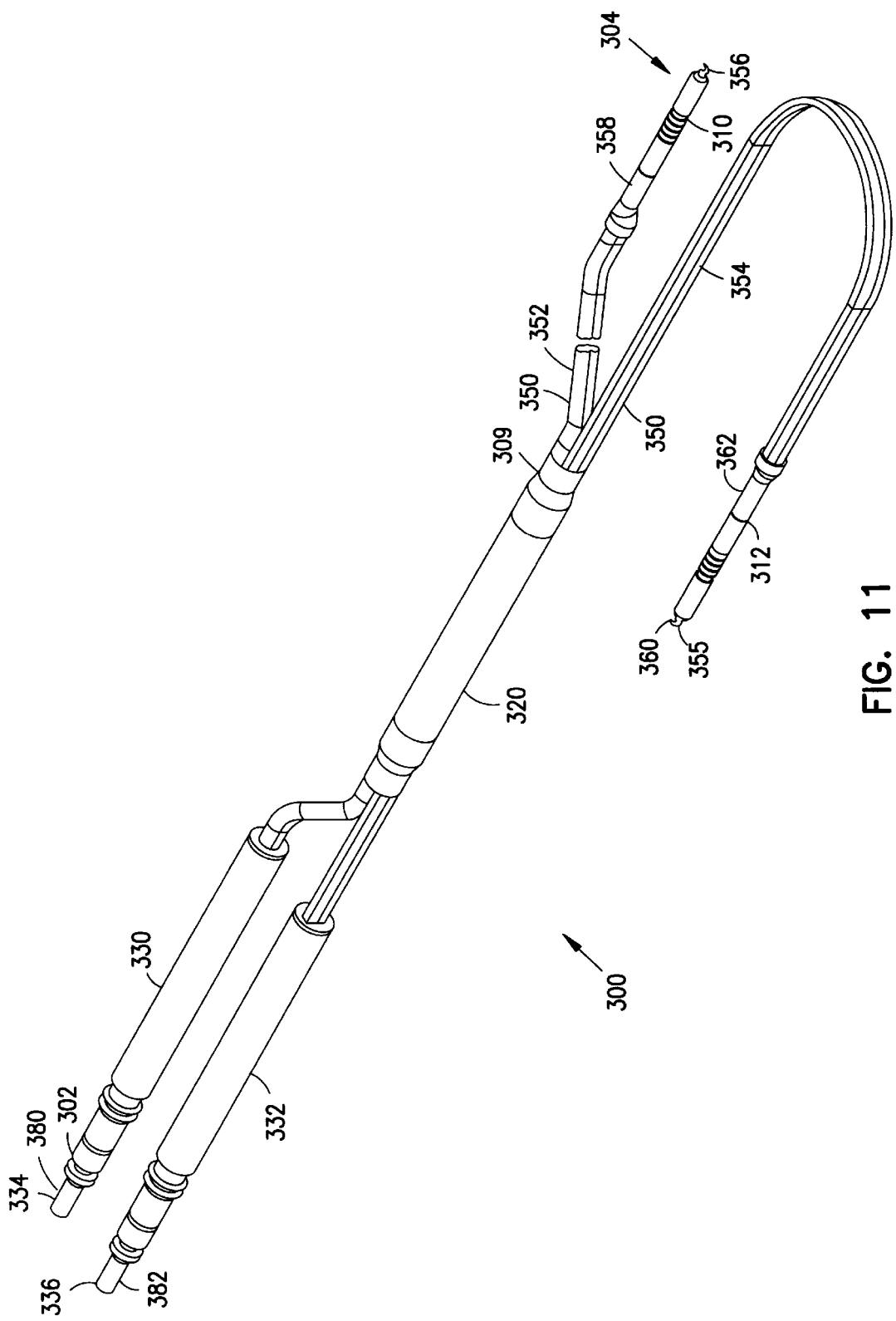
FIG. 11 is a perspective view illustrating a single-pass lead constructed in accordance with one embodiment of the present invention.

FIG. 11 illustrates another embodiment showing a lead 300. The lead 300 extends from a proximal end 302 to a distal end 304 and comprises a first and second connector terminal 380, 382 near the proximal end 302. The lead 300 also includes a lead body 320, a first electrode assembly 310, and a second electrode assembly 312. Near the proximal end 302 of the lead body 320, the lead body 320 has at least two IS1 terminal legs, including a first terminal leg 330 and a second terminal leg 332.

Figure 12:
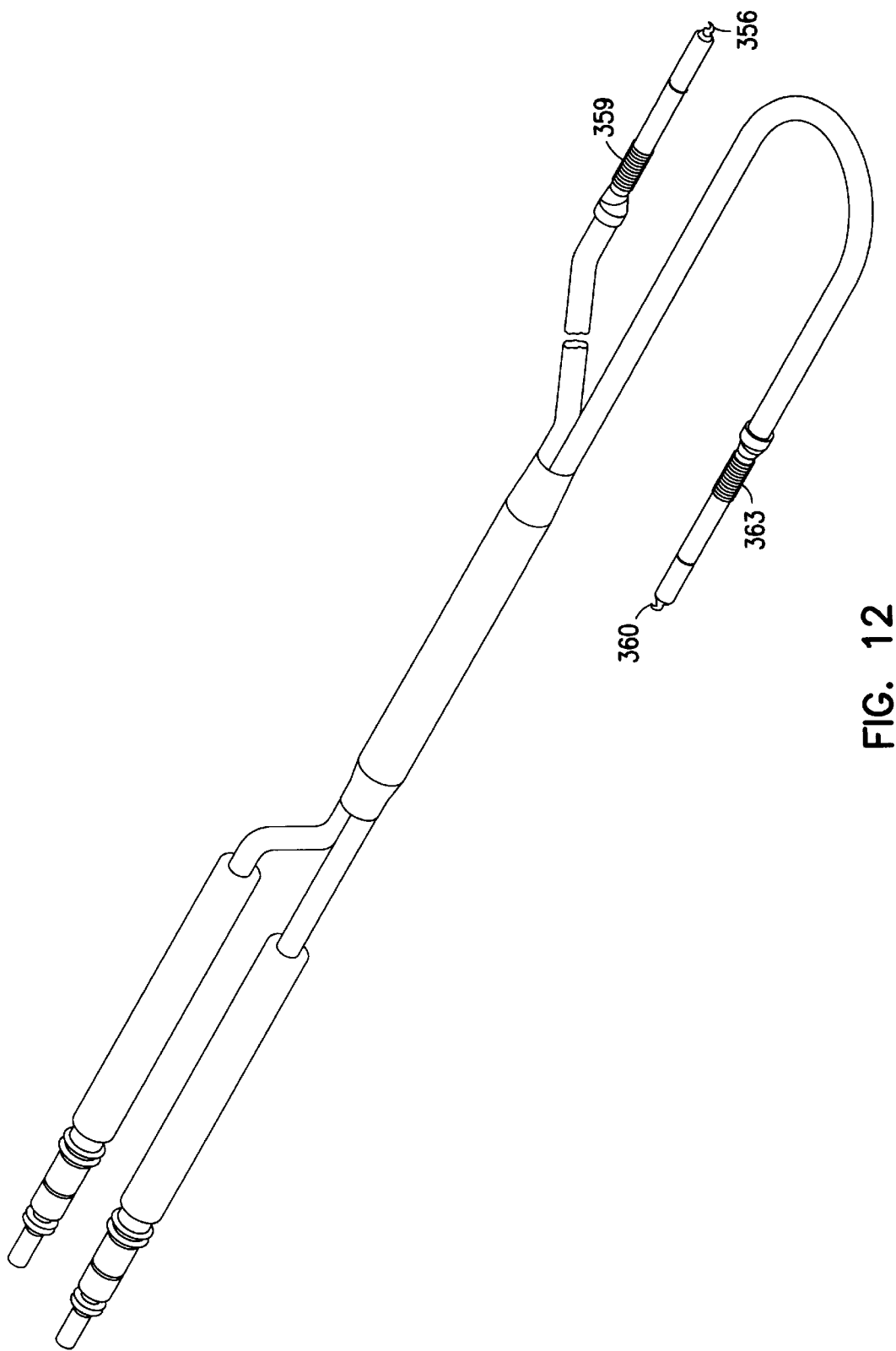
FIG. 12 is a perspective view illustrating a single-pass lead constructed in accordance with one embodiment of the present invention.

At a distal bifurcation point 309, an intermediate portion 306 of the lead body 320 transitions into two bit-lumen tubes 350, including a first electrode leg 352 and a second electrode leg 354. The first electrode leg 352 and the second electrode leg 354 each extend to the first electrode assembly 310 and the second electrode assembly 312, respectively. A first conductor set is disposed within the first electrode leg 352 and comprises, in one embodiment, a coil and a cable which terminate in a first pacing tip 356 and a first pacing ring 358, respectively. Similarly, a second conductor set is disposed within the second electrode leg 354 and comprises, in another embodiment, a coil and a cable which terminate in a second pacing tip 360 and a second pacing ring 362, respectively. In another embodiment, as shown in FIG. 12, the first conductor set and the second conductor set disposed within the first electrode leg 352 and the second electrode leg 354, respectively, terminate in a first pacing tip 356 and a first defibrillator electrode 359 second pacing tip 360 and a second defibrillator electrode 363.

The first electrode leg 352 and the second electrode leg 354, in one embodiment, comprise bipolar lead legs. In another embodiment, the first electrode leg 352 is unipolar and the second electrode leg 354 is bipolar (See FIG. 5). In yet another embodiment, the first electrode leg 352 is bipolar and the second electrode leg 354 is unipolar. The electrode, for either the bipolar or unipolar embodiments of the first and second electrode assemblies 310, 312, comprises a tip electrode, a ring electrode, a defibrillator coil, or their equivalents. The various electrodes can be interchanged and used for pacing, sensing, defibrillating, or a combination of the same.

The second electrode leg 354, in one embodiment, has a J-shape, which can have either passive or active fixation, as will be further discussed below. Using a straight stylet (not shown) to straighten the electrode leg 354 prior to implant, the second electrode leg 354 is positioned within the right atrium of the heart. As the stylet (not shown) is removed, the second electrode leg 354 re-assumes the J-shape and becomes positioned within the atrium of the heart. If a passive configuration is used, as further discussed below (for example, FIG. 36), the distal end 355 of the second electrode leg 354 becomes embedded within the wall of the heart as tissue in-growth begins. If an active fixation configuration is used, the distal end 355 of the second electrode leg 354 is positioned adjacent the wall of the heart. The fixation helix is advanced so that it screws into the wall of the heart and the second electrode leg 312 is engaged. The discussions of leads for multi-site pacing and/or passive and active fixation devices in related co-pending applications entitled SINGLE PASS LEAD AND SYSTEM WITH ACTIVE AND PASSIVE FIXATION ELEMENTS, Ser. No. 09/121,005, and Attorney Docket No. 279.081US1 and SINGLE PASS ENDOCARDIAL LEAD FOR MULTI-SITE ATRIAL PACING, Ser. No. 09/121,019, and Attorney Docket No. 279.079US1 are hereby incorporated by reference in their entirety.

Figure 13:
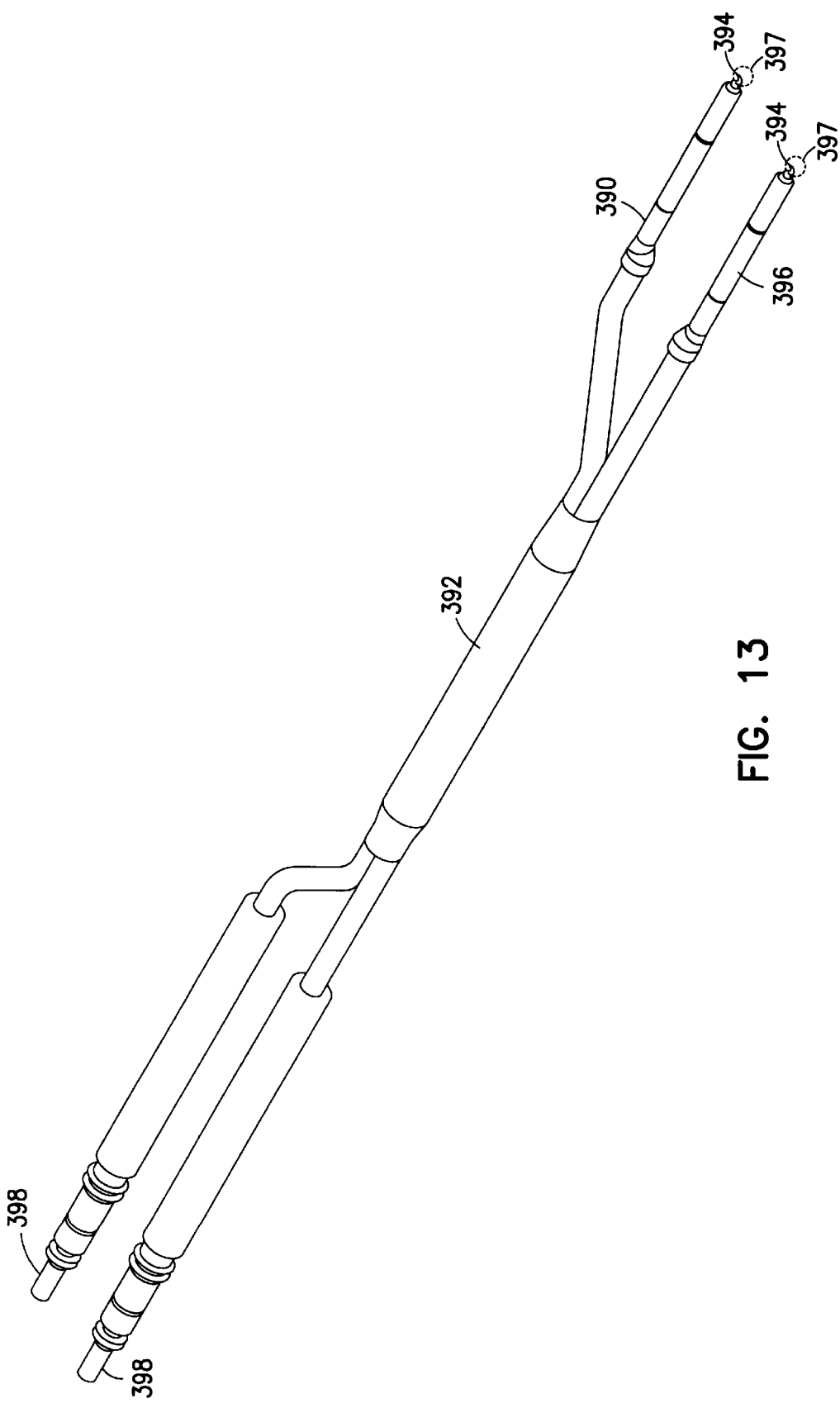
FIG. 13 is a perspective view illustrating a single-pass lead constructed in accordance with another embodiment of the present invention.

FIG. 13 shows another embodiment of the invention. In this configuration, the atrial lead 390 and/or the ventricle lead 396 each have an active fixation element 394, as further described below, for fixating the leads 390, 396 to the endocardial wall of a heart. The active fixation element 394 is rotatable by terminal pins 398, and the active fixation element 394 is not retractable. Alternatively, the active fixation element 394 can be rotated using other manners, for example, a stylet. To protect the patient during implantation or to prevent snagging of the fixation element 394, the active fixation element 394 of the atrial lead 390 and/or the ventricle lead 396 is covered with a dissolvable coating 397, such as mannitol. The dissolvable coating 397 remains intact during insertion of the leads 390, 396 through the subclavian vein and into the heart. The dissolvable coating 397 prevents the active fixation element 394 from catching tissue in the vein during insertion. Once implanted, the coating 397 dissolves to expose active fixation element 394 and allow it to be turned into the atrial wall of the heart. The dissolvable coating 397 is depicted by a dotted line enclosure around the active fixation element 394.

FIGS. 14–27 illustrate another embodiment of a lead coupled with a system and the heart, wherein a portion of the lead body is curved and at least one electrode is coupled with the curved portion 450 of the lead 400. The lead 400 and, more specifically, the distal end 430 of the lead 400 positioned within a heart 402. The heart 402 includes four chambers which are the right atrium 404, the right ventricle 405, the left ventricle 406 and the left atrium 407. Also shown in FIG. 14 is the superior vena cava 408.

The distal end 430 of the lead 400, in one embodiment, is positioned within the superior vena cava 408, the right atrium 404 and the right ventricle 405. The curved portion 450 of the lead 400 positions the atrial electrode 461 on the curved portion 450 or biased section closer to the wall of the heart 402 in the right atrium 404. This enhances electrical performance as electrode 461 will be closer to the portion of the heart 402, namely the right atrium 404, where the signal will pass. In addition, the electrode 461 is positioned closer to the wall of the right atrium 404 such that passive fixation can occur. If passive fixation is achieved, the distal end 430 of the lead 400 will be more stably fixed within the heart 402. Even if the passive fixation is not achieved, the electrode 161 will be biased closer to the wall of the right atrium 202 so as to enhance the electrical sensing capability of that electrode. In another embodiment, a plurality of tines 480 are coupled near the electrode 454. The plurality of tines 480 aid in positioning the distal end 430 in the right ventricle 405 at the time of lead insertion. At the time of lead implantation, the distal electrode 454 is generally positioned in the right ventricle. The tines 480 are used to engage tissue structures which line the endocardial surface of the ventricle 405 and then hold the lead 400 in place after it is implanted. Fibrous tissue grows over these tines 480 over time to produce an attachment to the wall of the heart in the right ventricle 405 and further secure the lead 400 within the heart 402.

Figure 14:
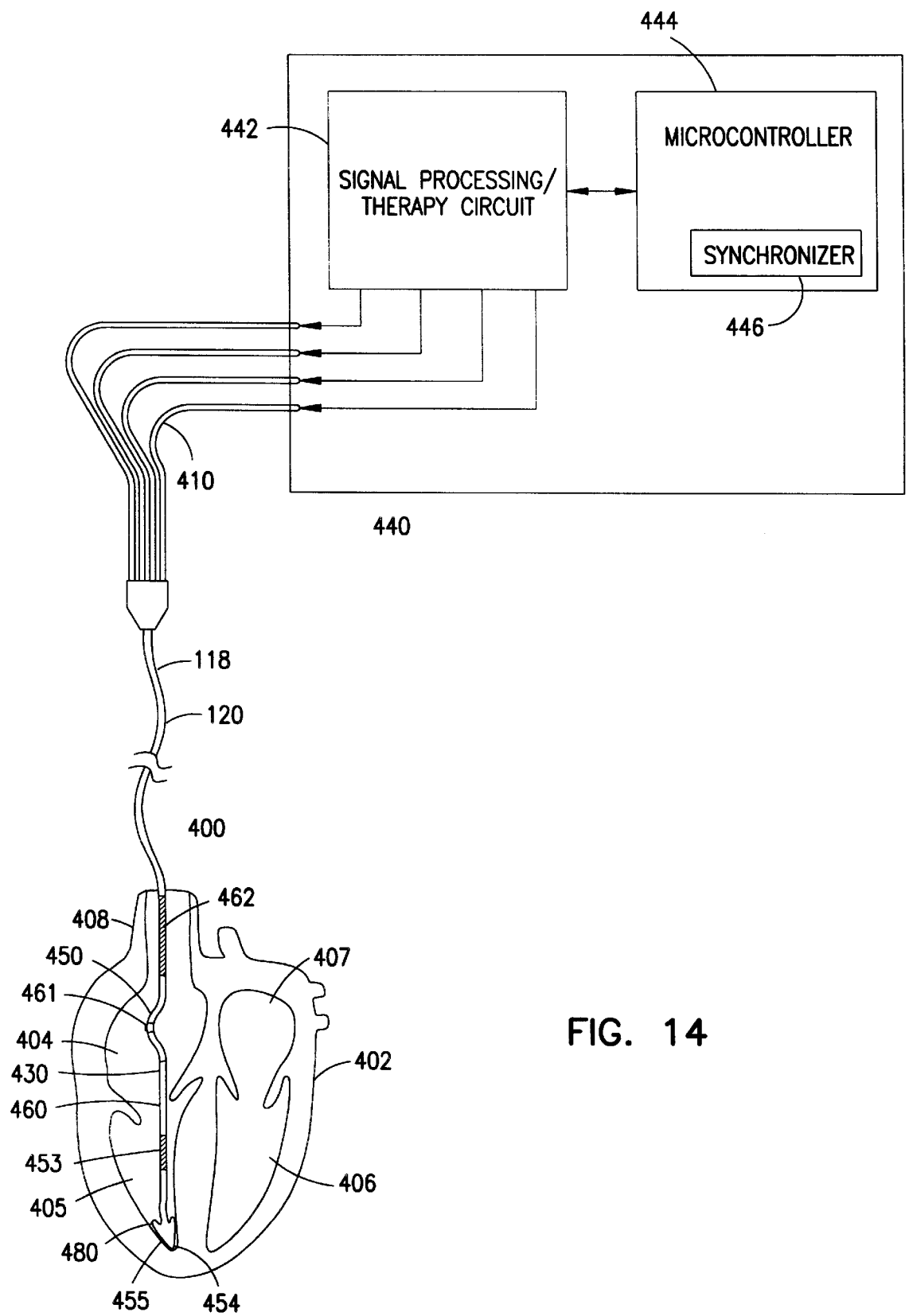
FIG. 14 is a side view of the single-pass endocardial lead for sensing and electrically stimulating the heart, positioned within the right ventricle and right atrium of the heart, constructed in accordance with one embodiment of the present invention.

FIG. 14 also shows the lead terminal connector 410 and its connection into the pulse generator 440. The lead terminal connector 410 makes electrical connection with a signal processing/therapy circuit 442 which in turn is electrically connected to a microcontroller 444. Within the microcontroller 444 is a synchronizer 446. The signal processing/therapy circuit 442 determines the type of therapy that should be delivered to the heart 402. The microcontroller 444 controls the delivery of the therapy to the heart 402 through the synchronizer 446. The synchronizer 446 times the delivery of the appropriate signal to the heart 402.

Figure 15A:
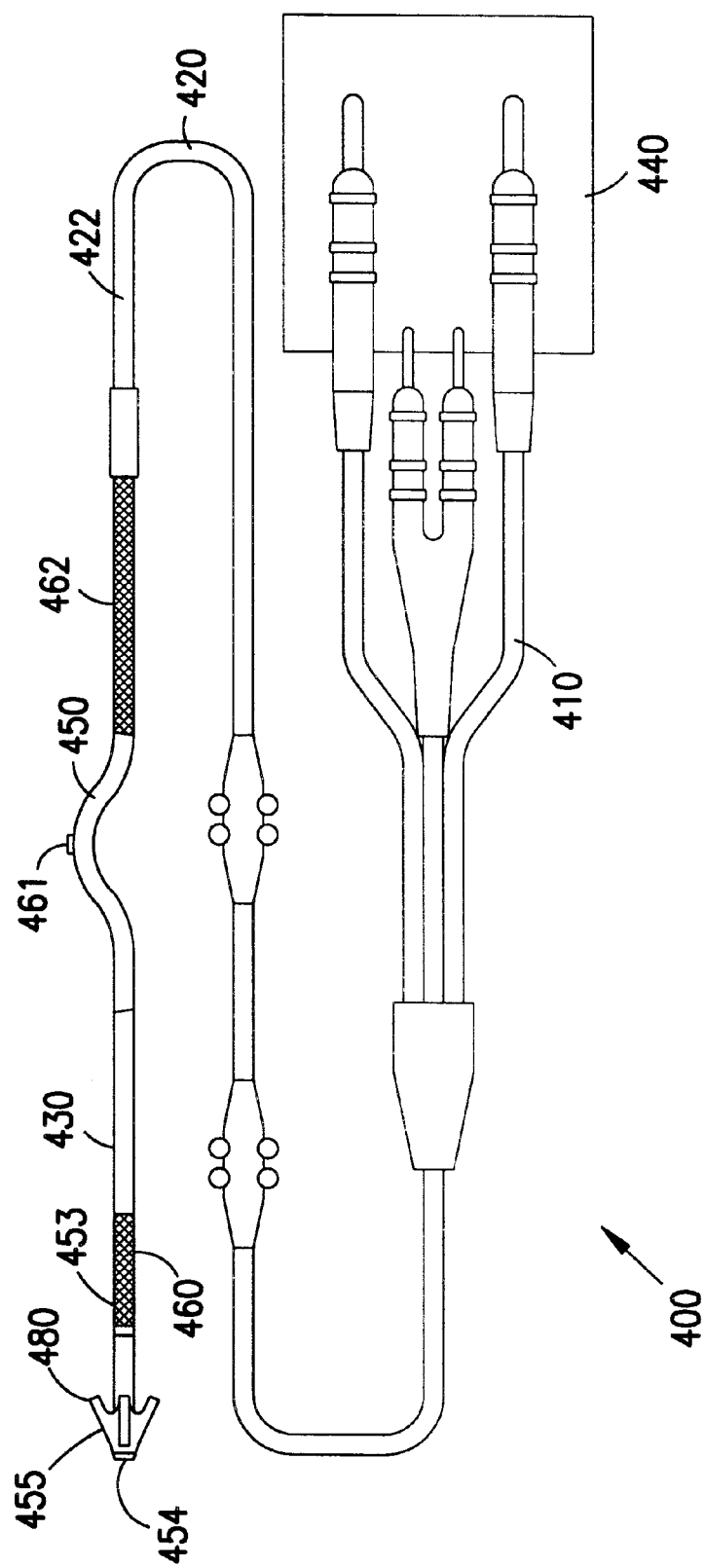
FIG. 15A is a side view of a single-pass lead for sensing and electrically stimulating the heart constructed in accordance with one embodiment of the present invention.

FIG. 15A shows the lead 400 in greater detail. The lead 400 includes a connector terminal 410, a distal end 430, and an intermediate portion 420 which interconnects the distal end 430 and the connector terminal 410, and include conductive wires (not shown) covered by a silicone rubber tubing which is biocompatible, to form the lead body 422. The connector terminal 410 electrically connects the various electrodes and conductors within the lead body 422 to the pulse generator 440 (discussed above). The distal end 430 is the portion of the lead 400 that includes electrodes and is positioned within the heart during implantation. The lead body 422 is a tubing material formed from a biocompatible polymer for implantation, and preferably tubing made from a silicone rubber polymer. The silicone rubber polymer tubing contains several electrical conductors (not shown). The electrical conductors are made of a highly conductive, highly corrosion resistant material.

After the lead 400 has been implanted, the distal end 430 of the lead body 422 is situated predominantly within the heart 402 (FIG. 14). The distal end 130 of the lead body 422 includes a curved or bias portion 450 and, in one embodiment, a straight portion 460. After implantation, the curved portion 450 of the electrode end 130, in one embodiment, will generally be located in the right atrium of the heart 402 (FIG. 14), and the straight portion 460 will be located in the right ventricle 405. It should be noted that the lead 400 could also be implanted within the left atrium 407 and the left ventricle 406 of the heart 402.

In one embodiment, the electrode end 130 of the lead 400 has four electrodes 453, 454, 461, and 462. Referring again to FIG. 14, two of the electrodes 461, 461 are located in the atrium 404, and two of the electrodes 453, 454 are located in the ventricle 405. The first electrode 454 is provided at the farthest distal end 455 of the lead 400 for the purpose of delivering ventricular pacing therapy. The first electrode 454 is referred to as the RV pace/sense tip. A second electrode 453 is located proximate and proximal to electrode 454 and can be used as a counter electrode or as an electrode for defibrillation therapy. The electrode 453 is also known as the distal coil or the RV shock coil. The second electrode 453, in one embodiment, is a shocking coil and is much longer than the first electrode 454. The first electrode 454 and the second electrode 453 can each be coupled with the heart wall using either passive or active fixation.

A third electrode 461 is located at a more proximal position, for example, along the curved portion 450, for the purpose of delivering atrial pacing therapy. The third electrode 461 is also used for atrial sensing, and is referred to as the atrial sense/pace electrode. In one embodiment, the third electrode 461 is passively attached to the atrial wall of the heart. The atrial electrode 461 has a relatively small electrically active surface area. The advantages of this small surface area are high impedance for lower current drainage and a small lead cross section for ease of venous access and transport through the subclavian vein. A fourth electrode 462 is located proximate and proximal to electrode 461 and can be used with electrode 461 for atrial sensing/pacing and as counter to 453 as part of a defibrillation therapy system. Electrodes 453 and 462, in one configuration, are coils of a biocompatible metal or metal alloy such as, but not restricted to, platinum, or platinum/iridium. The coils are generally known as shocking coils and deliver large amounts of energy used in cardioversion and defibrillation. Electrode 462 is also referred to as the proximal coil or the SVC shock coil. The SVC shock coil 462 is positioned in the upper atrium or the superior vena cava.

Figure 15B:
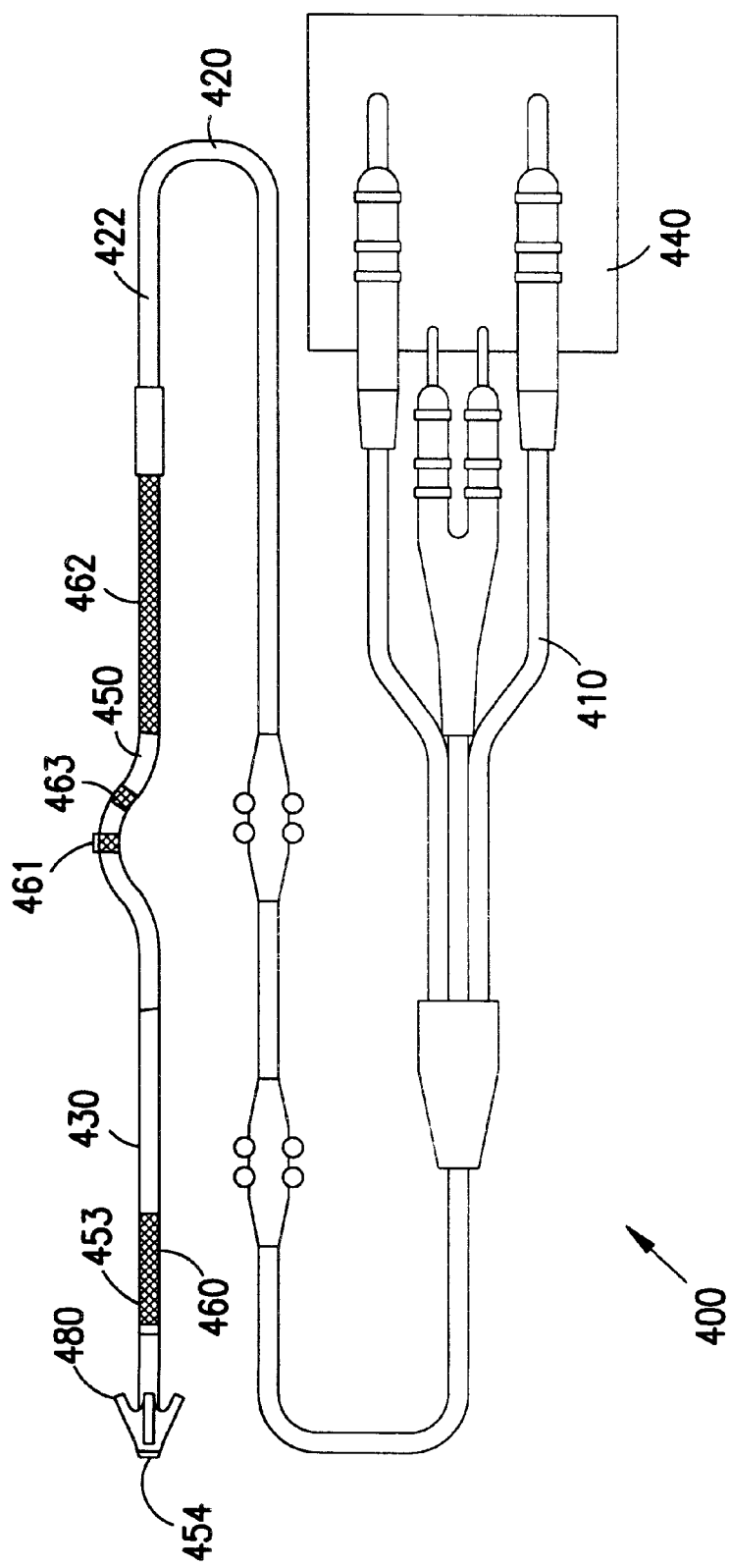
FIG. 15B is a side view of a single-pass lead for sensing and electrically stimulating the heart constructed in accordance with one embodiment of the present invention.

FIG. 15B shows an alternative embodiment, which includes a fifth electrode 463 on the lead 400. The electrode 463 is positioned on the lead 400 adjacent the electrode 461 so that there are two sensing electrodes, 461 and 463 in the atrium of the heart to enhance the sensing capability of this lead. In one embodiment, the electrode 461 comprises a porous tip electrode, as will be further described below.

Figure 16:
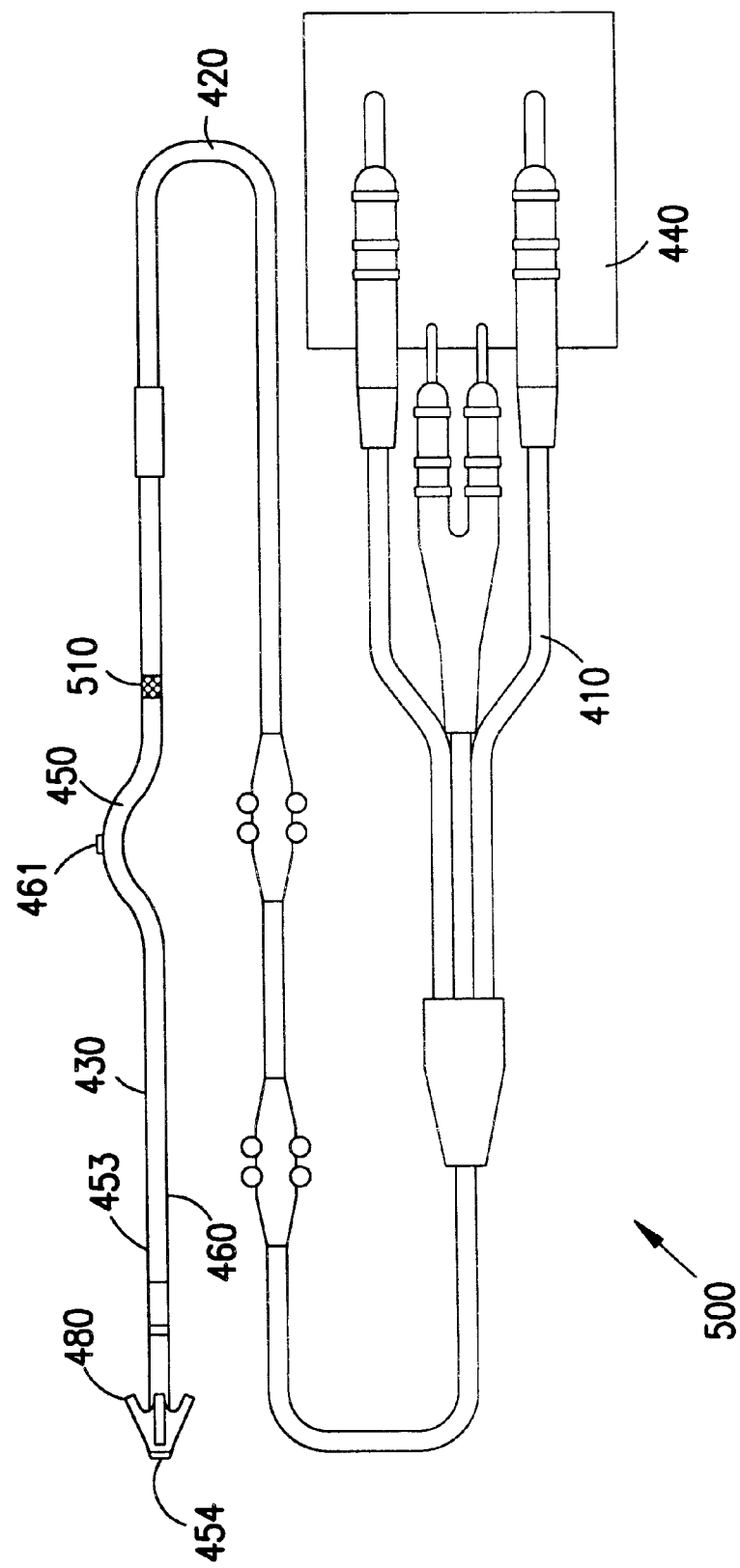
FIG. 16 is a side view of a single-pass endocardial lead for sensing and electrically stimulating the heart constructed in accordance with one embodiment of the present invention.
Figure 18:
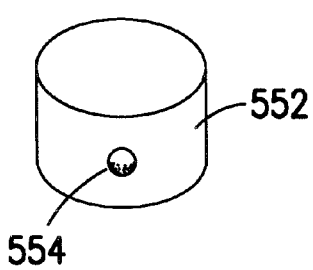
FIG. 18 is a perspective view of the atrial electrode portion of the lead showing a passive attachment element for attachment to the atrial wall of the heart.

FIG. 16 shows a lead 500 used to treat a bradycardia condition. The reference numerals associated with the lead 400 shown in FIGS. 14 and 15 which describe similar parts have been used here for the purposes of simplicity. The lead 500 includes a distal or RV pace sense tip 454, an atrial sense electrode 461, and a ring electrode 510. The distal end 430 of the lead 500 includes a straight portion 460 and a curved portion 450. The atrial sense electrode 461 is positioned on the curved portion 450. The atrial sense electrode 461 can also be provided with a means for passive fixation to the wall of the heart. In this unipolar application, the distal tip electrode 454 serves as the negative pole and the pulse sensor and generator 440 serves as the positive pole when a pacing pulse is delivered to the right ventricle of the heart. It should be noted that this is not the only possible unipolar arrangement, but that other unipolar arrangements are possible. Furthermore, it should be noted that a bipolar arrangement may also be used.

The electrode 461 on the curved portion is disposed such that points out in the direction of the bias of the curved portion 450. In one embodiment, the electrode 461 is a ring electrode which is disposed transverse to the lead body 422. In another embodiment, the electrode 461 is on the larger radius of the curved portion 450 of the lead. This assures that the distance between the electrode 161 and the wall of the atrium 404 is minimized. This also maximizes the possibility that the electrode 461 will become passively fixed to the wall of the heart. In another embodiment, the outside surface of the curved portion 450 of the lead 500 can be textured to further enhance the passive fixation of the lead 461 to the heart.

In another embodiment, the ring electrode 510 is also placed a selected distance from the electrode 461. The ring electrode 510 has the opposite polarity of the electrode 461. The ring electrode 510 is placed so that it is near the superior vena cava of the heart when the lead 500 is placed in the heart. The electrodes 510 and 461 are used as a bipolar pair for sensing and pacing. The lead 500 is a single pass lead that can be used for both sensing a bradycardia condition and treating it by pacing.

FIG. 17A illustrates an alternative form of a lead 520. A conventional endocardial lead, having standard electrodes for the RV tip 522, RV coil 524, and SVC coil 526 on a generally flexible multi-lumen tubular body 530 is shown. Also included is an additional SVC sense ring 528, and a curved shape 532 to hold the sense ring into contact with the interior wall of the atrium or superior vena cava. The lead 520 includes a curved portion 532 which in one embodiment, comprises a semi-flexible, semi-rigid arch which is set in the lead to form a lateral protrusion. The curved portion 532 mechanically biases the atrial sense ring into contact with the inside wall of the atrium, or can be used to bias the lead 520 into contact with other parts of the heart wall. In one embodiment, the curved portion 532 is spaced from the distal tip 534 of the lead 520 so as to be placed in the atrium when the lead 520 is in its use position with the RV tip 522 is in the ventricle. In one embodiment, the atrial sense ring 528 is a small ring electrode paced around the lead at the curved portion 532, in a position where it will be in contact with the atrium when the lead is placed in the heart. In another embodiment, the axis of the sense ring 528 is aligned with the axis of the lead body 530. In yet another embodiment, the axis of the sense ring 528 is co-axial with the axis of the lead body 530. The advantage of the above embodiments is that the atrial sense ring 528 is held in direct contact with the atrial wall, which provides better signals for P wave discrimination, as compared with lead designs which do not ensure such direct contact.

The lead may be constructed generally according to known techniques for multi-lumen intravascular electrode leads, an example of which is shown and described in U.S. Pat. No. 4,603,705 to Speicher et al. The addition of atrial sense ring 528 will require an additional conductor inside the body of the lead. For this reason, the lead of FIG. 17A has four lumens 536, which are seen in the section 550 drawn at the top of the FIG. 17A. The four lumens 536 are the atrial ring lumen, the distal RV coil lumen, the proximal SVC coil lumen, and the lumen for the stylet coil 540 (FIG. 17B) which may also serve as the conductor for the tip electrode. A stylet coil 540, as illustrated in FIG. 17B, is normally found in multi-lumen intravascular electrode leads, consisting of a flexible metallic coil in one of the lumens serving to receive a stylet as is generally known for facilitating directional control of the lead during its placement in the heart. The double-bend portion or curved portion 542 of the stylet coil 540 which forms the curved portion 532 may preferably be formed by forming the bends in the stylet coil to take a 'set' in which the curved portion 532 is shaped as shown in FIG. 17A. The stylet coil 540 has sufficient flexibility to straighten, then return towards the set shape after removal of the stylet.

In one embodiment, the distance 548 of the offset of the curved portion 532 as indicated in FIG. 17A ranges from 1 to 3 centimeters. The length or axial extent 546 of atrial sense ring 528, in one embodiment, as indicated in FIG. 17A is 0.5 to 3.0 millimeters. The axial distance 547, in another embodiment, of atrial sense ring 528 from the SVC coil 526 as indicated in FIG. 17A is 0.5 to 3.0 centimeters.

FIGS. 18–25 further detail certain elements of the passive fixation single pass electrode used for an electrode to be disposed along the curved portion. FIG. 11 shows a conductive ring made of a highly conductive, and highly corrosion resistant, material such as an alloy of platinum-iridium. The ring 552 includes a small porous tip electrode 554. The ring 552 is electrically insulated from body fluids. The porous tip electrode is electrically active and in contact with body fluids and tissue. The active porous tip electrode 552 includes a screen of porous conductive material such as the alloy of platinum and iridium. Over time, the tissue encapsulation grows into the screen made of a platinum-iridium alloy to attach the electrode or electrodes to the endocardial wall of the heart. The ring 552, in one embodiment, has a nominal radius of 0.04 inches (1 mm). The advantage of this small radius is ease of venous access and high impedance for conserving pacing energy.

Figure 19:
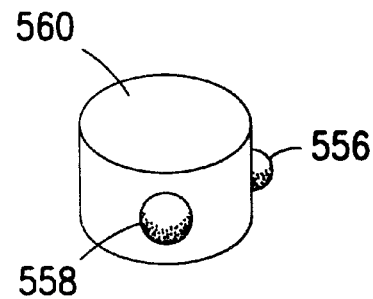
FIG. 19 is a perspective view of another embodiment of the electrode for passive attachment to the atrial wall of the heart.

FIG. 19 shows another passive fixation electrode. FIG. 19 shows a conductive ring 560 made of a highly corrosion-resistant material such as an alloy of platinum and iridium, and in one embodiment is electrically insulated from body fluids. The ring includes two small porous tip electrodes 556 and 558, which are electrically active and in contact with body fluids. The active porous tip electrodes 556 and 558 each include a screen of porous conductive material made of the highly corrosion-resistant alloy of platinum and iridium. Tissue encapsulation grows into the screen on the tips 556 and 558 to attach the electrode to the endocardial wall of the heart.

Figure 20:
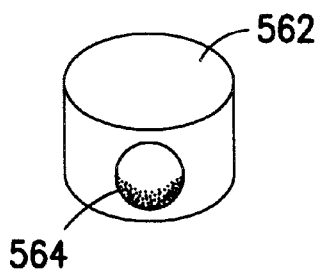
FIG. 20 is a perspective view of another embodiment of the electrode for passive attachment to the atrial wall of the heart.

FIG. 20 shows another passive fixation element associated with the curved portion of the lead. A conductive ring 562 made of a highly corrosion-resistant material such as an alloy of platinum and iridium, and in one embodiment is electrically insulated from body fluids. The ring 562 includes a porous tip electrode 564, which is electrically active and in contact with body fluids. The porous tip 564 in FIG. 20 is larger than the porous tip 554 shown in FIG. 18, where the porous tip 564 extends across a substantial amount of the tip 564. In one embodiment, the porous tip 564 is made of corrosion-resistant material and comprises a screen. When the porous tip 564 rests against the endocardial wall of the heart, the tissue of the heart encapsulates and grows into the screen to passively attach the electrode to the heart.

Figure 21:
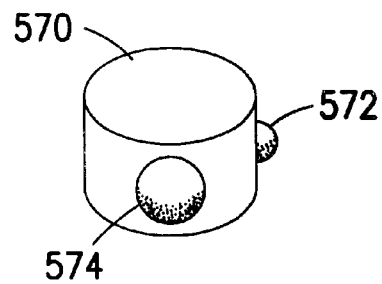
FIG. 21 is a perspective view of another embodiment of the electrode for passive attachment to the atrial wall of the heart.

FIG. 21 illustrates a variation of the electrode shown in FIG. 20, where the conductive ring 570 includes a first porous tip 572 and a second porous tip 574. The ring 570 is electrically insulated from body fluids, and the first and second porous tips 572 and 574 are electrically active and in contact with body fluids. The porous tips 572, 574 are also made of highly corrosion-resistant material. Like the previous conductive rings shown, the tissue of the heart encapsulates and grows into the porous screen in order to provide passive attachment of the electrode to the endocardial wall of the heart.

Figure 22:
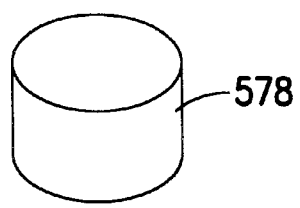
FIG. 22 is a perspective view of another embodiment of the electrode for passive attachment to the atrial wall of the heart.

FIG. 22 shows that a smooth ring 578 can also be used as the main element of the electrode in the curved portion of the lead. The smooth ring 578 is made of a corrosion-resistant material that is highly conductive. All of the ring 578 can be exposed or a portion of it can be masked or insulated, so that a portion is nonconductive.

Figure 23:
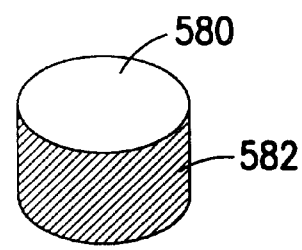
FIG. 23 is a perspective view of another embodiment of the electrode for passive attachment to the atrial wall of the heart.

FIG. 23 shows another variation and includes a ring 580. A surface 582 of the ring 580 is comprised of layers of conductive mesh or other porous materials attached to the ring 580. The layers of conductive mesh or porous materials create an active surface for pacing and sensing and a layer for enhanced tissue ingrowth. Alternatively, texturization or other surface treatment could be applied directly to the ring 580 to enhance tissue ingrowth.

Figure 24:
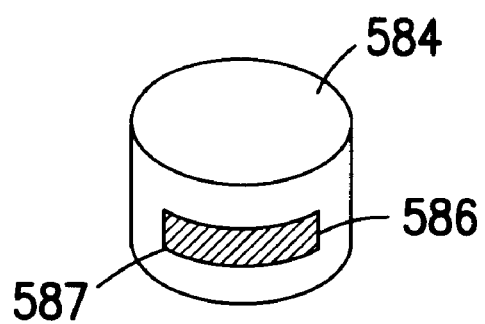
FIG. 24 is a perspective view of another embodiment of the electrode for passive attachment to the atrial wall of the heart.

FIG. 24 illustrates another embodiment of an electrode for use with the curved portion of the lead. A ring 584, made of highly conductive material insulated from body fluids includes a modified raised ridge 586. In one embodiment, layers of conductive porous material are deposited on an electrically conductive thin band 587 rather than across the entire width of the ring. In another embodiment, all of the ring 584 can be exposed or a portion of it can be masked or insulated so that a portion is nonconductive.

Figure 25:
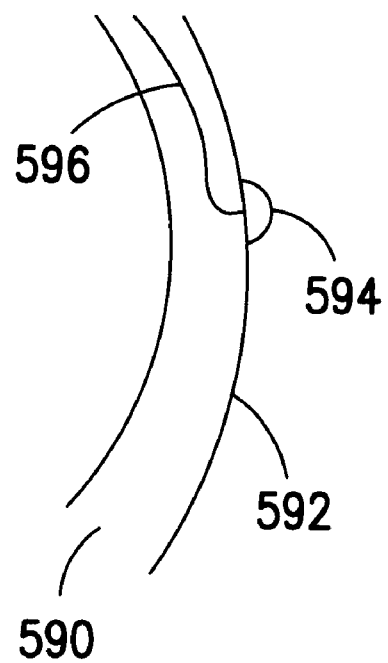
FIG. 25 is a side view of a portion of a lead body showing an electrode for passive attachment to the atrial wall of the heart.

FIG. 25 shows an portion of a lead 590 including a porous tip type of electrode 594 (similar to the porous tip shown in FIGS. 18 and 19) which is not mounted on a ring. The porous tip electrode 594 is placed in either a straight or curved portion of the lead. In one embodiment, the porous tip electrode 594 is placed directly into the surface of the lead 590, and an electrical conductor 596 is attached to the electrode. In another embodiment, the surface of the lead 590 near the electrode 594 may be textured to enhance the ability of the lead 590 to become passively fixed to the wall of the heart. It should be noted that the above described electrodes illustrated in FIGS. 18–25 can be used along any curved or straight portion of a lead, and can be disposed in the various positions described above. The pacing and sensing tip points out in the direction of the bias or, alternatively, is on the portion of the lead body that is closest to the wall of the heart.

Figure 26:
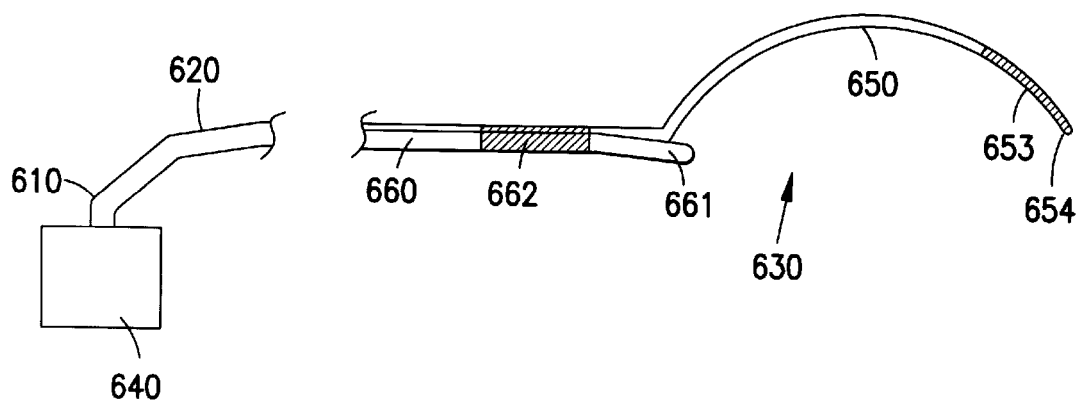
FIG. 26 is a side view of a single-pass endocardial lead for electrically stimulating the heart constructed in accordance with another embodiment of the present invention.
Figure 27:
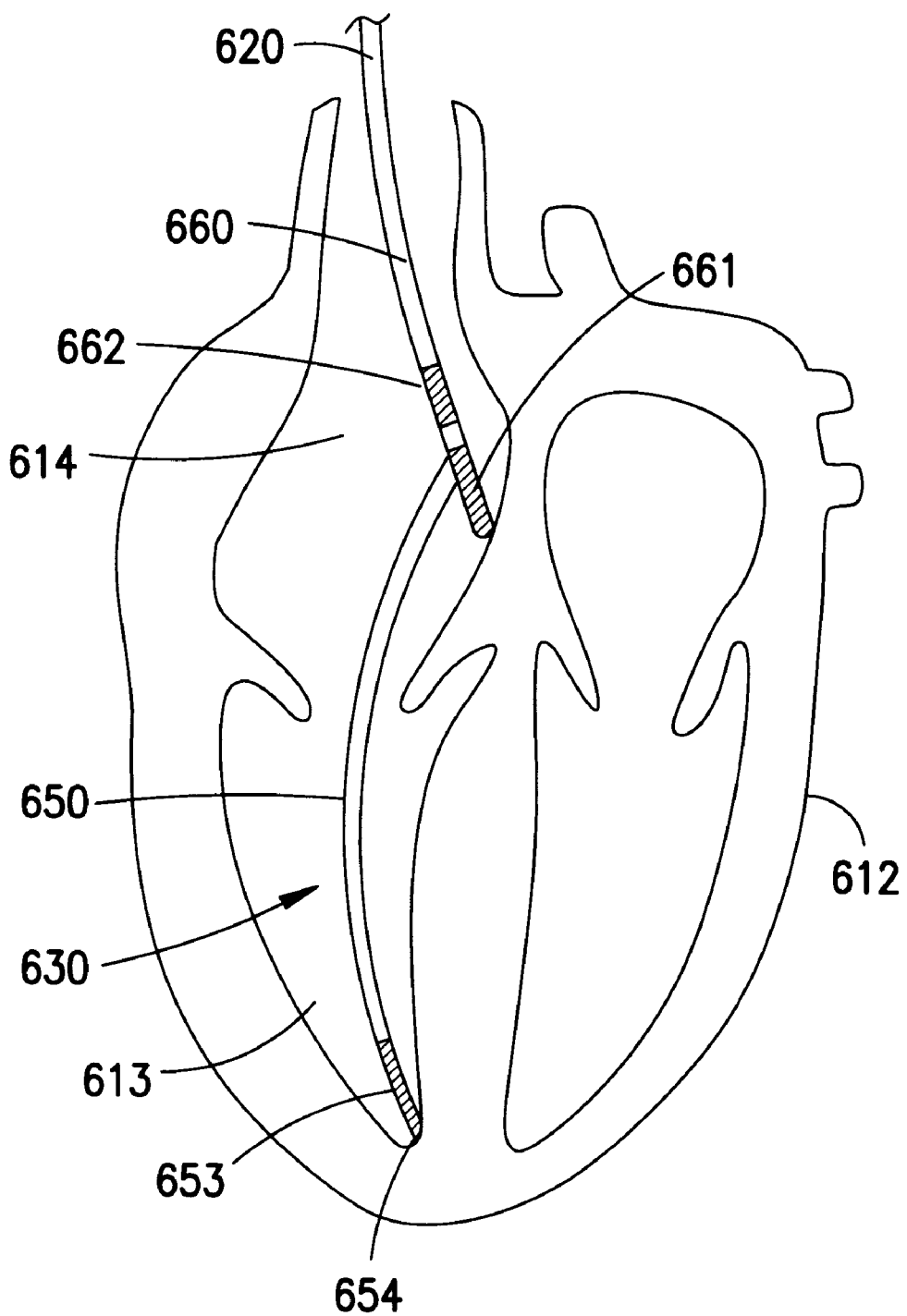
FIG. 27 is a side view of a single-pass endocardial lead implanted within the heart constructed in accordance with another embodiment of the present invention.

FIG. 26 is a side view of one type of lead 600 for delivering electrical pulses to stimulate the heart. The lead 600 is comprised of a connector terminal 610 and a lead body 620. The lead 600 attaches to a pulse sensor and generator 640. The lead body has a number of electrodes in the distal end 630 which is implanted within, on, or about the heart (FIG. 27). The distal end 630 of the lead body 620 includes a curved or bias portion 650 and a straight portion 660. The connector terminal 610 electrically connects the various electrodes and conductors within the lead body to the pulse sensor and generator 640. The pulse sensor and generator 640 contains electronics to sense various pulses of the heart and also produce pulsing signals for delivery to the heart. The pulse sensor and generator 640 also contains electronics and software necessary to detect certain types of arrhythmias and to correct for them. Physicians are able to program the pulse sensor and generator to correct a particular arrhythmia that the patient may have. It should be noted that there are numerous types of connector terminals which connect to a pulse sensing and generating unit 640. The lead terminal connector 610 provides for the electrical connection between the electrodes on the lead 100 and pulse generator 640. The connector terminal end 610 shown is designed to international IS-1 Standard ISO 5841-3(E).

The lead body 620, in one embodiment, is cylindrical in shape and includes tubing material formed from a polymer biocompatible for implantation, and preferably the tubing is made from a silicone rubber polymer. The silicone rubber polymer tubing contains several electrical conductors (not shown). The electrical conductors are made of a highly conductive, highly corrosion-resistant material which is formed into a helix, and are housed within the lead body 620. When there is more than one such electrical conductor within the lead body 620, the lead is called a multifilar lead. The electrical conductors carry current and signals between the pulse sensor and generator 640 and the electrodes located at the distal end 630 of the lead 600.

After implantation within or on or about the heart 612, as illustrated in FIG. 27, the curved or biased portion 650 will generally be located in the right ventricle 613 of the heart. The straight portion 660 of this lead body will generally be located in the right atrium 614.

In one embodiment, the distal end 630 of the lead 600 has four electrodes. The first electrode 654, also referred to as the distal electrode, is provided at the farthest distal end of the lead for the purpose of delivering ventricular pacing therapy. A second electrode 653 is located near the first or distal electrode 654 and can be used as a counter electrode for electrode 654 or as a current source for defibrillation therapy. This electrode 653 is sometimes referred to as a ventricular shocking coil. A third electrode 661 is located at a more proximal position for the purpose of delivering atrial pacing therapy. The electrode 661, in another embodiment, is actively attached to the atrial wall of the heart 612. The third electrode 661 is also referred to as the proximal electrode. A fourth electrode 662 is located near the electrode 661 and can be used as a counter electrode for electrode 661 or as part of a defibrillation therapy system. The fourth electrode 662 is sometimes called the SVC shocking coil. The lead 600 may be generally described as a tachycardia or tachy lead. The shocking coils 653 and 662 are electrically conductive rings made of an alloy of platinum and iridium which is highly conductive and highly resistant to corrosion. The electrode 661 uses, in one embodiment, the active fixation element described further below. The electrode 654 may include an active fixation or passive fixation portion. It should be noted that the lead shown and described above is a bipolar lead in that the positive and negative portions of a circuit are located in the lead body 600. It should be noted that this lead may also be made a unipolar lead. In other words, one electrode of the lead body 600 can be the shocking coil and the other electrode can be the signal generator.

In one embodiment, the relaxed shape of the lead body 620 conforms to the shape the lead is expected to take after implantation. The distal portion of the straight portion 660 and the proximal portion of the curved portion 650 are biased to conform to the mid-portion of the atrial wall. This shape facilitates the placement of electrode 661 against the atrial wall during implantation. Furthermore, because the natural unstressed shape of the lead before implantation is approximately the same after implantation, this reduces the nominal residual stresses in the lead body. Also, this will reduce the nominal forces between the atrial wall and the point of attachment of the electrode 661 in the atrium. In another embodiment, the shape of the middle and end portions of portion 650 conforms to the shape of the upper ventricular chamber below the tricuspid valve and ventricular septal wall. This shape will tend to cause the lead 600 to lie across the top of the ventricle in a gradual arc with the electrode 653 lying against the ventricular septum and electrode 654 resting in the ventricular apex. This lead position is advantageous because the arc shape will tend to reduce the transmitted forces between the lead fixation points at electrode 661 in the atrium and electrode 654 in the ventricle as they move relative to each other during heart rhythm. This preformed shape will ease the surgeon's task of positioning of lead 600 and, particularly, of the electrode end 630 such that less time is required and the placement procedure is less prone to error.

The discussions of leads having a curved portion in related co-pending applications entitled SINGLE PASS DEFIBRILLATION/PACING LEAD WITH PASSIVELY ATTACHED ELECTRODE FOR PACING AND SENSING, Ser. No. 09/121,020, and Attorney Docket No.: 279.116US1; SINGLE PASS LEAD HAVING RETRACTABLE, ACTIVELY ATTACHED ELECTRODE FOR PACING AND SENSING, Ser. No. 09/121,006, and Attorney Docket No.: 279.058US1; SINGLE PASS DEFIBRILLATION/PACING LEAD WITH PASSIVELY ATTACHED ELECTRODE FOR PACING AND SENSING, Ser. No. 09/121,018, and Attorney Docket No.: 279.054US1, all filed even date herewith and DISCRIMINATION OF ATRIAL AND VENTRICULAR SIGNALS FROM A SINGLE CARDIAC LEAD, Ser. No. 08/996,355, filed Dec. 22, 1997, all of which are hereby incorporated by reference in their entirety. The above described leads, including but not limited to multi-site pacing leads for one or more chambers of the heart, as well as bifurcated leads can also be combined with the embodiments relating to the leads having a curved portion.

Figure 28:
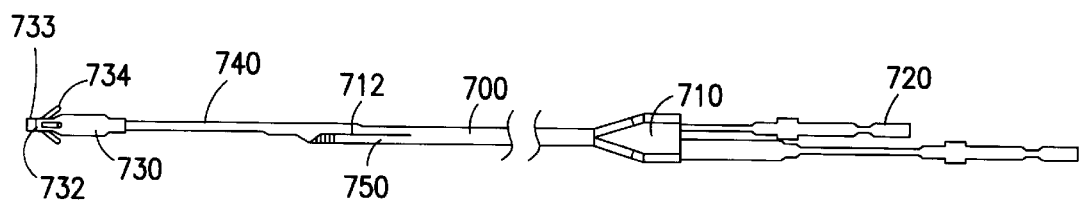
FIG. 28 is a side view of a single-pass endocardial lead for multi-site pacing during insertion with a first atrial leg straight and one atrial leg withdrawn into the lead body constructed in accordance with one embodiment of the present invention.

FIG. 28 illustrates a side view of a single-pass endocardial lead 700 for multi-site pacing within a single chamber of the heart. During insertion, a stylet or wire is placed down a lumen within the lead 700. This makes for a stiffened lead body 700 which can be pushed through the body into the appropriate chamber of the heart. The lead 700 includes a connector end 720 which, in one embodiment, has a yoke 710 and extends to a distal end 730. The lead 700 also includes a first leg 740 and a second leg 750, which each include at least one electrode.

The lead 700 includes a recess 712 which houses the second leg 750. The second leg 750 is maintained within the recess 712 while the lead 700 is being routed through the body, into the major vein or subclavian vein and ultimately into one of the chambers of the heart. The electrode 732 associated with the first leg 740, in one embodiment, includes a passive fix element 733. The passive fix element 733, in one embodiment, includes a wire mesh screen which allows for the fibers of the heart to grow within the fiber mesh screen over time. In yet another embodiment, the passive fix element 733 includes a set of tines 734 near the electrode 732. The tines 734 also provide for attachment of the electrode 732 to the endocardial wall of the specific chamber in the heart to which the first leg 740 of the lead 700 is to be attached.

Figure 29:
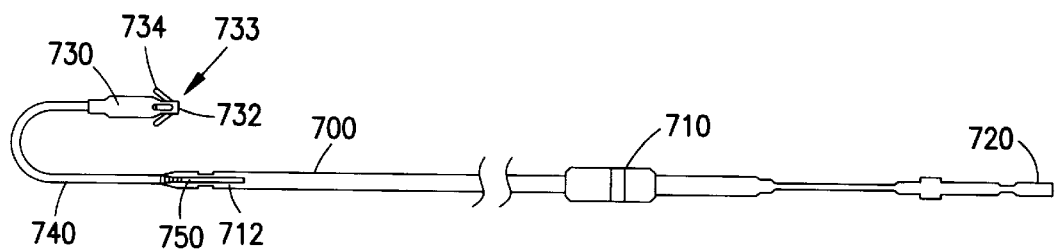
FIG. 29 is a side view of a single-pass endocardial lead for multi-site pacing during insertion with a first atrial leg formed into atrial 'J' after withdrawal of stylet and one atrial leg withdrawn into the lead body constructed in accordance with one embodiment of the present invention.

FIG. 29 illustrates another side view of the lead 700 after the stylet (not shown) which extends down the body of the lead 700 and into the first leg 740 has been removed. When the stylet is removed, the first leg 740 is allowed to return to its natural state. In this particular case, the first leg 740 of the lead 700 includes a curve therein, for example, a J-shaped curve. The radius of the curve and the length of the leg 740 are or may be varied in order to accomplish placement of the lead 732 at various positions within a particular single chamber of the heart. It should be noted that FIG. 29 illustrates the second leg 750 still housed within the recess 712 in the body of the lead 700.

Figure 30:
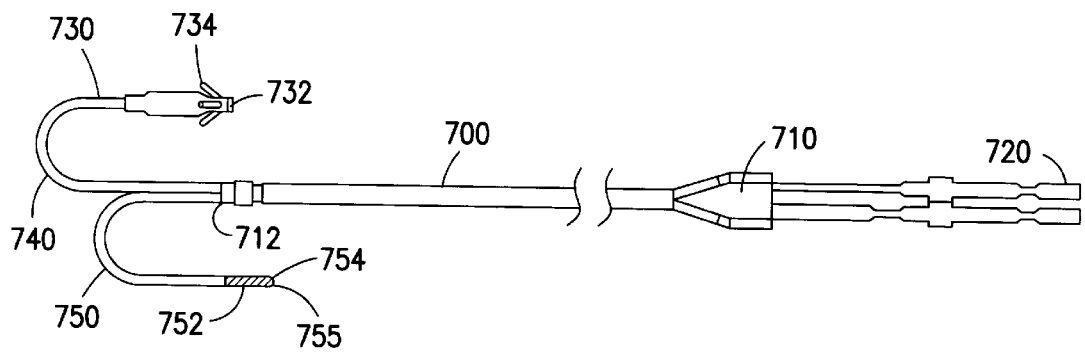
FIG. 30 is a side view of a single-pass endocardial lead for multi-site pacing during insertion with both atrial legs formed into a 'J' constructed in accordance with one embodiment of the present invention.

Now turning to FIG. 30, the single-pass endocardial lead 700 for multi-site pacing is shown after the second leg 750 has been removed or pushed out of the recess 712 within the body of the lead 700. The second leg 750 is also J-shaped or curved and has an electrode 752 positioned near the free end 755 of the leg 750. The free end 755 of the second leg 750 also includes an active fix element 754 which is used to actively fix the electrode 754 to an endocardial wall of a chamber of the heart. It should be noted that the first leg 740 and the second leg 750 need not be J-shaped or curved and that either the first leg or the second leg each can either include a passive fix element or an active fix element. The advantage of this particular configuration is that the passive fix element will not catch on any of the veins or tissue as it is passing through the subclavian vein and into the heart. As this is being done, the active fix portion 754 of the second leg is kept within the recess 712 of the lead 700 so that the active fix element 754 will not catch on any tissue during insertion. It should also be noted that the radius of the curve and the position and length of the first leg 740 and the second leg 750 can be varied for various applications of multi-site pacing within a single chamber of the heart. It should be noted that for different chambers, different lengths of the legs 750 and 740 might be appropriate, as well as different radii. The configuration shown in FIG. 30 could be placed or positioned within the atrium (not shown) of the heart. This configuration could be used for simultaneous atrial appendage and Bachman's Bundle pacing.

Figure 31:
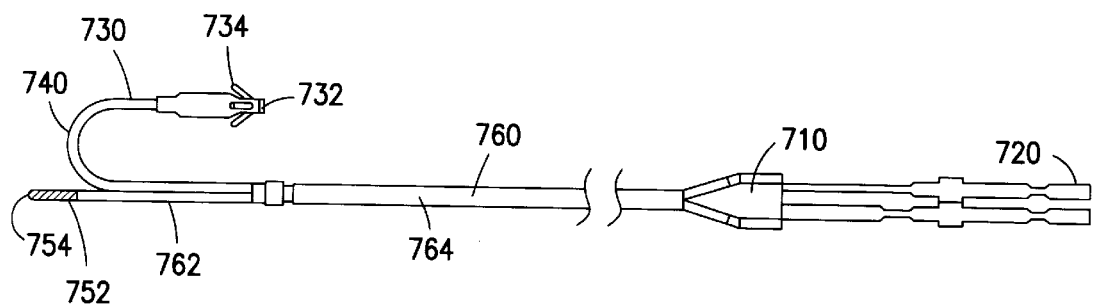
FIG. 31 is a side view of a single-pass endocardial lead for multi-site pacing during insertion with one atrial leg formed into a 'J' and one leg straight constructed in accordance with one embodiment of the present invention.

FIG. 31 shows a variation of a single-pass endocardial lead 760 for multi-site pacing from the ones shown in FIGS. 28–30. The lead 760 shown in FIG. 31 includes many of the same elements of the lead shown in FIGS. 28, 29, and 30. Rather than repeat all the same elements or similar elements between the lead 760 and the lead 700 shown in FIGS. 28, 29, and 30, only the differences will be touched upon or described in the following paragraph.

The lead 760 differs from the lead 700 in that the lead 760 includes a second leg 762 which is straight after it has been removed or forced out of the recess in the lead body 764. The second leg 762 includes an electrode 752 as well as an active fix portion 754 for attaching to the endocardial wall of the heart. If this configuration was placed in the atrium, it could be used for simultaneous atrial appendage pacing, and pacing at the entrance of the coronary sinus.

Figure 32:
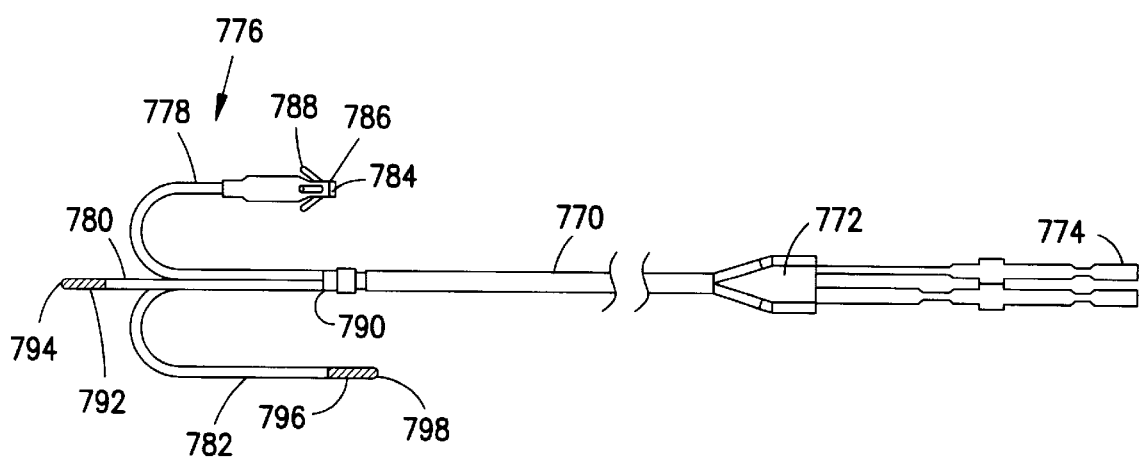
FIG. 32 is a side view of a single-pass endocardial lead for multi-site pacing during insertion with two atrial legs formed into a 'J' and one leg straight constructed in accordance with one embodiment of the present invention.

FIG. 32 shows yet another embodiment of a single-pass endocardial lead 770 for multi-site pacing within a single chamber of the heart. The lead 770 includes a connector end 774 and a distal end 776 having a first leg 778, a second leg 780 and a third leg 782. The lead 700 has a recess which is capable of holding a second leg 780, and a third leg 760. The first leg 778 is, in one embodiment, J-shaped or, alternatively, curved and includes an electrode 784. The electrode 784, in another embodiment, is used as part of an active fix element 786. The first leg 778 also includes a set of tines 788 which enables or allows active fixation of the electrode 778 to an endocardial wall of the heart. The second leg 780 is a straight leg having an electrode 792 and an active fix portion 794. The third leg 782 includes an electrode 796 and an active fix portion 798.

During insertion of the lead 770 into a patient, a stylet (not shown) is placed into a lumen of the lead 770. The stylet will pass all the way down to and into the first leg 778 of the lead 770. During insertion, the second leg 780 and the third leg 782 will be housed or in a withdrawn position within either a single recess 790, or alternatively a pair of recesses within the lead 770. With the stylet in place, the lead can be maneuvered and positioned through the major arteries and into the heart. Once the lead 770 is positioned within the heart, the stylet is removed and a J-shaped natural shape is assumed by the first leg 778. After the lead 770 has been placed within the selected chamber of the heart, the second leg 780 and the third leg 782 can be removed or extended out of the recess in the body of the lead 770. It should be noted that the first, second and third legs 778, 780, 782 may either be curved or alternatively J-shaped and can also either be attached to the endocardial wall of the heart by active fixation or passive fixation. The position and length of the legs can be varied to produce different multi-site placements of the electrodes within the heart. Each of the electrodes 784, 792 and 796 can be either a bipolar or unipolar configuration. The particular configuration shown in FIG. 32, if placed within the atrium of the heart, can be used for a simultaneous atrial appendage, pacing at the Bachman's Bundle and pacing at the entrance to the coronary sinus.

Figure 33:
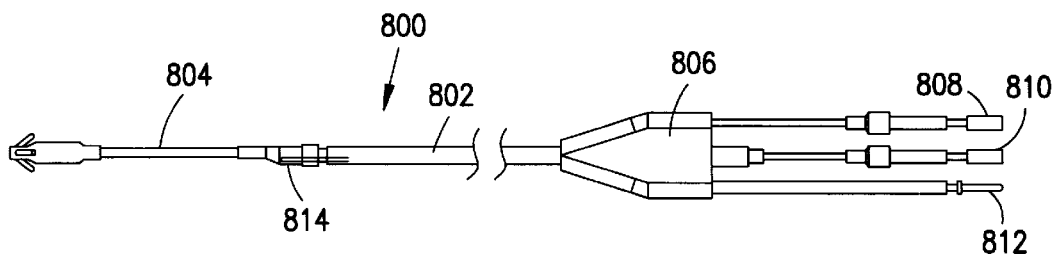
FIG. 33 is a side view of a single-pass endocardial lead for multi-site pacing constructed in accordance with one embodiment of the present invention.
Figure 34:
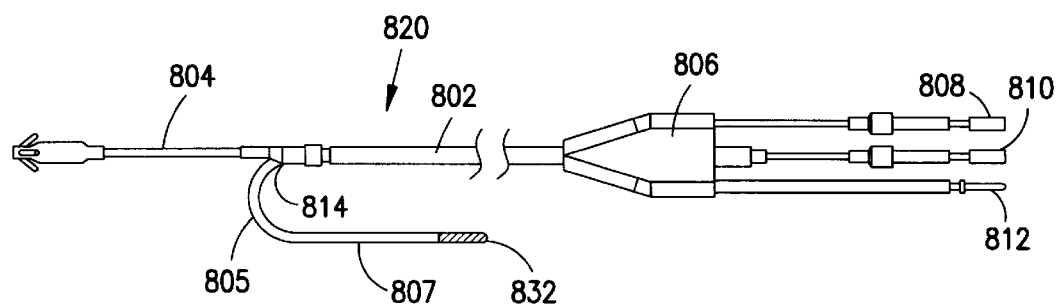
FIG. 34 is a side view of a single-pass endocardial lead for multi-site pacing constructed in accordance with one embodiment of the present invention.
Figure 35:
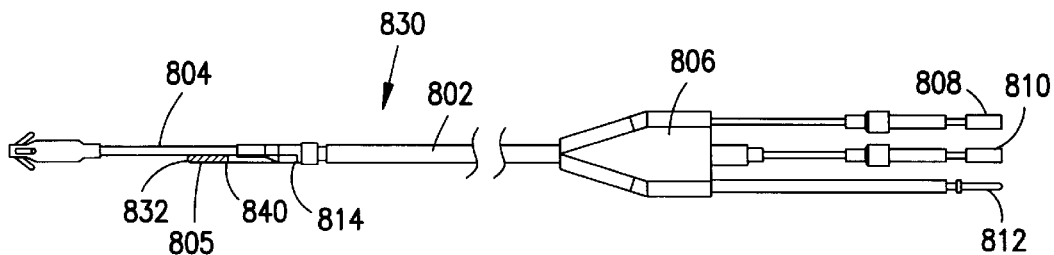
FIG. 35 is a side view of a single-pass endocardial lead for multi-site pacing constructed in accordance with one embodiment of the present invention.

FIGS. 33, 34, and 35 show several other embodiments of the invention. FIG. 33 is a side view of a lead 800 which includes an active fixation element 832 for attachment to the atrial wall of the heart. The lead 800 includes a main lead body 802, an atrial lead body 805 (FIGS. 34 and 35) and a ventricle lead body 804. The main lead body 802 is attached to a yoke 806. The yoke 806 acts as a strain reliever and also has a series of terminal pins 808, 810 and 812 attached to the yoke/strain reliever 806. The terminal pins 808, 810, and 812 are attached to the pulse generator (not shown). The main lead body 802 is longer than as shown; a break has been put into the main lead body 802 to illustrate that the main lead body 802 is longer than that shown in FIG. 33.

The main lead body 802 includes a recess 814 where the atrial lead body 805 (FIGS. 34 and 35) fits within the recess 814 in the main lead body 802. When the atrial lead body 805 is housed within the recess 814, an active fixation element 832 on the end of the atrial lead body 805 and associated with the proximate electrode is also housed within the recess 814. Advantageously, the active fixation element 832 will not hook or snag tissue when it is housed within the recess 814. Typically, the atrial lead body 805 is pulled back or housed within the recess 814 when the lead 800 is being surgically implanted into the patient. Typically, the lead 800 is placed in the subclavian vein of the patient and then passed through the subclavian vein to the inner chambers of the heart. Once the lead and, more specifically, the distal electrode and the proximal electrode are within the ventricle and atrium of the heart, the various leads are removed from their respective recesses so that a surgeon can attach them to the inner wall of the heart.

FIG. 34 is a side view of the embodiment of a lead 800 shown in FIG. 33. FIG. 34 has a J-shaped atrial lead body 807 which emerges from the recess 814 in the main body 802 of the lead 820. On the end of the atrial lead 807 is an active fixation element 832. The active fixation element 832, in one embodiment, includes a helically shaped hook for screwing into the atrium of the heart. The J-shape of the lead facilitates positioning of the end of the electrode having the active fixation element 832 to a desired position within the atrium. The J-shape eases positioning within the atrium of the heart when certain portions of the atrium are the target for connection of the active fixation element 832. Once properly positioned, a surgeon can turn and/or advance the active fixation element 832 causing it to hook the tissue in the inner wall of the heart. The atrial lead 807, in one embodiment, is moved with respect to the recess 814 by pushing the respective terminal pin 810 toward the yoke 806. By moving the terminal pin 810 toward the yoke 806, a conductor, which connects the terminal pin 810 and the active fixation element 832, moves with respect to the main body 802 of the lead 820. Alternatively, the terminal pin 810 can be moved longitudinally with respect to the main body 802. This movement causes the atrial lead body 807 to emerge or pass through or pass out of the recess 814 in the main body 802. The terminal pin 810 and the active fixation element 832 attached to it, in one embodiment, move independently of the lead body 820. Twisting the terminal pin causes the active fixation element 832 on the atrial lead body 807 to turn and affix itself to the atrial wall of the heart. This additional degree of freedom allows for movement of the lead body relative to the fixed atrial electrode without unscrewing (or over-screwing) the electrode from the endocaridal tissue. A locking mechanism may be provided to prevent the active fixation element 832 from "backing out" after it has been affixed to the wall. The atrial lead 807, in another embodiment, is prestressed so that it will take the J-shape upon leaving or coming out of the recess 814.

FIG. 35 is a side view of another embodiment of the lead shown in FIG. 33. In this particular embodiment, the lead 830 has a straight atrial lead body 840 which comes out of the recess 814 in the main lead body 802. The position of the atrial lead body 840 is controlled by movement of the terminal pin 810 with respect to the yoke 806. Moving the terminal pin 810 with respect to the yoke 806 causes the atrial lead 840 to come out of the recess 814. An active fixation element 832 is positioned on the end of the atrial lead 840. Once the surgeon positions the atrial lead 840 and the active fixation element 832 at the end of the atrial lead 840 in a proper position or desired position, the active fixation element 832 is used to attach the proximal electrode to the endocardial wall of the atrium.

Figure 36:
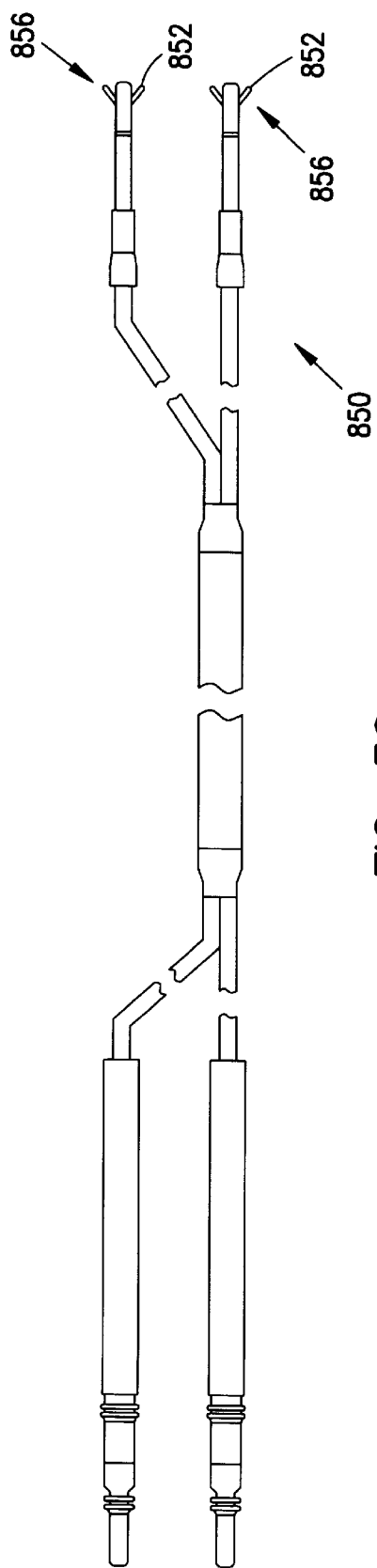
FIG. 36 is a side elevational view illustrating a single-pass lead constructed in accordance with another embodiment of the present invention.

The above and below-discussed lead embodiments can each be provided with, for example, active or passive fixation devices. FIG. 36 illustrates one embodiment of a passive fixation device 856. A plurality of tines 852 are disposed about the distal end 854 of the electrode 850. Other examples of a passive fixation device 856 include a mesh screen (further discussed below) which can be used independently or in combination with other passive fixation devices such as the plurality of tines 852. Other passive fixation devices are also shown in FIGS. 14, 15A, 15B, 16, 17A, and 28–35.

Figure 37:
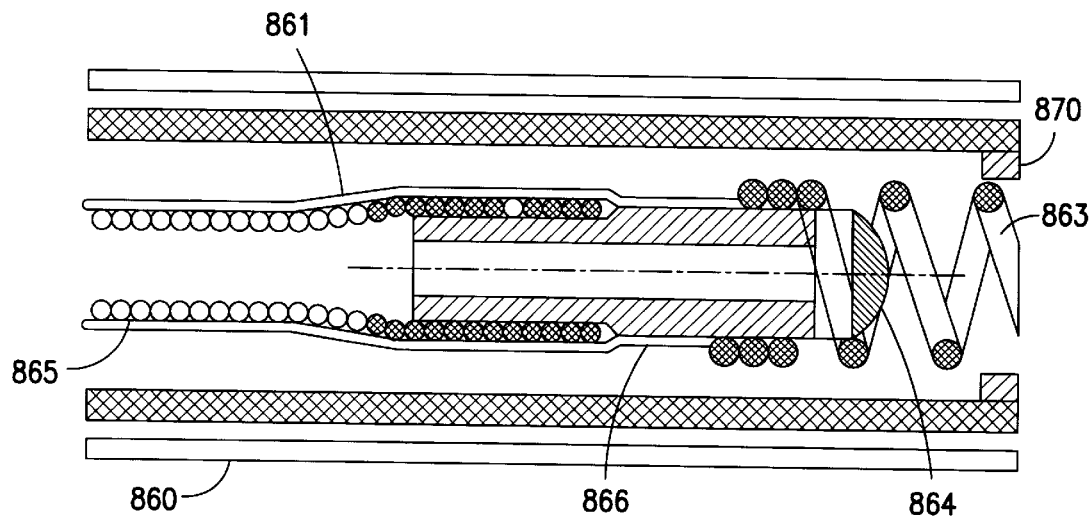
FIG. 37 is a cross-section view illustrating a single-pass lead constructed in accordance with one embodiment of the present invention.
Figure 38:
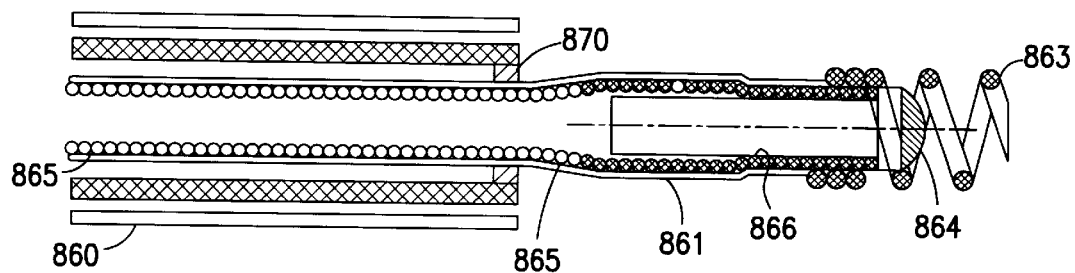
FIG. 38 is a cross-section view illustrating a single-pass lead constructed in accordance with one embodiment of the present invention.

In another embodiment, the above and below discussed lead embodiments can alternatively and/or additionally be provided an active fixation device. One example of an active fixation device for the lead is a retractable screw, as shown in FIGS. 10–13, 26, 30–32, 34, and 35, and also further described below. FIGS. 37 and 38 illustrate another embodiment of an active fixation device. As mentioned previously, the electrode 861 is designed to be attached to the wall of the heart. FIG. 37 shows electrode 861 in a recessed position and FIG. 38 shows electrode 861 actively extended. In this embodiment, the electrode 861 includes an active fixation screw 863 which, in one embodiment, comprises a helical screw. The electrode 861, in one embodiment, is configured to initially rest inside the lead body 860, and then extend and rotate independent of the lead body 860 for attachment to the wall of the heart. FIG. 37 shows the electrode 861 and the fixation screw 863 resting within the lead body 860. A seal 870 is provided, in another embodiment, which assists in preventing body fluids from traveling into the recess in the lead body. The seal 870 is made of a biocompatible material such as silicone rubber and may take any appropriate shape. In this instance, the seal 870 is shaped as a permanent O-ring affixed to the recess in the lead body 860. This covered position of the electrode 861 and active fixation screw 763 makes the lead placement process easier since the electrode 861 does not snag the vein during initial venous access and subsequent movement of the lead to the heart. The seal 870 can also be used to hold a lubricant (not shown) within the recess of the body 860 of the lead. The lubricant will allow the electrode 861 to move from inside the recess to outside the recess with greater ease. The lubricant can be a substance such as fluorosilicone which is biocompatible.

FIG. 38 shows the electrode 861 extended from the lead body 860. The electrode 161 and active fixation screw 863 move independent of the lead body 860. This relative movement allows the electrode to come in contact with the wall without manipulation of the lead body 860. The electrode 861 can then be fixed by rotating the electrode 861 and attached fixation screw 863. The fixation screw 863 of the electrode 861 can be advanced and retracted independent of rotation of the lead body 860. The active fixation screw and attached electrode, in one embodiment, are controlled from the terminal end, as discussed above.

As mentioned previously, the electrically conductive portion 864 which either senses electrical energy produced by the heart or delivers pacing signals to the heart is a small radius electrode. The electrode 861 has a diameter, in one embodiment, in the range of 0.024 inches to 0.050 inches. The advantage of this small radius is ease of venous access and small surface area resulting in high impedance for saving energy. Saving energy makes the battery used to power the pulse generator (discussed above) last longer.

Also shown in FIGS. 37 and 38 is a multifilar coil 865 and an electrically conductive sleeve 866. The conductive sleeve 866 has the smaller radius electrode tip 864 attached at one end of the sleeve. At the other end of the sleeve 866, the multifilar coil 865 is attached. The multifilar coil 865 includes at least one conductor which is used to carry electrical signals to and from the electrode tip 864.

Figure 39:
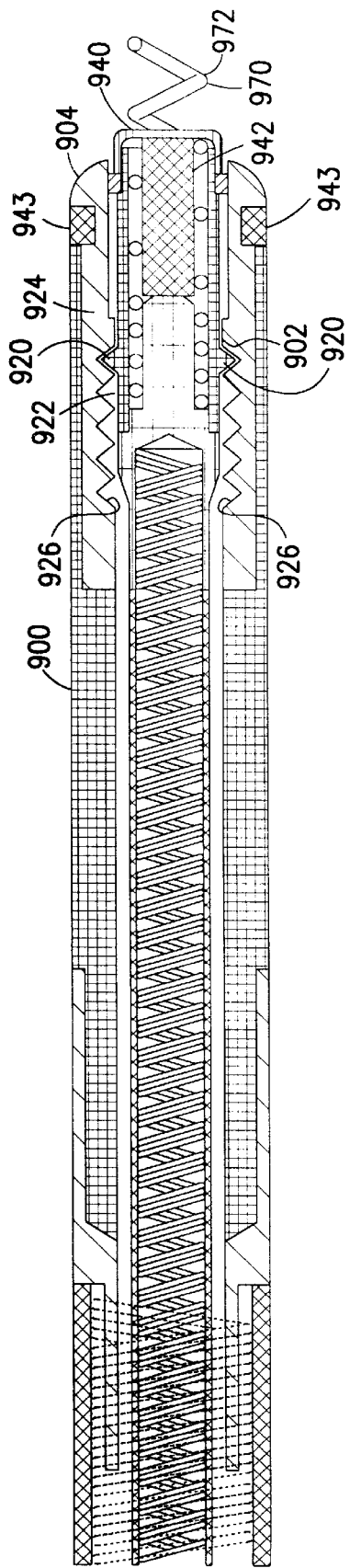
FIG. 39 is a cross-section view illustrating a single-pass lead constructed in accordance with one embodiment of the present invention.
Figure 40:
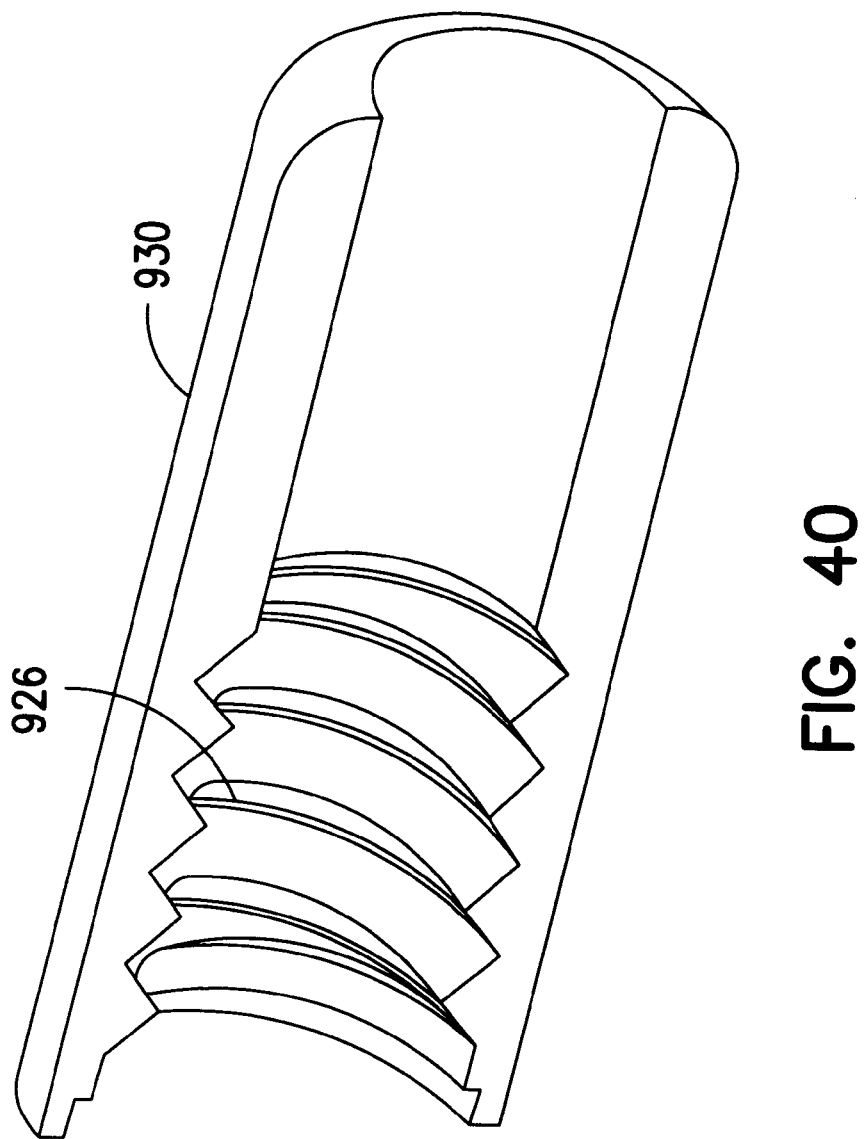
FIG. 40 is a perspective view illustrating a movement assembly of the lead constructed in accordance with one embodiment of the present invention.
Figure 41:
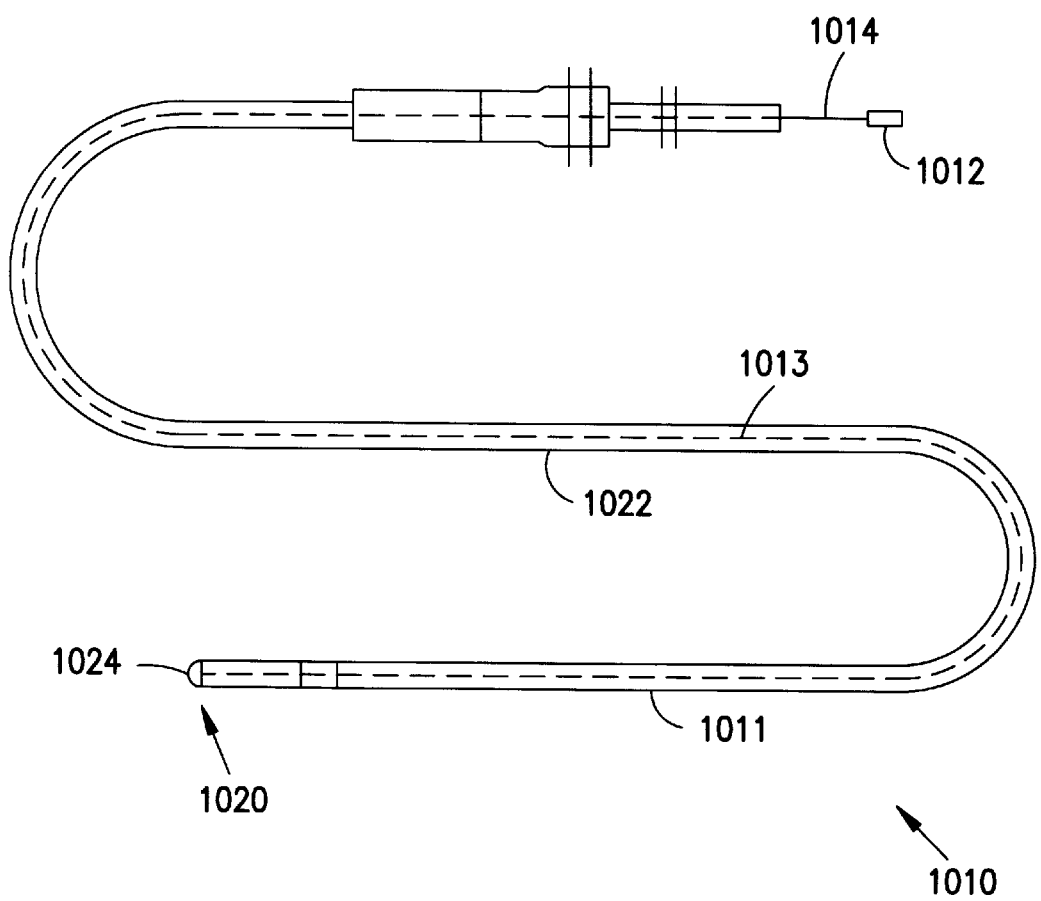
FIG. 41 is a first side elevational view illustrating a lead constructed in accordance with one embodiment of the present invention.

In yet another embodiment, the active fixation device comprises the movement assembly as shown in FIGS. 39 and 40. A lead 900 is provided extending to a distal end 904 which includes an active fixation element 970. The active fixation element 970, in one embodiment, comprises a helical screw 972. In one configuration, the active fixation element 970 is retractable, which assists in avoiding injury to the patient during implantation. Alternatively, the active fixation element 970 rotates without translating along the lead 900. For the configuration where the active fixation element 970 rotates without translating along the lead 900, a material, such as mannitol, is disposed about the active fixation element 970 to prevent snagging the interior of the vein as the lead 900 is positioned within the patient. The lead 900, in one embodiment, includes a movement assembly 902 which is adapted to transport the active fixation element 970. Alternatively, in another configuration, the distal end 904 of the lead 900 can include a passive fixation element, as discussed above.

The movement assembly 902 includes external threads 920 associated therewith. In one configuration, the external threads 920 are disposed about a collar 922 of the lead 900. The external threads 920 are adapted to engage with internal threads 926 disposed within a housing 924 of the lead 900. The external threads 920 provide a helical path for the internal threads 926. The movement assembly 902 is not, however, limited to the components described herein. For instance, the external threads 920 and the internal threads 926 can be provided on alternative components, and still be considered within the scope of the invention.

In one configuration, an insert 930 is provided for the internal threads 926, as shown in FIG. 40. The insert 930 contains internal threads 926 which are adapted to engage with the external threads 920 of the collar 922. Although internal and external threads are described, other equivalent movement assemblies can also be incorporated such as those incorporating a track. During use, the terminal pins (discussed above) are rotated which causes the collar 922 to rotate. As the collar 922 is rotated and the external threads 920 and the internals threads 926 engage, the active fixation element 970 moves along the axis of the lead 900. The movement assembly 902 can be used with a wide variety of leads implementing active fixation, including, but not limited to, single pass dual chamber pacing leads, single pass dual chamber pacing/defibrillator leads, single chamber pacing leads, and single chamber pacing/defibrillator leads.

Referring again to FIG. 39, a mesh screen 940 is provided in another embodiment. The mesh screen 940 allows for better tissue in-growth, as well as enhanced sensing capabilities. The mesh screen 940 is disposed proximate to the active fixation element 970. In one embodiment, as the active fixation element 970 is translated and extended from the lead 900, mesh screen 940 moves with the active fixation element 970. The fixation element 970 engages the heart tissue and draws the mesh screen 940 into contact with the surface of the heart.

In another configuration, the lead 900 is provided with a medication distribution member which is adapted to release medicine after the lead 900 has been implanted into a patient. In one embodiment, the medication distribution member comprises a steroid plug 942 which is provided proximate to the mesh screen 940. The steroid plug 942 is located behind the mesh screen 940 relative to the heart. In another embodiment, the medication distribution member comprises a medication collar 943 to release drugs, such as a steroid medication. Drugs can be provided which prevent tissue inflammation after the electrode has been attached to the heart or which assist in blood clotting, or assist in providing other treatments.

In yet another embodiment, the lead, as described above and below, has an increased impedance or a high impedance which can act to extend the life of the battery. The discussion of leads having a curved portion in related co-pending application entitled HIGH IMPEDANCE ELECTRODE TIP, Ser. No. 09/121,288, filed even date herewith, Attorney Docket No. 279.093US1, is hereby incorporated by reference in its entirety. It should be noted that, in an alternative embodiment, the below discussed high impedance embodiments can also be combined with the above described lead embodiments including, but not limited to multi-site pacing for one or more chambers of the heart, bifurcated leads, and leads having curved portions. There are a number of ways in which increased impedance may be effected for mechanically fastened electrode connections in atrial/ventricular implantable catheters (AVIC) systems. These include at least the following: 1) a fully insulated tissue engaging tip (at least with respect to all surfaces that are in electrical contact or electrically active physical relationship to heart muscles so that a pace would be effective if discharged at that portion of the tip), 2) a partially insulated (only a portion of the surface area of the engaging tip being insulated, preferably there is sufficient coating so that at there is at least 5%, or at least 10%, or at least 20 or 30%, or at least 40, 50 or 60%, or at least 70, 75, 80 or 90% of the surface area of the tip which can discharge to heart muscle [or as percentages of the entire tip or as percentages of the entire tip that extends physically beyond the end plane of the catheter and which may therefore penetrate tissue or muscle]), 3) a porous, electrically conductive element, such as a mesh or screen of material at the proximal end of the helix or the distal end of the lead (excluding the helix), at the base of an extended engaging tip, 4) the selection of materials in the composition of the mesh and/or tip which provide higher impedance, 5)

the partial insulative coating of a porous conductive element, such as the mesh or screen to increase its impedance, and 6) combinations of any of these features. There may be various constructions to effect the increased or high impedance, including the use of helical tips with smaller surface areas (e.g., somewhat shorter or thinner tips). There may also be other elements associated with the catheter and/or leads, such as a sheath of material inert to body materials and fluids, circuitry, microcatheters, and at least one conductor extending through the lead body.

One aspect of the present invention comprises an implantable electrode with a helical tip comprising:

an electrode having a distal end and a proximal end; and a helix disposed within the electrode, which helix is aligned along a radial axis of the electrode towards the distal end, and which helix is either retractable or fixed; and the implantable electrode having at least one feature selected from the group consisting of:
  a) the helix having a coating of an insulating material on its surface which covers at least 5% of its surface area but less than 95% of its surface area (which is exposed beyond the distal end of the electrode),
  b) the helix extending beyond the distal end of the electrode and the distal end of the electrode having a porous conductive surface at a base of the helix,
  c) a porous conductive element such as a screen or mesh at a base of the helix, which is retractable/extendable, with the helix being either active or inactive (electrically), and
  d) a partially insulated (partially insulation coated) porous conductive element (e.g., screen or mesh) at the base of an active or inactive, retractable/extendable or fixed helix.

The implantable electrode preferably has the helix with a coating of insulating material on it surface which covers from 5–100% (to 100% where there is an additional electrode element within the system) or 5–95% of surface area of the helix beyond the distal end of the electrode, or surface of the helix which can be considered to be in electrically discharge-functional physical relationship with tissue or muscle into which it is embedded. For purposes of measuring or determining the distal end of the electrode, the tip extends beyond a tubular or cylindrical housing or structural portion which is considered the electrode, and the tip is an engaging portion that extends beyond the housing portion of the electrode. The distal end of the electrode is usually characterized as the end of the cylindrical housing or tubing carrying the tip, circuits, conductive elements, guides, etc. It is more preferred that the helix of the implantable electrode has a coating of insulating material on it surface which covers from 5–95% or 10–90% of the surface area of said helix beyond the distal end of the electrode.

A lead 1010 is illustrated in FIG. 1. The lead 1010 comprises a lead body 1011, an elongate conductor 1013 contained within the lead body, and a lead tip 1020 with an optional retractable tip assembly 1024 contained in the lead tip 1020. In addition, a stylet 1014 is shown inserted into the lead body 1011. A helix 1100 (FIGS. 42A–45A), which consists of an electrical conductor coil, is contained in the retractable lead tip 1024. In an alternative practice of the invention, the helix 1100 extends and retracts by rotation of the stylet 1014, as will be discussed further below. A Brady lead body is shown, although the invention could be incorporated with other leads, such as Tachy leads. The lead body 1011 consists of electrical conductors 1013 which are covered by a biocompatible insulating material 1022. Polymers, such as silicone rubber, fluorinated resins, polyacrylates, polyamides ceramic or composite materials or other insulating material can be used for covering the lead body 1011.

In one embodiment shown in FIG. 43A and 43B, the helix 1100 is formed of electrically conductive material offering low electrical resistance and also resistant to corrosion by body fluids. A biocompatible metal, such as titanium or platinum-iridium alloy is an example of a suitable material. Alternatively, the helix 1100 is electrically inactive or insulated. In one embodiment, the helix 1100 may be coated with an insulative material (not shown) or may be constructed of a rigid, corrosion resistant, non-electrically-conductive material (e.g., a ceramic). A housing 1182, described in further detail below, is made from an electrically conductive material and covered with an insulating material such as a synthetic or natural polymer such as a silicone rubber. The housing 1182 is directly connected to an electrical conductor within the lead 1120. These materials are additionally suitable because they tend to be biologically inert and well tolerated by body tissue.

The helix 1100 defines a lumen and thereby is adapted to receive a stiffening stylet 1014 that extends through the length of the lead. The stylet 1014 stiffens the lead 1120, and can be manipulated to introduce an appropriate curvature to the lead, facilitating the insertion of the lead into and through a vein and through an intracardiac valve to advance the distal end of the lead 1120 into the right ventricle of the heart (not shown). A stylet knob 1154 is coupled with the stylet 1014 for rotating the stylet 1014 and advancing the helix 1100 into tissue of the heart.

Figure 42B:
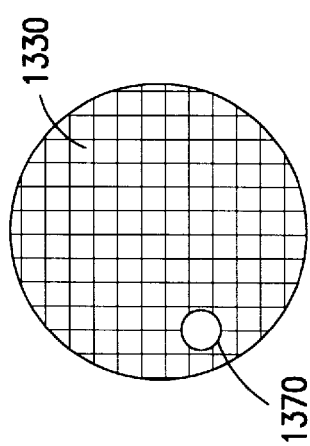
FIG. 42B is an end view of the electrode tip of the lead shown in FIG. 42A.
Figure 42A:
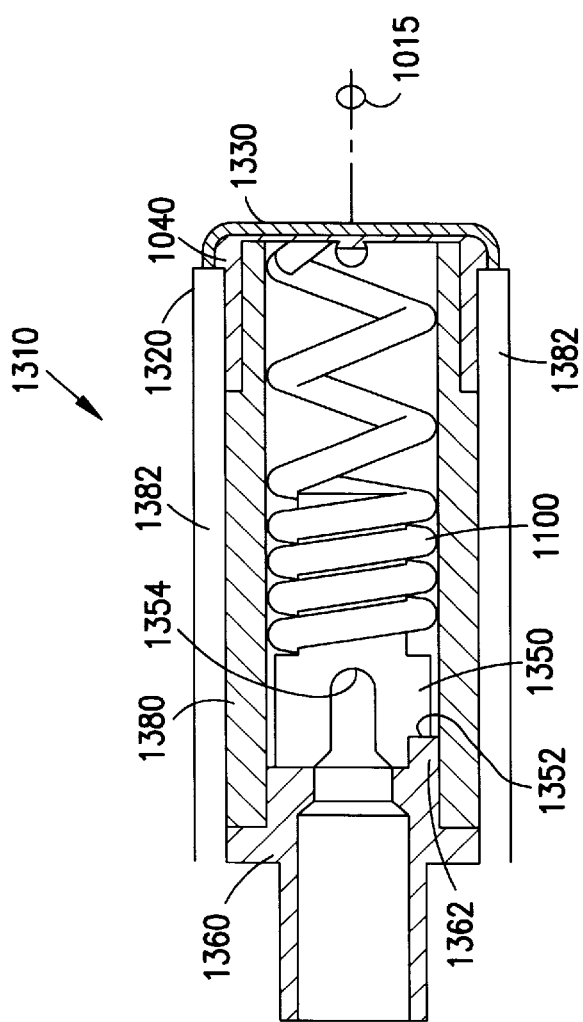
FIG. 42A is a cross-sectional view of an electrode tip of a lead for monitoring and stimulating the heart constructed in accordance with one embodiment of the present invention.

In one embodiment, as shown in FIGS. 42A and 42B, a lead 1310 has an electrode tip 1320 which is provided with a mesh screen 1330. The mesh screen 1330, in one embodiment, completely encapsulates the diameter of the lead, and may serve, at least in part, as a pacing/sensing interface with cardiac tissue. If the helix 1100 is electrically active, it too can help serve as a portion of a pacing or sensing interface. The mesh screen 1330 is of a porous construction, preferably made of electrically conductive, corrosion resistant material. Using a mesh screen 1330 having a porous construction allows for fibrotic ingrowth. This provides for a further anchoring of the lead tip 1320 and also increases the sensing capability of the lead 1310 by increasing the surface area in contact with the cardial tissue. The mesh screen 1330 may be attached to an electrode collar 1040, which is electrically active. In a retractable catheter system, a housing 1380, which is electrically conductive, encapsulates the piston 1350 and the fixation helix 1100. Insulation 1382 is disposed about the housing 1380 and collar 1040.

Disposed within the lead 1310 is a lead fastener 1100 for securing the lead 1310 to cardiac tissue. The lead fastener 1100 can be disposed along the radial axis 1015 of the electrode lead 1310. In this embodiment, the lead fastener 1100 comprises a fixation helix 1100. The fixation helix 1100 can be made electrically active or inactive as discussed above. Attached to the fixation helix 1100 in a retractable tip system is a piston 1350. The piston 1350 is configured to mate with a bladed locking stylet 1014 at a stylet slot 1354, and acts as an interface between the stylet 1014 and the helix 1100. The stylet 1014, coupled with the piston 1350 at the stylet slot 354, extends and retracts the fixation helix 1100 when the stylet 1014 is rotated. The piston 1350 can either be electrically active or inactive. The piston 1350 also has a slot 1352, which allows the piston 1350 to mate with a base 1360.

Fitted with a knob 1362, as shown in FIG. 42A, the base 1360 mates with the slot 1352 of the piston 1350. The base 1360 serves as a stop once the fixation helix 1100 is fully retracted. The electrically conductive base 1360 also allows passage of a bladed locking stylet 1014 and attachment of electrode coils (not shown).

In addition, the lead 1310 has a guide groove 1370. The groove 1370 is formed, in one embodiment, by puncturing a hole (not shown) within the mesh screen 1330, although the guide groove 1370 can be formed by other methods known by those skilled in the art. Having a circular cross-section, the guide groove 1370 may have a diameter greater than that of the conductor forming the helix 1100. The groove 1370 is disposed within the mesh screen 1330, and directs the fixation helix 1100 from its retracted position, as illustrated in FIG. 42A, to an extended position (not shown). The groove 1370 also reversibly directs the fixation helix 1100 from an extended position to the retraction position.

In a second embodiment, as shown in FIGS. 43A and 43B, a lead 1110 has an electrode tip 1120 which is provided with a mesh screen 1130. The mesh screen 1130 completely encapsulates the diameter of the lead or electrode tip 1120, and serves as the pacing/sensing interface with cardiac tissue. The screen 1130 is of a porous construction, made of electrically conductive, corrosion resistant material. Using a mesh screen 1130 having a porous construction allows for fibrotic ingrowth. This provides for a further anchoring of the lead tip 1120 to tissue and also increases the sensing capability of the lead 1110. The sensing capability is enhanced because the mesh screen 1130 has more surface area than corresponding solid material. The ingrowth of fibrotic tissue into the mesh screen 1130 increase the sensing capability of the lead 1110 by increasing the surface area in contact with the cardial tissue. Furthermore, the geometry of the mesh screen 1130, particularly any protuberance, as will be discussed below, creates a high pacing impedance tip.

The mesh screen 1130 may form a protuberance 1135 from a flat edge portion 1137 of the mesh screen 1130 in a generally central portion of the electrode tip 1120. The protuberance 1135 may be generally circular in cross-section, but may be any shape (e.g., truncated cylindrical, truncated pyramidal, oval, ellipsoidal, etc.) as a result of design or circumstance which provides a flat or conformable surface (preferably not a rigid, sharp face which will not conform to tissue) abutting tissue, and preferably has a diameter smaller than a diameter of the lead 1110 (although a larger. In addition, the protuberance 1135 is aligned with the radial axis 1015 of the lead 1110. Sintered to an electrode collar 1040, a process known by those skilled in the art, the mesh screen 1130 is attached to the electrode tip 1120. The electrode collar 1040 is electrically active.

Disposed within the electrode lead 1110 is a lead fastener for securing the electrode lead 1110 to cardiac tissue. The lead fastener can be disposed along the radial axis 1015 of the electrode lead 1110. In this embodiment, the lead fastener comprises a fixation helix 1100. The fixation helix 1100 can be made electrically active or inactive to change sensing and pacing characteristics, as discussed above. Attached to the fixation helix 1100 is a piston 1150. The piston 1150 is configured to mate with a bladed locking stylet 1014, thereby providing a movement assembly. The stylet 1014 extends and retracts the fixation helix 1100 when the stylet 1014 is rotated. The piston 1150 can either be electrically active or inactive. The piston 1150 also has a slot 1152. The slot 1152 of the piston 1150 allows the piston 1150 to mate with a base 1160 upon full retraction.

The base 1160 is modified with a knob 1162 to mate with the slot 1152 of the piston 1150. The knob 1162 mates with the piston 1150 to prevent over-retraction once the helix 1100 has been fully retracted. The stylet 1014 operates to advance the fixation helix 1100. As the implanter rotates the stylet 1014, the stylet 1014 engages the piston 1150 at the stylet slot 1154 and rotates the piston 1150, which moves the fixation helix 1100 through a guide groove 1170. The guide groove 1170 is for ensuring that the fixation helix 1100 is properly guided out of and into the end of the electrode. Once the fixation helix 1100 is fully retracted, the base 1160 serves as a mechanical stop. The base 1160 also allows passage of a bladed locking stylet 1014 and attachment of electrode coils. Additionally, the base 1060 is electrically active. The electrode lead 1110 also has a guide groove 1170. The groove 1170 is formed by puncturing a hole within the mesh screen. Having a circular cross-section, the groove 1170 has a diameter greater than that of the conductor forming the helix 1100. The groove 1170 is disposed within the mesh screen 1130, and directs the fixation helix 1100 from its retracted position, as illustrated in FIG. 42A, to an extended position (not shown). During implantation, after the electrode is in contact with tissue at the desired location in the heart, the stylet 1014 is rotated which causes the piston to advance the fixation helix out of the groove 1170. As the fixation helix 1100 is placed in an extended position, the helix 1100 travels through groove 1170 and circles around the protuberance 1135. The groove 1170 also directs the fixation helix 1100 from an extended position to the retracted position. Advantageously, the mesh screen 1130 prevents the implanter from overextension and advancing the helix 1100 too far into the tissue. An electrically conductive housing 1180 encapsulates both the piston 1050 and the fixation helix 1100. Insulation 1182 covers the housing 1180, the collar 1040, and a portion of the mesh screen 1130. The insulation 1182 over the mesh screen 1130 controls the impedance of the electrode tip 1120.

Figure 44B:
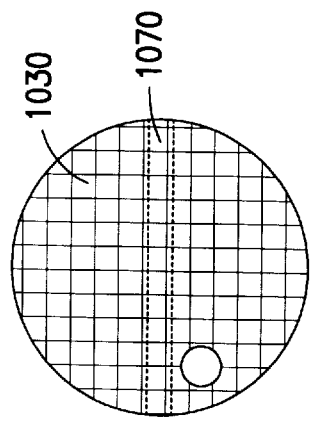
FIG. 44B is an end view of the electrode tip of the lead shown in FIG. 44A.
Figure 44A:
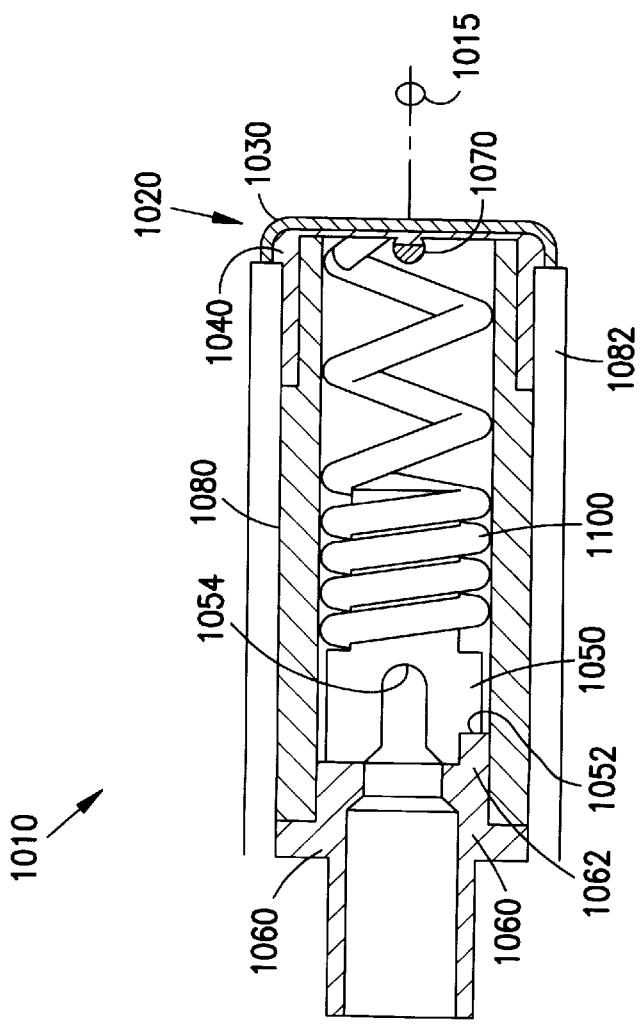
FIG. 44A is a cross-sectional view of an electrode tip of a lead for monitoring and stimulating the heart constructed in accordance with one embodiment of the present invention

In a third embodiment as shown in FIGS. 44A and 44B, a lead 1010 has an electrode tip 1020 which is provided with a mesh screen 1030. The mesh screen 1030 completely encapsulates the diameter of the lead tip. Sintered to an electrode collar 1040, the mesh screen 1030 is attached to the electrode tip 1020. The electrode collar 1040 is electrically active. A housing 1080 is disposed about the helix 1100, and is electrically active. Insulation 1082, encompasses the housing 1080 and collar 1040.

In one embodiment, as shown in FIGS. 42A and 42B, a lead 1310 has an electrode tip 1320 which is provided with a mesh screen 1330. The mesh screen 1330 completely encapsulates the diameter of the lead, and serves as the pacing/sensing interface with cardiac tissue. If the helix 1100 is electrically active, it too can help serve as a pacing or sensing interface. The mesh screen 1330 is of a porous construction, made of electrically conductive, corrosion resistant material. Using a mesh screen 1330 having a porous construction allows for fibrotic ingrowth. This provides for a further anchoring of the lead tip 1320 and also increases the sensing capability of the lead 1310 by increasing the surface area in contact with the cardial tissue. The mesh screen 1330 is attached to an electrode collar 1040, which is electrically active. A housing 1380, which is electrically conductive, encapsulates the piston 1350 and the fixation helix 1100. Insulation 1382 is disposed about the housing 1380 and collar 1040.

Disposed within the lead 1310 is a lead fastener for securing the lead 1310 to cardiac tissue. The lead fastener can be disposed along the radial axis 1015 of the electrode lead 1310. In this embodiment, the lead fastener comprises a fixation helix 1100. The fixation helix 1100 can be made electrically active or inactive as discussed above. Attached to the fixation helix 1100 is a piston 1350. The piston 1350 is configured to mate with a bladed locking stylet 1014 at a stylet slot 1354, and acts as an interface between the stylet 1014 and the helix 1100. The stylet 1014, coupled with the piston 1350 at the stylet slot 1354, extends and retracts the fixation helix 1100 when the stylet 1014 is rotated. The piston 1350 can either be electrically active or inactive. The piston 1350 also has a slot 1352, which allows the piston 1350 to mate with a base 1360.

Fitted with a knob 1362, as shown in FIG. 42A, the base 1360 mates with the slot 1352 of the piston 1350. The base 1360 serves as a stop once the fixation helix 1100 is fully retracted. The electrically conductive base 1360 also allows passage of a bladed locking stylet 1014 and attachment of electrode coils.

In addition, the lead 1310 has a guide groove 1370. The groove 1370 is formed by puncturing a hole within the mesh screen, although the guide groove can be formed by other methods known by those skilled in the art. Having a circular cross-section, the groove 1370 has a diameter greater than that of the conductor forming the helix 1100. The groove 1370 is disposed within the mesh screen 1330, and directs the fixation helix 1100 from its retracted position, as illustrated in FIG. 42A, to an extended position (not shown). The groove 1370 also directs the fixation helix 1100 from an extended position to the retraction position.

In a second embodiment, as shown in FIGS. 43A and 43B, a lead 1110 has an electrode tip 1120 which is provided with a mesh screen 1130. The mesh screen 1130 completely encapsulates the diameter of the lead tip, and serves as the pacing/sensing interface with cardiac tissue. The screen 1130 is of a porous construction, made of electrically conductive, corrosion resistant material. Using a mesh screen 1130 having a porous construction allows for fibrotic ingrowth. This provides for a further anchoring of the lead tip 1120 and also increases the sensing capability of the lead 1110. The sensing capability is enhanced because the mesh screen 1130 has more surface area than corresponding solid material. The ingrowth of fibrotic tissue into the mesh screen 1130 increase the sensing capability of the lead 1110 by increasing the surface area in contact with the cardial tissue. Furthermore, the geometry of the mesh screen, particularly the protuberance, as will be discussed below, creates a high pacing impedance tip.

The mesh screen 1130 forms a protuberance 1135 from a flat edge portion 1137 of the mesh screen 1130 in a generally central portion of the electrode tip 1120. The protuberance 1135 is generally circular in cross-section, and has a diameter smaller than a diameter of the lead 1110. In addition, the protuberance 1135 is aligned with the radial axis 1015 of the lead 1110. Sintered to an electrode collar 1040, a process known by those skilled in the art, the mesh screen 1130 is attached to the electrode tip 1120. The electrode collar 1040 is electrically active.

Disposed within the electrode lead 1110 is a lead fastener for securing the electrode lead 1110 to cardiac tissue. The lead fastener can be disposed along the radial axis 1015 of the electrode lead 1110. In this embodiment, the lead fastener comprises a fixation helix 1100. The fixation helix 1100 can be made electrically active or inactive to change sensing and pacing characteristics, as discussed above. Attached to the fixation helix 1100 is a piston 1150. The piston 1150 is configured to mate with a bladed locking stylet 1014, thereby providing a movement assembly. The stylet 1014 extends and retracts the fixation helix 1100 when the stylet 1014 is rotated. The piston 1150 can either be electrically active or inactive. The piston 1150 also has a slot 1152. The slot 1152 of the piston 1150 allows the piston 1150 to mate with a base 1160 upon full retraction.

The base 1160 is modified with a knob 1162 to mate with the slot 1152 of the piston 1150. The knob 1162 mates with the piston 1150 to prevent over-retraction once the helix 1100 has been fully retracted. The stylet 1014 operates to advance the fixation helix 1100. As the implanter rotates the stylet 1014, the stylet 1014 engages the piston 1150 at the stylet slot 1154 and rotates the piston 1150, which moves the fixation helix 1100 through a guide groove 1170. The guide groove 1170 is for ensuring that the fixation helix 1100 is properly guided out of and into the end of the electrode. Once the fixation helix 1100 is fully retracted, the base 1160 serves as a mechanical stop. The base 1160 also allows passage of a bladed locking stylet 1014 and attachment of electrode coils. Additionally, the base 1060 is electrically active.

The electrode lead 1110 also has a guide groove 1170. The groove 1170 is formed by puncturing a hole within the mesh screen. Having a circular cross-section, the groove 1170 has a diameter greater than that of the conductor forming the helix 1100. The groove 1170 is disposed within the mesh screen 1130, and directs the fixation helix 1100 from its retracted position, as illustrated in FIG. 42A, to an extended position (not shown). During implantation, after the electrode is in contact with tissue at the desired location in the heart, the stylet 1014 is rotated which causes the piston to advance the fixation helix out of the groove 1170. As the fixation helix 1100 is placed in an extended position, the helix 1100 travels through groove 1170 and circles around the protuberance 1135. The groove 1170 also directs the fixation helix 1100 from an extended position to the retracted position. Advantageously, the mesh screen 1130 prevents the implanter from overextension and advancing the helix 1100 too far into the tissue. An electrically conductive housing 1180 encapsulates both the piston 50 and the fixation helix 1100. Insulation 1182 covers the housing 1180, the collar 40, and a portion of the mesh screen 1130. The insulation 1182 over the mesh screen 1130 controls the impedance of the electrode tip 1120.

In a third embodiment as shown in FIGS. 44A and 44B, a lead 1010 has an electrode tip 1020 which is provided with a mesh screen 1030. The mesh screen 1030 completely encapsulates the diameter of the lead tip. Sintered to an electrode collar 1040, the mesh screen 1030 is attached to the electrode tip 1020. The electrode collar 1040 is electrically active. A housing 1080 is disposed about the helix 1100, and is electrically active. Insulation 1082, encompasses the housing 1080 and collar 1040.

Disposed within the lead 1010 is a lead fastener for securing the lead 1010 to cardiac tissue. The lead fastener can be disposed along the radial axis 1015 of the lead 1010. In this embodiment, the lead fastener comprises a fixation helix 1100. The fixation helix 1100 can be made electrically active or inactive to change sensing and pacing characteristics.

The helix 1100 is of a well known construction. Using a conductor coil such as helix 1100 has been shown to be capable of withstanding constant, rapidly repeated flexing over a period of time which can be measured in years. The helix 1100 is wound relatively tightly, with a slight space between adjacent turns. This closely coiled construction provides a maximum number of conductor turns per unit length, thereby providing optimum strain distribution. The spirally coiled spring construction of helix 1100 also permits a substantial degree of elongation, within the elastic limits of the material, as well as distribution along the conductor of flexing stresses which otherwise might be concentrated at a particular point.

Attached to the fixation helix 1100 is a piston 1050. The piston 1050 is configured to mate with a bladed locking stylet 1014. The piston 1050 advances the fixation helix 1100 once the lead is placed in position within the heart. The piston 1050 can either be electrically active or inactive. The piston 1050 also has a slot 1052 and a stylet slot 1054. The stylet 1014 couples with the stylet slot 1054 and extends or retracts the fixation helix 1100 when the stylet 1014 is rotated. The slot 1052 of the piston 1050 allows the piston 1050 to mate with a base 1060 when the helix 1100 is retracted to prevent over retraction. The base 1060 is configured with a knob 1062 to mate with the slot 1052 of the piston 1050. Once the fixation helix 1100 is fully retracted, the base 1060 serves as a stop at full retraction. The base 1060 also allows passage of a bladed locking stylet 1014 and attachment of electrode coils. In addition, the base 1060 is electrically active.

The lead 1010 also includes a guiding bar 1070. Extending across the diameter of the tip, the guiding bar 1070 is generally cylindrical in shape. The guiding bar 1070 directs the fixation helix 1100 from its retracted position, as illustrated in FIG. 42A, to an extended position (not shown) as the piston 1052 advances the helix 1100. The guiding bar 1070 also directs the fixation helix 1100 as it is retracted from an extended position to the retraction position through the mesh screen. Although a guiding bar 1070 is described, other types of guiding mechanisms can be used such as helical passageways, threaded housings, springs, and are considered within the scope of the invention. Additionally, the lead 1010 is provided with a seal (not shown) for preventing entry of body fluids and tissue from entering the lead through the opening therein. The seal could be a puncture seal between the piston 1050 and the base 1060. Alternatively, O-rings could be used to seal the electrode.

In a fourth embodiment as shown in FIGS. 45A and 45B, a lead 1210 has an electrode tip 1220 which is provided with a mesh screen 1230. The mesh screen 1230 forms an annular ring having an open center, where the annular ring is centered at a radial axis 1015 of the electrode lead 1210. The mesh screen 1230 provides more surface area than a smooth tipped electrode which aids in sensing. The removal of the center portion of the mesh screen creates a high impedance pacing tip due to the nature of the surface geometry. Sintered, fused, bonded, adhesively secured or mechanically attached to an electrode collar 1040, the mesh screen 1230 is attached to the electrode tip 1220. The electrode collar 1040 is electrically active.

Disposed within the lead 1210 is a lead fastener for securing the lead 1210 to cardiac tissue. The lead fastener can be disposed along the radial axis 1015 of the electrode lead 1210. In this embodiment, the lead fastener comprises a fixation helix 1100. The fixation helix 1100 can be made electrically active or inactive as discussed above. Attached to the fixation helix 1100 is a piston 1250. The piston 1250 has a stylet slot 1254 and is configured to mate with a bladed locking stylet 1014. The stylet 1014, coupled with the piston 1250 at the stylet slot 1254, extends and retracts the fixation helix 1100 when the stylet 1014 is rotated. The piston 1250 can either be electrically active or inactive. The base 1260 serves as a stop once the fixation helix 1100 is fully retracted. The base 1260 also allows passage of a bladed locking stylet 1014 and attachment of electrode coils. The base 1060 is electrically active.

Additionally, the lead also has a guiding bar 1270. The guiding bar 1270 directs the fixation helix 1100 from its retracted position, as illustrated in FIGS. 45A and 45B, to an extended position (not shown). The guiding bar 1270 also directs the fixation helix 1100 from an extended position to the retracted position. Although a guiding bar 1270 has been described, other types of mechanisms could be used to extend the helix, and are considered within the scope of the invention. A housing 1280 encapsulates the piston 1250 and the fixation helix 1100, and insulation 1282 is disposed over the housing 1280 and collar 1040.

Insulation generally covers the housing, the collar, and a portion of the electrical discharge surface (e.g., the cathode, the helix and/or the porous material or mesh). The insulation over the mesh screen further controls the impedance of the electrode tip. The insulated coating, whether present on the helix or the mesh or other elements which are potentially electrically active or on which electrical activity is to be suppressed, should be biocompatible, non-thrombogenic, and otherwise safe for implantation. The insulation coating should be of dimensions which effect the insulation, increase the impedance (where desired), but which dimensions do not interfere with the performance of the tip, the lead or the helix or the health of the patient. The insulation is present as a coating (a material which tends to conform to the surface rather than completely reconfigure it, as would a lump of material). The coating usually should be at least 0.5 microns in thickness, usually between 0.5 and 100 microns, preferably between 1.0 and 30 or 50 microns, more preferably between 1 and 20 microns, still more preferably between 1.5 and 15 microns, and most preferably between 1.5 or 2.0 microns and 10 or 15 microns. The coating may be provided by any convenient process, such as electrophoretic deposition, dip coating, spin coating, in situ polymerization, vapor deposition, sputtering and the like. Any insulating material is useful, such as polymers, ceramics, glasses, and the like, but because of their convenience in application, flexibility and availability, polymers are preferred. Polymers from such classes as polyesters, polyamides, polyurethanes, polyethers, polysiloxanes, polyfluorinated resins, polyolefins, polyvinyl polymers, polyacrylates (including polymethacrylates), and the like may be used with various leads and tips according to the practice of the present invention. Parylene is a preferred material, as described herein, with a thickness of between 1.5 and 10 microns.

In yet another embodiment, a partially insulated fixation helix is used to provide a relatively high impedance electrode design. Leads comprising a distal or electrode end and a proximal or connector end may be used. A "miniature" wire-in-basket porous electrode may be sintered upon the distal end of a metallic pin, provided with a blind hole. Circumferential to this subassembly, a sharpened wire fixation helix may be positioned and attached at a general location proximal to the electrode by any convenient means which allows electrical continuity. This attachment includes, but is not limited to, crimping, spot welding, laser welding, the use of grooves upon the surface of the pin, the use of thin metallic overband (also not shown) or any combination thereof. A portion of this fixation helix is provided with an extremely thin layer of a biostable, biocompatible polymer, which, inter alia, provides electrical insulation between the fixation helix and the cardiac tissue. In one embodiment, the insulated portion is the majority of the fixation helix, leaving a relatively small uninsulated region of fixation helix. This approach offers increased impedance to reduce energy dissipation in pulsing functions, such as pacing functions. Other varying embodiments include, but are not limited to, a portion which is approximately or substantially equal to half of the fixation helix, and a portion which is approximately or substantially equal to a minority of the fixation helix. Such embodiments provide different amounts of uninsulated region and different amounts of impedance. The thin coating of electrically insulating coating must usually be at least 1 micron in thickness to provide a significant insulating effect, depending upon its insulating ability and properties. The thickness of the coating is limited primarily by physical limitations on the system. The coating can not be so thick as to interfere with the fastening ability of the helix or to increase the size of the helix beyond that which is tolerable for the use of the helix and the patient. Typically, the coating is at least one micron up to about 100 microns, more typically the coating is between 1 and 30 microns, preferably between 1.5 and 20 microns, more preferably between 1.5 and 15 microns, and most preferably between 2 and 10 microns. The material used for the coating should, of course, be biocompatible and even more preferably non-thrombogenic. Materials such as Parylene TM, polyurethanes, polyacrylates (including polymethacrylates), polyesters, polyamides, polyethers, polysiloxanes, polyepoxide resins and the like can be used. Crosslinked polymers within these classes may be preferred for their resistance to breakdown and their physical durability. As the coating is to be maintained within the body of a recipient, the coating composition should not be water-soluble or aqueous soluble within the parameters and environment encountered within animal bodies (e.g., it should not be soluble within blood, serum or other body fluids with which it might come into contact).

To the proximal end of this pin, a metallic conductor coil may be conveniently attached to provide electrical connection to the implantable pacemaker (not shown) by means of a connector. In one embodiment, local (e.g., steroid or other medicinal) therapy is provided by a (e.g., circumferential) steroid/polymer matrix positioned immediately proximal to the porous electrode. In one embodiment, the circumferential steroid/polymer matrix is provided with a distal taper. Other embodiments include other distal configurations, including, but not limited to, non-tapered or "inflated" configurations. In one embodiment, an internalized, medicinal or biologically active (e.g., steroid) releasing matrix is used. Proximal to this biologically active (e.g., steroid) eluting matrix, a generally cylindrical polymeric tubing (this is the preferred shape, but the shape is a matter of choice) 1820 is used to provide electrical insulation of this entire assembly. In one embodiment the lead is "unipolar." In one embodiment an ablative protective covering positioned over the entirety of distal end 520 is used (not shown). One example of such a covering is the mannitol "Sweet Tip"™ electrode of Cardiac Pacemaker, Inc. CPI/Guidant. In one embodiment, a "bipolar" lead is provided with the distal electrode features described.

During an in vitro evaluation of this electrode design, polymeric coatings intended to partially insulate the fixation helix were prepared and evaluated. In one embodiment, the Parylene coating is extremely thin (~3$\mu$), providing a coating with uniform coverage which is adherent to the metallic substrate, and which is controllable to provide an abrupt margin. The silicone rubber coating is known to be somewhat thicker (~10$\mu$), uniform in coverage, somewhat less adherent to the metallic substrate, and controllable to an abrupt margin. Other coatings may be used without departing from the spirit and scope of the present invention.

The Parylene or other insulative coating effectively increases in vitro "pacing impedance." Application of a non-continuous or partially extensive coating of an electrically insulating polymer such as Parylene to the metallic fixation helix produces the desired increase in impedance compared to an uninsulated helix as well as other existing designs. For example, it has been demonstrated that one embodiment using a coated fixation helix provides a pacing impedance of over approximately 800 ohms which is larger than the impedance of some electrodes using an uncoated fixation helix. The post-implant pacing impedance of an embodiment using a coated fixation helix remains higher than that of typical electrodes using an uncoated fixation helix. In one experiment, a coated fixation helix using Parylene as an insulating layer provided over 1200 ohms average pacing impedance on the day of implantation and over 900 ohms ten days after the implant.

Additionally, post-implant average voltage threshold of the Parylene insulated miniaturized electrode is less than the other high impedance electrodes. Such performance is considered to be desirable. In one experiment, an embodiment with a coated fixation helix 1804 having a voltage threshold of approximately 0.2 volts on the day of implant was measured at about 0.7 volts at ten days after the implant (using a 0.5 ms pulse width). An electrode with an uncoated fixation helix demonstrated over 0.8 volts average voltage threshold at ten days after the implant, illustrating the benefits of the coated fixation helix.

An additional benefit is that the coated fixation helix embodiments may provide an improvement in both the implant as well as post-implant average S-wave amplitude detection.

The miniaturized high impedance, positive fixation porous electrode technology described here provides the following advantages over the prior art. For one example, the coated fixation helix embodiments provide an electrode where the benefits of high impedance pacing are realized through downsizing the porous electrode and insulating the fixation helix. Downsizing of the porous electrode may be accomplished, for example, by having a smaller porous (e.g., mesh) electrode supported on a non-conductive surrounding support element (e.g., a polymeric or composite film with a mesh central area, particularly a mesh truncated conical or pyramidal area of flexible, conductive mesh). An area of the completely conductive mesh may also be discontinuously coated leaving a conductive central or conductive raised area, particularly surrounding a contact, engaging element, or helix. Further, an external steroid collar provides a fabrication advantage since such a component can be readily mass produced compared to smaller components with elaborate profiles. Still further, fabrication of a lead with this external collar is streamlined. The higher impedance design conserves battery power to provide longer battery life with fewer battery replacements. Other benefits exist which are not described in detail herein, however, which those skilled in the art will appreciate.

Figure 46:
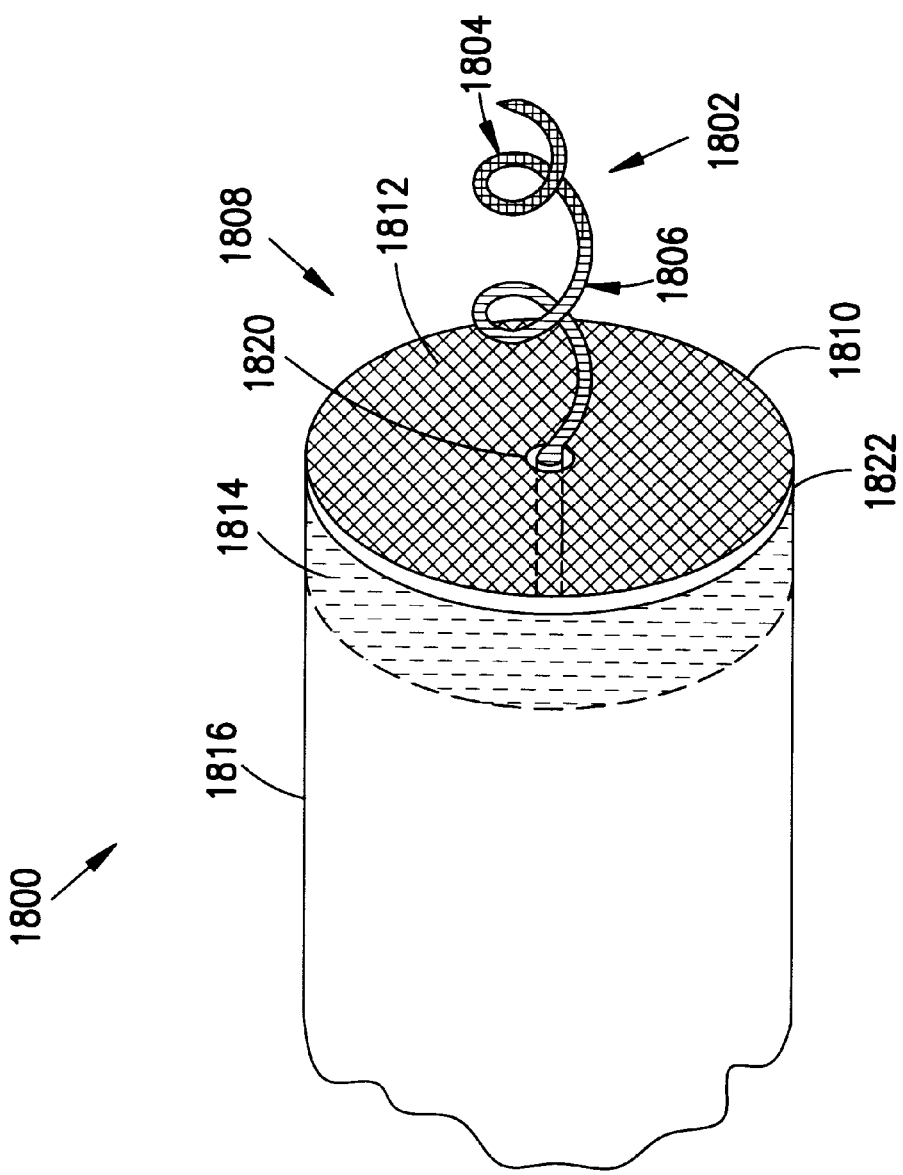
FIG. 46 shows a partially insulated helical tip constructed in accordance with one embodiment of the present invention.

FIG. 46 shows a high impedance catheter tip 1800 with a partially insulated tip 1802 and a partially insulated mesh 1808. The partially insulated tip (or helix) 1802 comprises one fully insulated section 1804 and one uninsulated section 1806. The partially insulated mesh 1808 comprises a first area 1810 of the mesh 1808 which is insulated and second are 1812 of the mesh 1808 which is not insulated. The impedance of the catheter tip can be readily controlled by the amount of surface area of the helical tip itself and the area of the mesh (if present) which is insulated. With a fixed conductivity in the tip and the mesh (if present), the impedance can be increased by increasing the percentage of the surface area of the tip or mesh which is insulated.

A hole 1820 is shown in the mesh 1808. The mesh 1808 may be flat and flush with the end 1822 of the catheter 1816 or may be partially wrapped (not shown) over the end 1820 or inside the end 1820 to affix the mesh to the catheter 1816. The mesh 1808 may also be hemispherical, truncated conical, truncated pyramidal or any other shape which may assist in allowing the mesh 1808 to more compliantly contact tissue (not shown) surface to transmit the pacing signal or discharge. Within the catheter 1816 may be a soluble, elutable or dispersible material which carries medication or biologically active material along with the catheter. For example, anti-inflammatants, antibiotics, analgesics, pain-reducing medication, vitamins, anti-viral medication, or the like may be transmitted to the attachment site along with the catheter by inclusion within a material 1814 carried within or on the catheter 1816.

The coating of insulation on the helical tip or mesh may be applied by any convenient method, including, but not limited to coating (e.g., dip coating), printing, spraying, brush application, resist application and removal and the like. The insulation may also contain active ingredients (such as those recited within material 1814) to benefit the patient. The insulation carrying the active material must not be soluble, so a polymer or other material that is porous or has elutable materials must be used. The material delivery does not have to be coextensive with the life of the implant or the tip, and delivery of the material may be desirable only over a short time period after insertion of the helical tip and catheter.

A soluble or dispersible protective cap may also be placed over the helical tip to reduce the possibility of any incidental damage while catheterizing or moving the tip within a patient. As previously noted, the cap material should preferably be biocompatible or even digestible and may include such materials as natural and synthetic materials such as sugars, starches, gelation (unhardened), gums, resins, polymers, and the like. All components of the catheter and tip which are exposed to the tissue or fluids within a patient should be non-thrombogenic, and bio-acceptable. There are extensive classes of commercially available materials which meet these needs for metal, polymeric, composite and other materials described within the practice of the present invention.

It is contemplated that slight variations in the design of the lead could be used for a particular application as required. One such variation would be the provision of steroid elution from any of the electrodes provided on the lead. Steroid elution can be provided by using one or more of the steroid-releasing technologies such as sleeves or collars positioned in close proximity to the electrodes or by the use of internalized steroid-containing plugs. Steroids are generally used in order to reduce the inflammation associated with attaching an electrode to the endocardial wall of the heart. By reducing the inflammation at the time of implantation, the threshold values associated with the electrodes are usually lower when compared to threshold values associated with electrodes that did not elute a steroid over the attachment site. An example of the composition of at least one collar is dexamethasone acetate in a simple silicone medical adhesive rubber binder or a steroid-releasing plug similarly fabricated.

Advantageously, the single pass lead allows for one, two, or more chambers of the heart to be paced and/or sensed, while only one lead is implanted within the patient. This assists in preventing added stress and expense for the patient. In addition, the active fixation element will not hook nor snag tissue when it is retracted within the lead. The active fixation element also does not require the use of a stylet, since the terminal pins are used to extend and retract the active fixation element. The active fixation allows for the lead to be positioned almost anywhere in the atrium. The movement assembly assists in protecting the shape of the helix even when the helix is under tension.

It is to be understood that the above description is intended to be illustrative, and not restrictive. Many other embodiments will be apparent to those of skill in the art upon reading and understanding the above description. For example, the present invention can be used with a variety of medical devices. Although the use of the lead has been described for use in a cardiac pacing system, the lead could also be applied to other types of body stimulating systems. It should also be noted that the above described embodiments of the systems and leads include combinations of the various embodiments described herein. The scope of the invention should, therefore, be determined with reference to the appended claims, along with the full scope of equivalents to which such claims are entitled.

What is claimed is:

1. An apparatus comprising:
   a signal generator for producing pulses to apply to a heart;
   a main lead body adapted to carry signals to and from the heart;
   a first electrode having an active fixation portion, said main lead body having a first recess therein housing the first electrode, the first electrode capable of moving between a first recessed position within said first recess and a second extended position outside the first recess so that the active fixation portion of the first electrode can attach to a wall of the heart; and
   a second lead body associated with the main lead body, a second electrode disposed on the second lead body, the first electrode housed within a first chamber of the heart and the second electrode housed within a second chamber in the heart, the second electrode having an active fixation portion, said main lead body having a second recess therein housing the second electrode, the second lead body capable of moving between a first recessed position within said second recess and a second extended position outside the second recess so that the active fixation portion of the second electrode can attach to the wall of the heart.

2. A lead adapted for endocardial implantation in, on or about the heart, said lead comprising:
   a lead body;
   a first electrode attached to the distal end of the lead body; and
   a second electrode attached to the lead body a selected distance away from the first electrode, the portion of said lead body between the first electrode and second electrode having a single continuous curve therein to facilitate positioning of the first electrode and the second electrode within the heart.

3. A system for detecting arrhythmias of the heart and for delivering signals to the heart, said system comprising:
   an electronics system further comprising,
      a cardiac activity sensor; and
      a signal generator which produces signals to stimulate the heart; and
   a lead adapted for endocardial implantation in, on or about the heart and for connection to the electronic system, said lead further comprising:
      a main lead body having a first recess therein;
      a supplemental lead body carrying a first electrode having an active fixation portion, said supplemental lead body capable of being moved between a first position substantially within the first recess, and a second position substantially outside the first recess; and
      a second electrode attached to the main lead body.

4. A lead comprising:
a main lead body adapted to carry signals to and from a heart, the main lead body having a first recess therein;
a first leg associated with the main lead body, the first leg including a first electrode having an active fixation portion, the first leg removably disposed within the first recess; and
a second leg associated with the main lead body, the second leg including a second electrode; and
where the first recess receives the second leg therein.

5. A single pass lead comprising:
a main lead body adapted to carry electrical signals to and from a heart, the main lead body having a lumen therethrough
a first electrode disposed on the main lead body; and
a supplemental lead body having a second electrode, the supplemental lead body rotatably disposed within the lumen of the main lead body.

6. The lead as recited in claim 5, wherein the supplemental lead disposed within an atrium of the heart, and the supplemental lead includes an active fixation mechanism.

7. The lead as recited in 6, wherein the supplemental lead body extends from a terminal end to a distal end, the distal end having a J-shape.

8. The lead as recited in claim 5, wherein the supplemental lead body extends from a terminal end to a distal end, and the supplemental lead body is adapted to be rotated within the main lead body using the terminal end of the supplemental lead body.

9. The lead as recited in claim 5, wherein the lumen extends through the main lead body and ends at an aperture at an intermediate portion of the main lead body, and the aperture is transverse to a longitudinal axis of the main lead body.

10. A single pass lead comprising:
a main lead body adapted to carry electrical signals to and from a heart, the main lead body having a lumen therethrough
a first electrode disposed on the main lead body;
a supplemental lead body having a second electrode, the supplemental lead body movably disposed within the main lead body; and
wherein the lumen extends through the main lead body and ends at an aperture at an intermediate portion of the main lead body, and the aperture is transverse to a longitudinal axis of the main lead body.

11. The lead as recited in claim 10, wherein the supplemental lead is disposed within an atrium of the heart, and the supplemental lead includes an active fixation mechanism.

12. The lead as recited in 11, wherein the supplemental lead body extends from a terminal end to a distal end, the distal end having a J-shape.

13. The lead as recited in claim 10, wherein the supplemental lead body is rotatably disposed within the lumen of the main lead body.

14. The lead as recited in 13, wherein the supplemental lead body extends from a terminal end to a distal end, and the supplemental lead body is adapted to be rotated within the main lead body using the terminal end of the supplemental lead body.

15. A single pass lead comprising:
a main lead body adapted to carry electrical signals to and from a heart, the main lead body having a lumen therethrough, the main lead body having a preformed curve therein;
a first electrode disposed on the main lead body; and
a supplemental lead body having a second electrode, the supplemental lead body movably disposed within the lumen of the main lead body.

16. The lead as recited in claim 15, wherein the supplemental lead disposed within an atrium of the heart, and the supplemental lead includes an active fixation mechanism.

17. The lead as recited in 16, wherein the supplemental lead body extends from a terminal end to a distal end, the distal end having a J-shape.

18. The lead as recited in claim 15, wherein the supplemental lead body extends from a terminal end to a distal end, and the supplemental lead body is adapted to be rotated within the main lead body using the terminal end of the supplemental lead body.

19. The lead as recited in claim 15, wherein the lumen extends through the main lead body and ends at an aperture at an intermediate portion of the main lead body, and the aperture is transverse to a longitudinal axis of the main lead body.

20. The lead as recited in claim 15, wherein the supplemental lead disposed within an atrium of the heart, and the supplemental lead includes an active fixation mechanism.

21. The lead as recited in 20, wherein the supplemental lead body extends from a terminal end to a distal end, the distal end having a J-shape.

* * * * *